(12) United States Patent
Shelton, IV et al.

(10) Patent No.: US 8,157,145 B2
(45) Date of Patent: Apr. 17, 2012

(54) PNEUMATICALLY POWERED SURGICAL CUTTING AND FASTENING INSTRUMENT WITH ELECTRICAL FEEDBACK

(75) Inventors: Frederick E. Shelton, IV, New Vienna, OH (US); Randall J. Tanguay, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1171 days.

(21) Appl. No.: 11/809,156

(22) Filed: May 31, 2007

(65) Prior Publication Data

US 2008/0300580 A1    Dec. 4, 2008

(51) Int. Cl.
*A61B 17/068* (2006.01)
(52) U.S. Cl. .................... 227/175.1; 227/19; 606/219
(58) Field of Classification Search .... 227/175.1–182.1, 227/19; 606/219
See application file for complete search history.

(56) References Cited

U.S. PATENT DOCUMENTS

| | | | |
|---|---|---|---|
| 2,853,074 A | 9/1958 | Olson | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 3,902,247 A | 9/1975 | Fleer et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,522,327 A | 6/1985 | Korthoff et al. | |
| 4,530,453 A | 7/1985 | Green | |
| 4,566,620 A | 1/1986 | Green et al. | |
| 4,573,622 A | 3/1986 | Green et al. | |
| 4,580,712 A | 4/1986 | Green | |
| 4,610,383 A | 9/1986 | Rothfuss et al. | |

(Continued)

FOREIGN PATENT DOCUMENTS

CA    2458946 A1    3/2003

(Continued)

OTHER PUBLICATIONS

U.S. Appl. No. 11/497,937, filed Aug. 2, 2006.

(Continued)

*Primary Examiner* — Lindsay Low

(57) ABSTRACT

A status module for use with a pneumatically powered surgical instrument includes at least one sensor and a housing structured and arranged to releasably connect to the pneumatically powered surgical instrument. At least one contact is connected to the pneumatically powered surgical instrument. Each individual contact is structured and arranged to be in electrical communication with a different sensor when the housing is connected to the pneumatically powered surgical instrument. The at least one sensor is fluidically coupled to the pneumatically powered surgical instrument. A circuit is in electrical communication with the least one contact and at least one of a plurality of indicators.

24 Claims, 36 Drawing Sheets

U.S. PATENT DOCUMENTS

| | | |
|---|---|---|
| 4,619,262 A | 10/1986 | Taylor |
| 4,629,107 A | 12/1986 | Fedotov et al. |
| 4,632,290 A | 12/1986 | Green et al. |
| 4,655,222 A | 4/1987 | Florez et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A | 7/1989 | Arata et al. |
| 4,869,414 A | 9/1989 | Green et al. |
| 4,869,415 A | 9/1989 | Fox |
| 4,938,408 A | 7/1990 | Bedi et al. |
| 4,941,623 A | 7/1990 | Pruitt |
| 4,944,443 A | 7/1990 | Oddsen et al. |
| 4,951,861 A | 8/1990 | Schulze et al. |
| 5,005,754 A | 4/1991 | Van Overloop |
| 5,065,929 A | 11/1991 | Schulze et al. |
| 5,071,430 A | 12/1991 | de Salis et al. |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,221,036 A | 6/1993 | Takase |
| 5,222,975 A | 6/1993 | Crainich |
| 5,236,440 A | 8/1993 | Hlavacek |
| 5,258,009 A | 11/1993 | Conners |
| 5,282,829 A | 2/1994 | Hermes |
| 5,304,204 A | 4/1994 | Bregen |
| 5,342,395 A | 8/1994 | Jarrett et al. |
| 5,342,396 A | 8/1994 | Cook |
| 5,350,400 A | 9/1994 | Esposito et al. |
| 5,364,001 A * | 11/1994 | Bryan ........................ 227/175.1 |
| 5,366,479 A | 11/1994 | McGarry et al. |
| 5,383,880 A | 1/1995 | Hooven |
| 5,405,072 A | 4/1995 | Zlock et al. |
| 5,413,272 A | 5/1995 | Green et al. |
| 5,417,361 A | 5/1995 | Williamson, IV |
| 5,425,745 A | 6/1995 | Green et al. |
| 5,467,911 A * | 11/1995 | Tsuruta et al. ............. 227/175.1 |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A * | 1/1996 | Sorrentino et al. ........ 227/175.1 |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,505,363 A | 4/1996 | Green et al. |
| 5,509,596 A | 4/1996 | Green et al. |
| 5,518,163 A * | 5/1996 | Hooven ............................ 227/5 |
| 5,520,700 A * | 5/1996 | Beyar et al. .................. 606/139 |
| 5,529,235 A * | 6/1996 | Boiarski et al. ............ 227/175.1 |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,542,594 A | 8/1996 | McKean et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,575,799 A * | 11/1996 | Bolanos et al. ............... 606/139 |
| 5,577,654 A | 11/1996 | Bishop |
| 5,579,978 A | 12/1996 | Green et al. |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,624,452 A * | 4/1997 | Yates ............................ 606/139 |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,658,300 A * | 8/1997 | Bito et al. .................... 606/143 |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,690,269 A | 11/1997 | Bolanos et al. |
| 5,692,668 A | 12/1997 | Schulze et al. |
| 5,697,543 A | 12/1997 | Burdorff |
| 5,704,534 A | 1/1998 | Huitema et al. |
| 5,706,998 A | 1/1998 | Plyley et al. |
| 5,709,334 A | 1/1998 | Sorrentino et al. |
| 5,711,472 A | 1/1998 | Bryan |
| 5,713,505 A | 2/1998 | Huitema |
| 5,715,987 A | 2/1998 | Kelley et al. |
| 5,718,360 A | 2/1998 | Green et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,256 A | 6/1998 | Mastri et al. |
| 5,769,791 A | 6/1998 | Benaron et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A * | 7/1998 | Koukline ..................... 227/176.1 |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,829,662 A | 11/1998 | Allen et al. |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson, IV et al. |
| 5,893,506 A | 4/1999 | Powell |
| 5,901,895 A | 5/1999 | Heaton et al. |
| 5,911,353 A | 6/1999 | Bolanos et al. |

| | | | | | | |
|---|---|---|---|---|---|---|
| 5,915,616 A | 6/1999 | Viola et al. | | 7,083,075 B2 | 8/2006 | Swayze et al. |
| 5,918,791 A | 7/1999 | Sorrentino et al. | | 7,108,709 B2 | 9/2006 | Cummins |
| 5,941,442 A | 8/1999 | Geiste et al. | | 7,111,769 B2 | 9/2006 | Wales et al. |
| 5,954,259 A | 9/1999 | Viola et al. | | 7,114,642 B2 | 10/2006 | Whitman |
| 6,010,054 A | 1/2000 | Johnson et al. | | 7,121,446 B2 | 10/2006 | Arad et al. |
| 6,032,849 A | 3/2000 | Mastri et al. | | 7,128,253 B2 | 10/2006 | Mastri et al. |
| 6,083,242 A | 7/2000 | Cook | | 7,128,254 B2 | 10/2006 | Shelton, IV et al. |
| 6,099,551 A | 8/2000 | Gabbay | | 7,140,527 B2 | 11/2006 | Ehrenfels et al. |
| 6,102,271 A | 8/2000 | Longo et al. | | 7,143,926 B2 | 12/2006 | Shelton, IV et al. |
| 6,119,913 A | 9/2000 | Adams et al. | | 7,147,138 B2 | 12/2006 | Shelton, IV |
| 6,126,058 A | 10/2000 | Adams et al. | | 7,147,139 B2 | 12/2006 | Schwemberger et al. |
| 6,171,330 B1 | 1/2001 | Benchetrit | | 7,156,863 B2 | 1/2007 | Sonnenschein et al. |
| 6,193,129 B1 | 2/2001 | Bittner et al. | | 7,159,750 B2 | 1/2007 | Racenet et al. |
| 6,202,914 B1 | 3/2001 | Geiste et al. | | 7,168,604 B2 | 1/2007 | Milliman et al. |
| 6,241,139 B1 | 6/2001 | Milliman et al. | | 7,182,239 B1 | 2/2007 | Myers |
| 6,250,532 B1 | 6/2001 | Green et al. | | 7,188,758 B2 | 3/2007 | Viola et al. |
| 6,264,086 B1 | 7/2001 | McGuckin, Jr. | | 7,207,471 B2 | 4/2007 | Heinrich et al. |
| 6,264,087 B1 * | 7/2001 | Whitman ................... 227/180.1 | | 7,207,472 B2 | 4/2007 | Wukusick et al. |
| 6,302,311 B1 | 10/2001 | Adams et al. | | 7,210,609 B2 | 5/2007 | Leiboff et al. |
| 6,315,184 B1 | 11/2001 | Whitman | | 7,213,736 B2 | 5/2007 | Wales et al. |
| 6,330,965 B1 | 12/2001 | Milliman et al. | | 7,220,272 B2 | 5/2007 | Weadock |
| 6,387,113 B1 | 5/2002 | Hawkins et al. | | 7,225,964 B2 | 6/2007 | Mastri et al. |
| RE37,814 E | 8/2002 | Allgeyer | | 7,234,624 B2 | 6/2007 | Gresham et al. |
| 6,436,107 B1 | 8/2002 | Wang et al. | | 7,237,708 B1 | 7/2007 | Guy et al. |
| 6,443,973 B1 * | 9/2002 | Whitman ..................... 606/219 | | 7,238,195 B2 | 7/2007 | Viola |
| 6,488,196 B1 | 12/2002 | Fenton, Jr. | | 7,246,734 B2 | 7/2007 | Shelton, IV |
| 6,488,197 B1 | 12/2002 | Whitman | | 7,258,262 B2 | 8/2007 | Mastri et al. |
| 6,491,201 B1 | 12/2002 | Whitman | | 7,278,562 B2 | 10/2007 | Mastri et al. |
| 6,505,768 B2 | 1/2003 | Whitman | | 7,278,563 B1 | 10/2007 | Green |
| 6,517,565 B1 | 2/2003 | Whitman et al. | | 7,296,724 B2 | 11/2007 | Green et al. |
| 6,578,751 B2 | 6/2003 | Hartwick | | 7,303,106 B2 | 12/2007 | Milliman et al. |
| 6,588,643 B2 | 7/2003 | Bolduc et al. | | 7,303,107 B2 | 12/2007 | Milliman et al. |
| 6,601,749 B2 | 8/2003 | Sullivan et al. | | 7,303,108 B2 | 12/2007 | Shelton, IV |
| 6,616,686 B2 | 9/2003 | Coleman et al. | | 7,328,828 B2 | 2/2008 | Ortiz et al. |
| 6,619,529 B2 | 9/2003 | Green et al. | | 7,328,829 B2 | 2/2008 | Arad et al. |
| 6,629,630 B2 | 10/2003 | Adams | | 7,334,717 B2 | 2/2008 | Rethy et al. |
| 6,629,988 B2 | 10/2003 | Weadock | | 7,354,447 B2 | 4/2008 | Shelton, IV et al. |
| 6,644,532 B2 | 11/2003 | Green et al. | | 7,364,060 B2 | 4/2008 | Milliman |
| 6,681,978 B2 | 1/2004 | Geiste et al. | | 7,364,061 B2 | 4/2008 | Swayze et al. |
| 6,681,979 B2 | 1/2004 | Whitman | | 7,380,695 B2 | 6/2008 | Doll et al. |
| 6,695,199 B2 | 2/2004 | Whitman | | 7,380,696 B2 | 6/2008 | Shelton, IV et al. |
| 6,698,643 B2 | 3/2004 | Whitman | | 7,398,907 B2 | 7/2008 | Racenet et al. |
| 6,716,233 B1 | 4/2004 | Whitman | | 7,398,908 B2 | 7/2008 | Holsten et al. |
| 6,722,550 B1 | 4/2004 | Ricordi et al. | | 7,404,508 B2 | 7/2008 | Smith et al. |
| 6,755,338 B2 | 6/2004 | Hahnen et al. | | 7,404,509 B2 | 7/2008 | Ortiz et al. |
| 6,769,594 B2 | 8/2004 | Orban, III | | 7,407,075 B2 | 8/2008 | Holsten et al. |
| 6,786,382 B1 | 9/2004 | Hoffman | | 7,407,078 B2 | 8/2008 | Shelton, IV et al. |
| 6,805,273 B2 | 10/2004 | Bilotti et al. | | 7,410,086 B2 | 8/2008 | Ortiz et al. |
| 6,817,508 B1 | 11/2004 | Racenet et al. | | 7,416,101 B2 | 8/2008 | Shelton, IV et al. |
| 6,817,509 B2 | 11/2004 | Geiste et al. | | 7,419,080 B2 | 9/2008 | Smith et al. |
| 6,830,174 B2 | 12/2004 | Hillstead et al. | | 7,422,136 B1 | 9/2008 | Marczyk |
| 6,843,403 B2 | 1/2005 | Whitman | | 7,422,139 B2 | 9/2008 | Shelton, IV et al. |
| RE38,708 E | 3/2005 | Bolanos et al. | | 7,424,965 B2 | 9/2008 | Racenet et al. |
| 6,872,214 B2 | 3/2005 | Sonnenschein et al. | | 7,431,188 B1 | 10/2008 | Marczyk |
| 6,874,669 B2 | 4/2005 | Adams et al. | | 7,431,189 B2 | 10/2008 | Shelton, IV et al. |
| 6,877,647 B2 | 4/2005 | Green et al. | | 7,431,730 B2 | 10/2008 | Viola |
| 6,905,057 B2 | 6/2005 | Swayze et al. | | 7,434,717 B2 | 10/2008 | Shelton, IV et al. |
| 6,945,444 B2 | 9/2005 | Gresham et al. | | 7,438,209 B1 | 10/2008 | Hess et al. |
| 6,953,138 B1 | 10/2005 | Dworak et al. | | 7,441,684 B2 | 10/2008 | Shelton, IV et al. |
| 6,953,139 B2 | 10/2005 | Milliman et al. | | 7,441,685 B1 | 10/2008 | Boudreaux |
| 6,959,852 B2 | 11/2005 | Shelton, IV et al. | | 7,448,525 B2 | 11/2008 | Shelton, IV et al. |
| 6,964,363 B2 | 11/2005 | Wales et al. | | 7,455,208 B2 | 11/2008 | Wales et al. |
| 6,978,921 B2 | 12/2005 | Shelton, IV et al. | | 7,464,847 B2 * | 12/2008 | Viola et al. .................. 227/175.2 |
| 6,978,922 B2 | 12/2005 | Bilotti et al. | | 7,464,849 B2 | 12/2008 | Shelton, IV et al. |
| 6,981,628 B2 | 1/2006 | Wales | | 7,467,740 B2 | 12/2008 | Shelton, IV et al. |
| 6,981,941 B2 | 1/2006 | Whitman et al. | | 7,472,815 B2 | 1/2009 | Shelton, IV et al. |
| 6,986,451 B1 | 1/2006 | Mastri et al. | | 7,481,349 B2 | 1/2009 | Holsten et al. |
| 6,988,650 B2 | 1/2006 | Schwemberger et al. | | 7,490,749 B2 | 2/2009 | Schall et al. |
| 7,000,818 B2 | 2/2006 | Shelton, IV et al. | | 7,494,039 B2 | 2/2009 | Racenet et al. |
| 7,000,819 B2 | 2/2006 | Swayze et al. | | 7,500,979 B2 | 3/2009 | Hueil et al. |
| 7,032,798 B2 | 4/2006 | Whitman et al. | | 7,506,790 B2 | 3/2009 | Shelton, IV |
| 7,032,799 B2 | 4/2006 | Viola et al. | | 7,506,791 B2 | 3/2009 | Omaits et al. |
| 7,044,352 B2 | 5/2006 | Shelton, IV et al. | | 7,510,107 B2 | 3/2009 | Timm et al. |
| 7,044,353 B2 | 5/2006 | Mastri et al. | | 7,546,940 B2 | 6/2009 | Milliman et al. |
| 7,055,731 B2 | 6/2006 | Shelton, IV et al. | | 7,549,564 B2 | 6/2009 | Boudreaux |
| 7,056,330 B2 | 6/2006 | Gayton | | 7,556,186 B2 | 7/2009 | Milliman |
| 7,070,083 B2 | 7/2006 | Jankowski | | 7,559,450 B2 | 7/2009 | Wales et al. |
| 7,077,856 B2 | 7/2006 | Whitman | | 7,568,603 B2 | 8/2009 | Shelton, IV et al. |
| 7,080,769 B2 | 7/2006 | Vresh et al. | | 7,568,604 B2 | 8/2009 | Ehrenfels et al. |

| Patent No. | Date | Inventor |
|---|---|---|
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,631,793 B2 | 12/2009 | Rethy et al. |
| 7,644,848 B2 | 1/2010 | Swayze et al. |
| 7,658,311 B2 | 2/2010 | Boudreaux |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,699,204 B2 | 4/2010 | Viola |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,770,775 B2 | 8/2010 | Shelton, IV et al. |
| 7,780,054 B2 | 8/2010 | Wales |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 8,002,795 B2 | 8/2011 | Beetel |
| 2002/0117534 A1 | 8/2002 | Green et al. |
| 2004/0006372 A1 | 1/2004 | Racenet et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0103819 A1 | 5/2005 | Racenet et al. |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0240222 A1 | 10/2005 | Shipp |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1* | 3/2006 | Shelton et al. ............. 227/175.2 |
| 2006/0085033 A1 | 4/2006 | Criscuolo et al. |
| 2006/0108393 A1 | 5/2006 | Heinrich et al. |
| 2006/0112773 A1 | 6/2006 | Hedtke |
| 2006/0151567 A1 | 7/2006 | Roy |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0273135 A1* | 12/2006 | Beetel ........................ 227/175.1 |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0073341 A1 | 3/2007 | Smith |
| 2007/0084897 A1 | 4/2007 | Shelton, IV et al. |
| 2007/0102472 A1 | 5/2007 | Shelton, IV |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175958 A1 | 8/2007 | Shelton, IV et al. |
| 2007/0175960 A1 | 8/2007 | Shelton, IV et al. |
| 2007/0175964 A1 | 8/2007 | Shelton, IV et al. |
| 2007/0179408 A1 | 8/2007 | Soltz |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0197954 A1 | 8/2007 | Keenan |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0246505 A1 | 10/2007 | Pace-Floridia et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |

| | | |
|---|---|---|
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0237296 A1 | 10/2008 | Boudreaux et al. |
| 2008/0251568 A1 | 10/2008 | Zemlok et al. |
| 2008/0283570 A1 | 11/2008 | Boyden et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2010/0001036 A1 | 1/2010 | Marczyk et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132962 A1 | 6/2011 | Hall et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |

FOREIGN PATENT DOCUMENTS

| | | |
|---|---|---|
| CA | 2512960 A1 | 1/2006 |
| CA | 2514274 A1 | 1/2006 |
| CN | 1915180 A | 2/2007 |
| DE | 1775926 A | 1/1972 |
| DE | 3210466 A1 | 9/1983 |
| DE | 9412228 U | 9/1994 |
| DE | 19509116 A1 | 9/1996 |
| DE | 19924311 A1 | 11/2000 |
| DE | 69328576 T2 | 1/2001 |
| DE | 10052679 A1 | 5/2001 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |

| | | | | | | | |
|---|---|---|---|---|---|---|---|
| EP | 0593920 | A1 | 4/1994 | EP | 0869742 | B1 | 5/2003 |
| EP | 0523174 | B1 | 6/1994 | EP | 0829235 | B1 | 6/2003 |
| EP | 0600182 | A2 | 6/1994 | EP | 0887046 | B1 | 7/2003 |
| EP | 0310431 | 81 | 11/1994 | EP | 0852480 | B1 | 8/2003 |
| EP | 0375302 | B1 | 11/1994 | EP | 0891154 | B1 | 9/2003 |
| EP | 0376562 | B1 | 11/1994 | EP | 0813843 | B1 | 10/2003 |
| EP | 0630612 | A1 | 12/1994 | EP | 0873089 | B1 | 10/2003 |
| EP | 0634144 | A1 | 1/1995 | EP | 0856326 | B1 | 11/2003 |
| EP | 0646356 | A2 | 4/1995 | EP | 1374788 | A1 | 1/2004 |
| EP | 0646357 | A1 | 4/1995 | EP | 0741996 | B1 | 2/2004 |
| EP | 0653189 | A2 | 5/1995 | EP | 0814712 | B1 | 2/2004 |
| EP | 0669104 | A1 | 8/1995 | EP | 1402837 | A1 | 3/2004 |
| EP | 0511470 | B1 | 10/1995 | EP | 0705570 | B1 | 4/2004 |
| EP | 0679367 | A2 | 11/1995 | EP | 0959784 | B1 | 4/2004 |
| EP | 0392547 | B1 | 12/1995 | EP | 1407719 | A2 | 4/2004 |
| EP | 0685204 | A1 | 12/1995 | EP | 1086713 | B1 | 5/2004 |
| EP | 0364216 | 81 | 1/1996 | EP | 0996378 | B1 | 6/2004 |
| EP | 0699418 | A1 | 3/1996 | EP | 1426012 | A1 | 6/2004 |
| EP | 0702937 | A1 | 3/1996 | EP | 0833593 | B2 | 7/2004 |
| EP | 0705571 | A1 | 4/1996 | EP | 1442694 | A1 | 8/2004 |
| EP | 0711611 | A2 | 5/1996 | EP | 0888749 | B1 | 9/2004 |
| EP | 0484677 | B2 | 6/1996 | EP | 0959786 | B1 | 9/2004 |
| EP | 0541987 | B1 | 7/1996 | EP | 1459695 | A1 | 9/2004 |
| EP | 0667119 | B1 | 7/1996 | EP | 1473819 | A1 | 11/2004 |
| EP | 0708618 | B1 | 3/1997 | EP | 1477119 | A1 | 11/2004 |
| EP | 0770355 | A1 | 5/1997 | EP | 1479345 | A1 | 11/2004 |
| EP | 0503662 | B1 | 6/1997 | EP | 1479347 | A1 | 11/2004 |
| EP | 0447121 | B1 | 7/1997 | EP | 1479348 | A1 | 11/2004 |
| EP | 0625077 | B1 | 7/1997 | EP | 0754437 | B2 | 12/2004 |
| EP | 0633749 | B1 | 8/1997 | EP | 1025807 | B1 | 12/2004 |
| EP | 0710090 | B1 | 8/1997 | EP | 1001710 | B1 | 1/2005 |
| EP | 0578425 | B1 | 9/1997 | EP | 1520521 | A1 | 4/2005 |
| EP | 0625335 | B1 | 11/1997 | EP | 1520523 | A1 | 4/2005 |
| EP | 0552423 | B1 | 1/1998 | EP | 1520525 | A1 | 4/2005 |
| EP | 0592244 | B1 | 1/1998 | EP | 1522264 | A1 | 4/2005 |
| EP | 0648476 | B1 | 1/1998 | EP | 1523942 | A2 | 4/2005 |
| EP | 0649290 | B1 | 3/1998 | EP | 1550408 | A1 | 7/2005 |
| EP | 0598618 | B1 | 9/1998 | EP | 1557129 | A1 | 7/2005 |
| EP | 0676173 | B1 | 9/1998 | EP | 1064883 | B1 | 8/2005 |
| EP | 0678007 | B1 | 9/1998 | EP | 1067876 | 81 | 8/2005 |
| EP | 0603472 | B1 | 11/1998 | EP | 0870473 | B1 | 9/2005 |
| EP | 0605351 | B1 | 11/1998 | EP | 1157666 | B1 | 9/2005 |
| EP | 0878169 | A1 | 11/1998 | EP | 0880338 | B1 | 10/2005 |
| EP | 0879742 | A1 | 11/1998 | EP | 1158917 | B1 | 11/2005 |
| EP | 0695144 | B1 | 12/1998 | EP | 1344498 | B1 | 11/2005 |
| EP | 0722296 | B1 | 12/1998 | EP | 1330989 | B1 | 12/2005 |
| EP | 0760230 | B1 | 2/1999 | EP | 0771176 | B2 | 1/2006 |
| EP | 0623316 | B1 | 3/1999 | EP | 1621138 | A2 | 2/2006 |
| EP | 0650701 | B1 | 3/1999 | EP | 1621139 | A2 | 2/2006 |
| EP | 0537572 | B1 | 6/1999 | EP | 1621141 | A2 | 2/2006 |
| EP | 0923907 | A1 | 6/1999 | EP | 1621145 | A2 | 2/2006 |
| EP | 0843906 | B1 | 3/2000 | EP | 1621151 | A2 | 2/2006 |
| EP | 0552050 | B1 | 5/2000 | EP | 1034746 | B1 | 3/2006 |
| EP | 0833592 | B1 | 5/2000 | EP | 1632191 | A2 | 3/2006 |
| EP | 0830094 | 81 | 9/2000 | EP | 1065981 | B1 | 5/2006 |
| EP | 1034747 | A1 | 9/2000 | EP | 1082944 | B1 | 5/2006 |
| EP | 1034748 | A1 | 9/2000 | EP | 1652481 | A2 | 5/2006 |
| EP | 0694290 | B1 | 11/2000 | EP | 1382303 | B1 | 6/2006 |
| EP | 1050278 | A1 | 11/2000 | EP | 1253866 | B1 | 7/2006 |
| EP | 1053719 | A1 | 11/2000 | EP | 1032318 | B1 | 8/2006 |
| EP | 1053720 | A1 | 11/2000 | EP | 1045672 | B1 | 8/2006 |
| EP | 1055399 | A1 | 11/2000 | EP | 1617768 | B1 | 8/2006 |
| EP | 1055400 | A1 | 11/2000 | EP | 1693015 | A2 | 8/2006 |
| EP | 1080694 | A1 | 3/2001 | EP | 1400214 | B1 | 9/2006 |
| EP | 1090592 | A1 | 4/2001 | EP | 1702567 | A2 | 9/2006 |
| EP | 1095627 | A1 | 5/2001 | EP | 1129665 | B1 | 11/2006 |
| EP | 1256318 | B1 | 5/2001 | EP | 1400206 | B1 | 11/2006 |
| EP | 0806914 | B1 | 9/2001 | EP | 1256317 | B1 | 12/2006 |
| EP | 0768840 | B1 | 12/2001 | EP | 1728473 | A1 | 12/2006 |
| EP | 0908152 | B1 | 1/2002 | EP | 1728475 | A2 | 12/2006 |
| EP | 0872213 | B1 | 5/2002 | EP | 1479346 | B1 | 1/2007 |
| EP | 0862386 | B1 | 6/2002 | EP | 1484024 | B1 | 1/2007 |
| EP | 0949886 | B1 | 9/2002 | EP | 1754445 | A2 | 2/2007 |
| EP | 1238634 | A2 | 9/2002 | EP | 1759812 | A1 | 3/2007 |
| EP | 0858295 | B1 | 12/2002 | EP | 1767163 | A1 | 3/2007 |
| EP | 0656188 | B1 | 1/2003 | EP | 1769756 | A1 | 4/2007 |
| EP | 1284120 | A1 | 2/2003 | EP | 1769758 | A1 | 4/2007 |
| EP | 1287788 | B1 | 3/2003 | EP | 1581128 | B1 | 5/2007 |
| EP | 0717966 | B1 | 4/2003 | EP | 1785097 | A2 | 5/2007 |

| | | | | | | |
|---|---|---|---|---|---|---|
| EP | 1790293 | A2 | 5/2007 | WO | WO 93/14690 A1 | 8/1993 |
| EP | 1800610 | A1 | 6/2007 | WO | WO 93/15850 A1 | 8/1993 |
| EP | 1300117 | 81 | 8/2007 | WO | WO 93/19681 A1 | 10/1993 |
| EP | 1813199 | A1 | 8/2007 | WO | WO 94/00060 A1 | 1/1994 |
| EP | 1813201 | A1 | 8/2007 | WO | WO 94/11057 A1 | 5/1994 |
| EP | 1813203 | A2 | 8/2007 | WO | WO 94/12108 A1 | 6/1994 |
| EP | 1813207 | A1 | 8/2007 | WO | WO 94/18893 A1 | 9/1994 |
| EP | 1813209 | A1 | 8/2007 | WO | WO 94/22378 A1 | 10/1994 |
| EP | 1487359 | B1 | 10/2007 | WO | WO 94/23659 A1 | 10/1994 |
| EP | 1599146 | B1 | 10/2007 | WO | WO 95/02369 A1 | 1/1995 |
| EP | 1839596 | A1 | 10/2007 | WO | WO 95/03743 A1 | 2/1995 |
| EP | 1402821 | B1 | 12/2007 | WO | WO 95/06817 A1 | 3/1995 |
| EP | 1872727 | A1 | 1/2008 | WO | WO 95/09576 A1 | 4/1995 |
| EP | 1897502 | A1 | 3/2008 | WO | WO 95/09577 A1 | 4/1995 |
| EP | 1330201 | B1 | 6/2008 | WO | WO 95/14436 A1 | 6/1995 |
| EP | 1702568 | B1 | 7/2008 | WO | WO 95/17855 A1 | 7/1995 |
| EP | 1943976 | A2 | 7/2008 | WO | WO 95/18383 A1 | 7/1995 |
| EP | 1593337 | B1 | 8/2008 | WO | WO 95/18572 A1 | 7/1995 |
| EP | 1970014 | A1 | 9/2008 | WO | WO 95/19739 A1 | 7/1995 |
| EP | 1980213 | A2 | 10/2008 | WO | WO 95/20360 A1 | 8/1995 |
| EP | 1759645 | B1 | 11/2008 | WO | WO 95/23557 A1 | 9/1995 |
| EP | 1693008 | B1 | 12/2008 | WO | WO 95/24865 A1 | 9/1995 |
| EP | 1759640 | B1 | 12/2008 | WO | WO 95/25471 A3 | 9/1995 |
| EP | 2000102 | A2 | 12/2008 | WO | WO 95/26562 A1 | 10/1995 |
| EP | 1736104 | B1 | 3/2009 | WO | WO 95/29639 A1 | 11/1995 |
| EP | 1749486 | B1 | 3/2009 | WO | WO 96/04858 A1 | 2/1996 |
| EP | 1721576 | B1 | 4/2009 | WO | WO 96/19151 A1 | 6/1996 |
| EP | 1733686 | B1 | 4/2009 | WO | WO 96/19152 A1 | 6/1996 |
| EP | 1745748 | B1 | 8/2009 | WO | WO 96/20652 A1 | 7/1996 |
| EP | 2090256 | A2 | 8/2009 | WO | WO 96/21119 A1 | 7/1996 |
| EP | 1607050 | B1 | 12/2009 | WO | WO 96/22055 A1 | 7/1996 |
| EP | 1566150 | B1 | 4/2010 | WO | WO 96/23448 A1 | 8/1996 |
| EP | 1813206 | B1 | 4/2010 | WO | WO 96/24301 A1 | 8/1996 |
| EP | 1769754 | B1 | 6/2010 | WO | WO 96/27337 A1 | 9/1996 |
| EP | 1535565 | B1 | 10/2010 | WO | WO 96/35464 A1 | 11/1996 |
| EP | 1702570 | B1 | 10/2010 | WO | WO 96/39085 A1 | 12/1996 |
| EP | 1785098 | B1 | 10/2010 | WO | WO 96/39086 A1 | 12/1996 |
| FR | 999646 | A | 2/1952 | WO | WO 96/39087 A1 | 12/1996 |
| FR | 2765794 | A | 1/1999 | WO | WO 96/39088 A1 | 12/1996 |
| GB | 939929 | A | 10/1963 | WO | WO 96/39089 A1 | 12/1996 |
| GB | 1210522 | A | 10/1970 | WO | WO 97/00646 A1 | 1/1997 |
| GB | 1217159 | A | 12/1970 | WO | WO 97/00647 A1 | 1/1997 |
| GB | 1339394 | A | 12/1973 | WO | WO 97/06582 A1 | 2/1997 |
| GB | 2109241 | A | 6/1983 | WO | WO 97/10763 A1 | 3/1997 |
| GB | 2272159 | A | 5/1994 | WO | WO 97/10764 A1 | 3/1997 |
| GB | 2284242 | A | 5/1995 | WO | WO 97/11648 A2 | 4/1997 |
| GB | 2336214 | A | 10/1999 | WO | WO 97/11649 A1 | 4/1997 |
| GB | 2425903 | A | 11/2006 | WO | WO 97/15237 A1 | 5/1997 |
| JP | 6007357 | A | 1/1994 | WO | WO 97/24073 A1 | 7/1997 |
| JP | 7051273 | A | 2/1995 | WO | WO 97/24993 A1 | 7/1997 |
| JP | 8033641 | A | 2/1996 | WO | WO 97/30644 A1 | 8/1997 |
| JP | 8229050 | A | 9/1996 | WO | WO 97/34533 A1 | 9/1997 |
| JP | 2000033071 | A | 2/2000 | WO | WO 97/37598 A1 | 10/1997 |
| JP | 2000171730 | A | 6/2000 | WO | WO 97/39688 A2 | 10/1997 |
| JP | 2000287987 | A | 10/2000 | WO | WO 98/17180 A1 | 4/1998 |
| JP | 2000325303 | A | 11/2000 | WO | WO 98/27880 A1 | 7/1998 |
| JP | 2001286477 | A | 10/2001 | WO | WO 98/30153 A1 | 7/1998 |
| JP | 2002143078 | A | 5/2002 | WO | WO 98/47436 A1 | 10/1998 |
| JP | 2002369820 | A | 12/2002 | WO | WO 99/03407 A1 | 1/1999 |
| JP | 2005505322 | T | 2/2005 | WO | WO 99/03408 A1 | 1/1999 |
| JP | 2005103293 | A | 4/2005 | WO | WO 99/03409 A1 | 1/1999 |
| JP | 2005131163 | A | 5/2005 | WO | WO 99/12483 A1 | 3/1999 |
| JP | 2005131164 | A | 5/2005 | WO | WO 99/12487 A1 | 3/1999 |
| JP | 2005131173 | A | 5/2005 | WO | WO 99/12488 A1 | 3/1999 |
| JP | 2005131211 | A | 5/2005 | WO | WO 99/15086 A1 | 4/1999 |
| JP | 2005131212 | A | 5/2005 | WO | WO 99/15091 A1 | 4/1999 |
| JP | 2005137423 | A | 6/2005 | WO | WO 99/23933 A2 | 5/1999 |
| JP | 2005152416 | A | 6/2005 | WO | WO 99/23959 A1 | 5/1999 |
| JP | 2006-281405 | A | 10/2006 | WO | WO 99/25261 A1 | 5/1999 |
| RU | 2187249 | C2 | 8/2002 | WO | WO 99/29244 A1 | 6/1999 |
| RU | 2225170 | C2 | 3/2004 | WO | WO 99/34744 A1 | 7/1999 |
| SU | 189517 | A | 1/1967 | WO | WO 99/45849 A1 | 9/1999 |
| SU | 328636 | A | 9/1972 | WO | WO 99/48430 A1 | 9/1999 |
| SU | 886900 | A1 | 12/1981 | WO | WO 99/51158 A1 | 10/1999 |
| SU | 1333319 | A2 | 8/1987 | WO | WO 00/24322 A1 | 5/2000 |
| WO | WO 91/15157 | A1 | 10/1991 | WO | WO 00/24330 A1 | 5/2000 |
| WO | WO 92/21300 | A1 | 12/1992 | WO | WO 00/41638 A1 | 7/2000 |
| WO | WO 93/08755 | A1 | 5/1993 | WO | WO 00/48506 A1 | 8/2000 |
| WO | WO 93/13718 | A1 | 7/1993 | WO | WO 00/53112 A2 | 9/2000 |

| | | |
|---|---|---|
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/117735 A1 | 12/2005 |
| WO | WO 2005/122936 A1 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

U.S. Appl. No. 11/809,089, filed May 31, 2007.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
European Search Report, Application 08251903.4, dated Oct. 5, 2010 (7 pages).
Datasheet for Panasonic TK Relays Ultra Low Profile 2 A Polarized Relay, Copyright Matsushita Electric Works, Ltd. (Known of at least as early as Aug. 17, 2010), 5 pages.

* cited by examiner

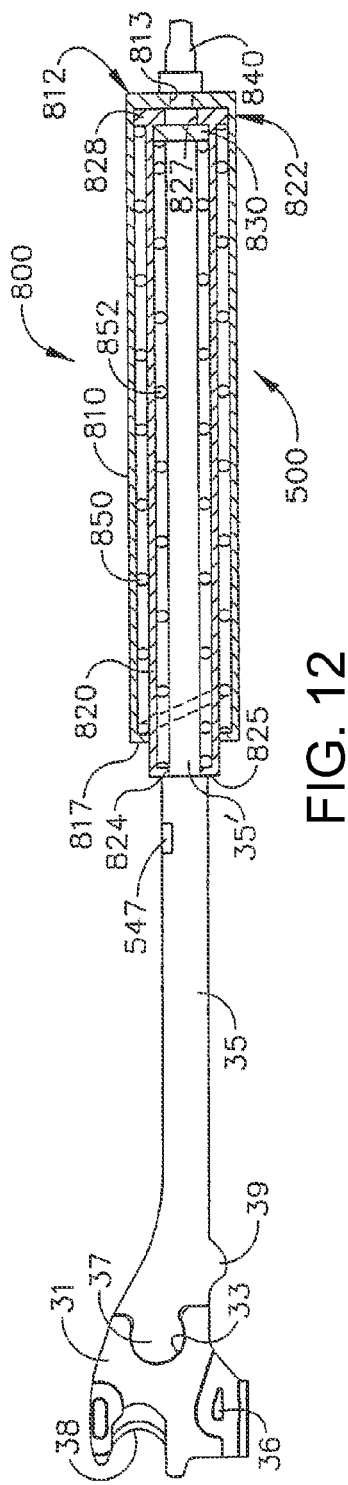
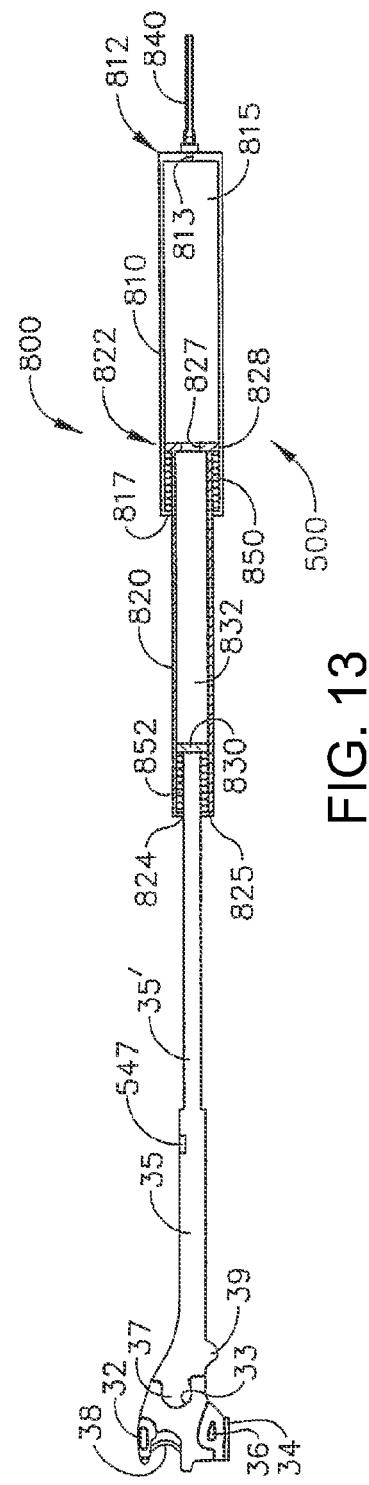
FIG. 12
FIG. 13

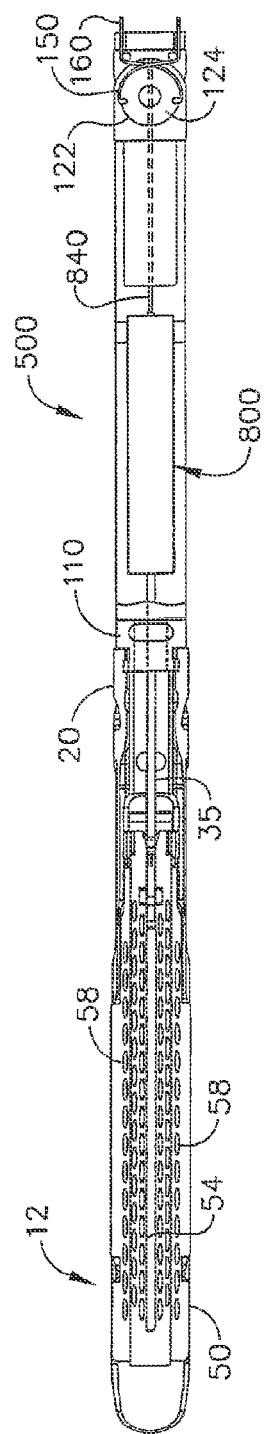
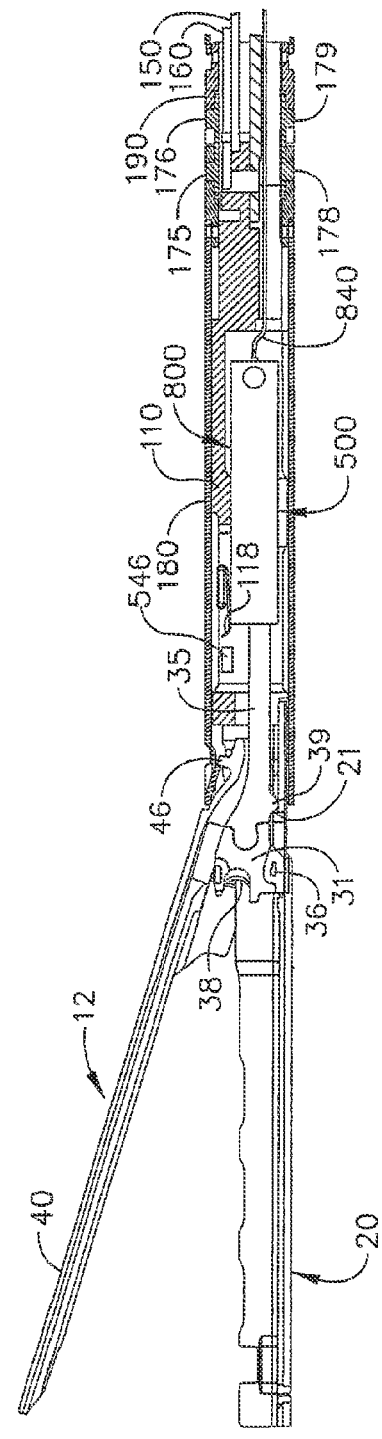
FIG. 14
FIG. 15

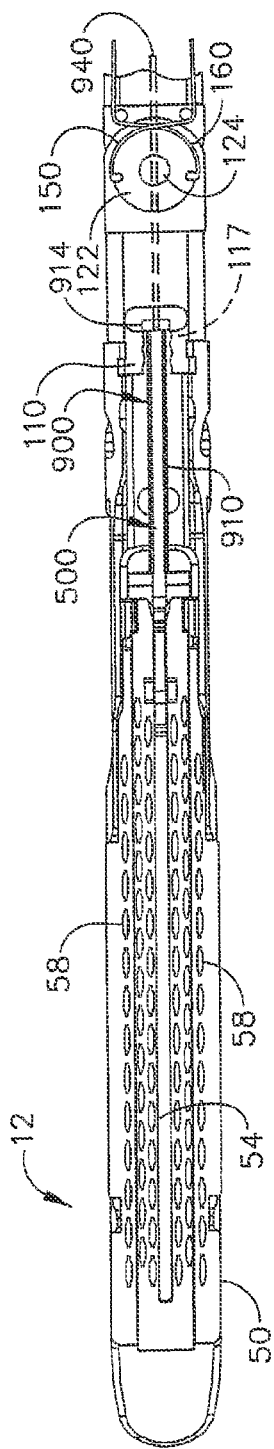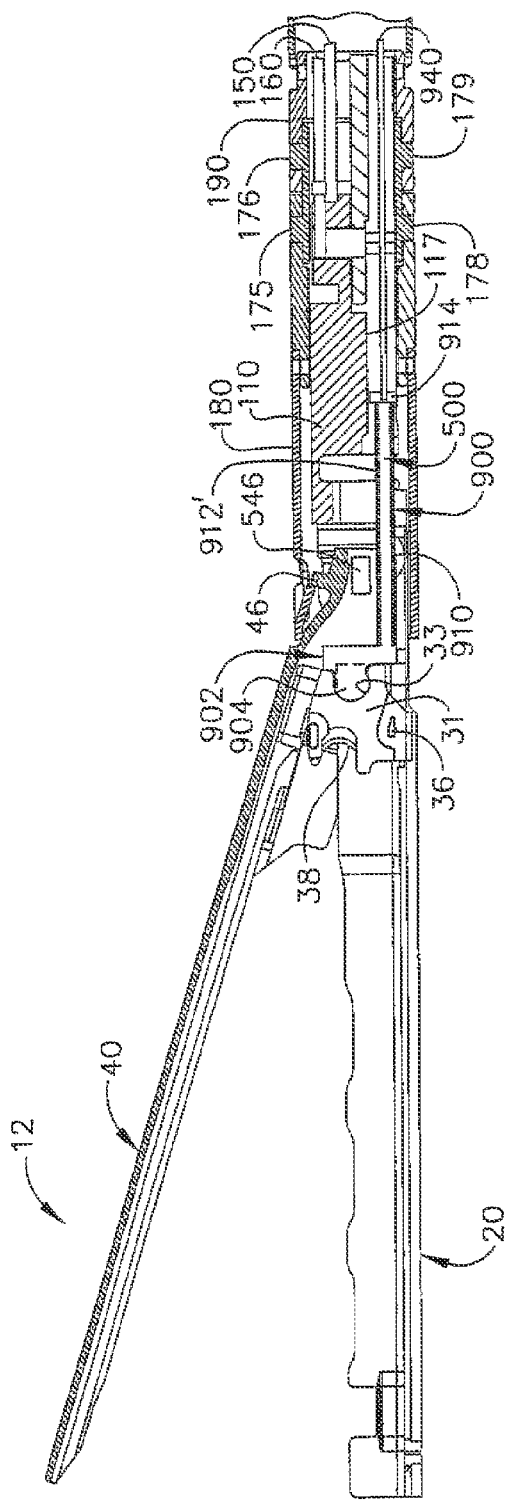
FIG. 17
FIG. 18

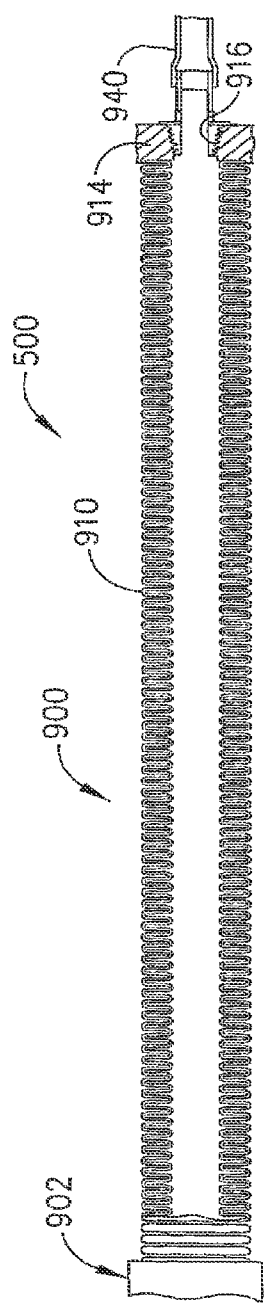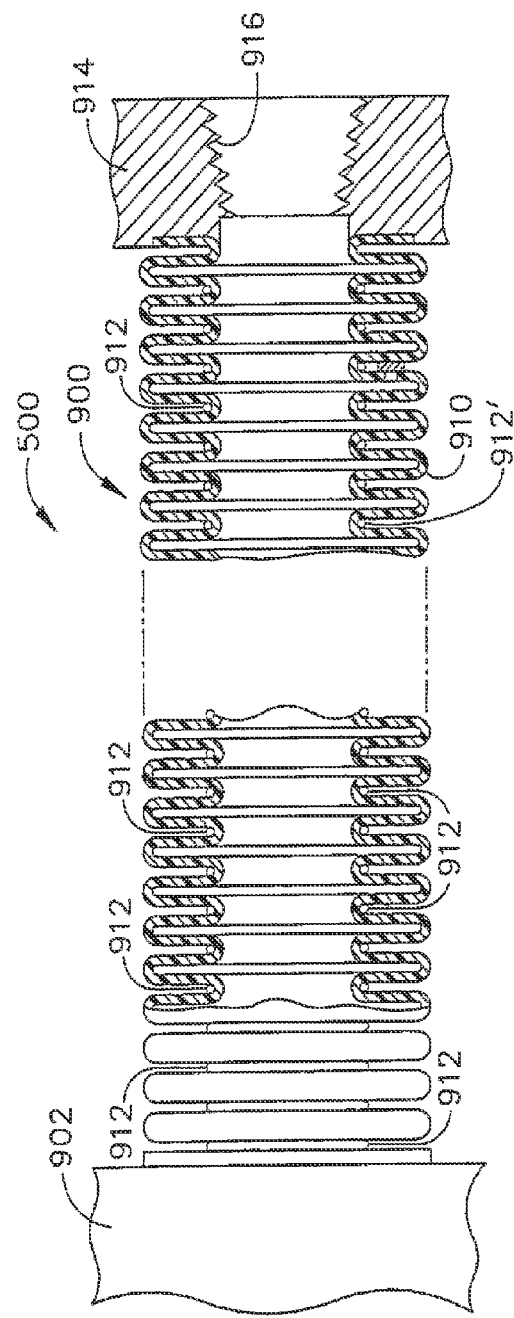
FIG. 19
FIG. 20

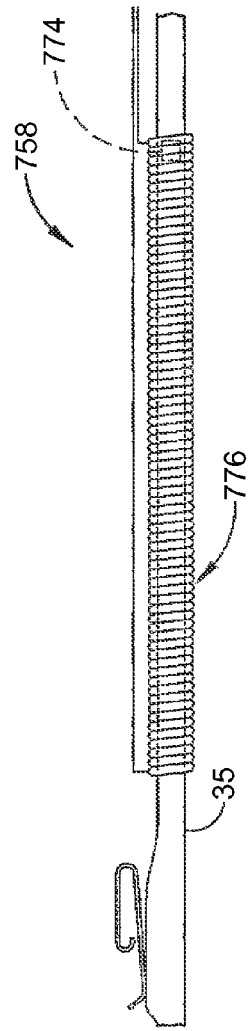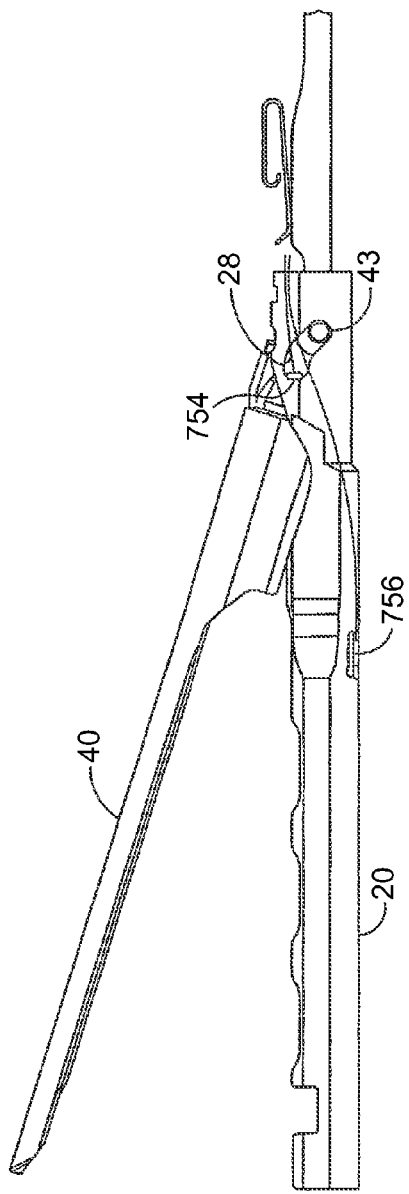

| EVENT # | CLOSURE LOAD | FIRING STROKE | FIRING LOAD (MAX) | KNIFE POSITION % | ANVIL CLOSED/OPEN | SLED PRESENT YES/NO | CARTRIDGE PRESENT YES/NO |
|---|---|---|---|---|---|---|---|
| 1 | 10 | | | | 0 | 1 | 1 |
| 2 | 12 | | | | 0 | 1 | 1 |
| 3 | 15 | | | | 0 | 1 | 1 |
| 4 | 50 | | | | 1 | 1 | 1 |
| 25 | 25 | 1 | 250 | .33 | 1 | 0 | 1 |
| 26 | 100 | 2 | 400 | .66 | 1 | 0 | 1 |
| 27 | 120 | 3 | 200 | .75 | 1 | 0 | 1 |
| 55 | 50 | | | | 1 | 0 | 1 |
| 56 | 50 | | | | 1 | 0 | 1 |

EXAMPLE: 3 STEP FIRING

FIG. 32

PNEUMATICALLY POWERED SURGICAL CUTTING AND FASTENING INSTRUMENT WITH ELECTRICAL FEEDBACK

CROSS REFERENCE TO RELATED APPLICATIONS

This application is related to the following concurrently filed U.S. patent application, which is incorporated herein by reference:

(1) U.S. patent application Ser. No. 11/809,089 for PNEUMATICALLY POWERED SURGICAL CUTTING AND FASTENING INSTRUMENT WITH ELECTRICAL CONTROL AND RECORDING MECHANISMS; Inventors: Frederick E. Shelton, IV; Randall J. Tanguay; and Jerome R. Morgan.

BACKGROUND

The present disclosure is generally directed to surgical apparatuses, systems, and methods and, more particularly, pneumatically powered surgical cutting and fastening instruments. The surgical apparatuses, systems, and methods may have application in conventional endoscopic and open surgical instrumentation as well as application in robotic-assisted surgery.

Surgical cutting and fastening instruments (staplers) have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Over the years, a variety of different methods for actuating the cutting and staple deployment components have been developed. For example, U.S. Pat. No. 6,978,921 to Shelton, IV et al. discloses a surgical stapling instrument that employs tissue severing and staple deployment components that are driven through manual actuation of various trigger mechanisms on the handle. Other surgical stapling apparatuses have been developed that employ battery powered motors. Such a device is disclosed in U.S. Pat. No. 5,954,259 to Viola et al.

Still other surgical staplers are actuated by a source of pressurized gas. For example, U.S. Pat. No. 6,619,529 to Green et al. discloses a surgical stapler that employs a source of pressurized gas in the handle that is used to power a cylinder that is also located within the handle. The cylinder houses a piston assembly that is actuated by admission of the pressurized gas into the cylinder. The piston is configured to coact with components located in the elongated tube portion and handle member to cause the deployment of the staples and the surgical knife in the distally mounted end effector. Such design, however, employs a complex collection of components for transmitting the motion of the handle-mounted piston to the components located in the end effector portion of the device. In addition, when using such a device, there is a risk that the power source becomes depleted during the surgical procedure because there is no way of monitoring the amount of gas remaining in the gas cartridge. If this occurs during the firing or retraction cycles, such devices lack means for easily exchanging the spent container with a new container or auxiliary power source.

Another pneumatically powered surgical stapling device is disclosed in US Patent Publication No. US 2006/0151567 to Roy. This device employs a pneumatically powered motor or piston system supported in the handle of the device for creating a motion that is employed to actuate the end effector. This device may be powered by removable cartridges or from an external power source, such as the hospital's existing pneumatic air or gas supply.

Such pneumatically powered devices that employ cartridges or containers in the handle portion of the device are also hampered by the size of the gas cylinder required to store the pressurized gas at sufficient volumes to facilitate actuation of the device a desired number of times at a minimum usable pressure. In the past, devices designed for large numbers of applications/procedures would either require a large cylinder to be used or, if smaller cylinders were used, such cylinders would have undesirably high pressures. In addition, devices that employ removable cartridges that can be used an unlimited number of times must be reprocessed and resterilized. Such arrangements can dramatically change performance capabilities and may therefore be less desirable.

Other problems exist with prior pneumatically powered surgical apparatuses. For example, once the surgeon activates the instrument through a single switch or activation trigger, the instrument progresses through or at least attempts to complete the firing cycle. Thereafter, the firing components may be retracted by the drive system. Prior pneumatically actuated instruments also lack suitable electrical control mechanisms to control the actuated pneumatic components. Prior pneumatically actuated surgical apparatuses also lack suitable electrical recording capabilities to provide information associated with the pneumatically actuated surgical apparatus to the surgeon.

Consequently there is a need for a pneumatically powered and electrically controlled surgical stapling device that does not require the use of an extensive collection of components to transfer the pneumatically generated stapling and firing motions to the end effector components.

There is a need for a pneumatically powered instrument with electrical control mechanisms. Conventional pneumatically powered instruments employ pressurized gas to actuate cutting and/or stapling functions. Once the pneumatic cylinder is actuated, however, it is difficult to control the flow rate of the gas from the pneumatic cylinder or the pressurization of the pneumatic system. Thus, there is a need to integrate pneumatic actuators with one or more electrical control elements to control the rate of release of the pressurized gas from the pneumatic cylinder and thus control the pressurization of the pneumatic system. It also would be advantageous to employ the electrical control elements to control the release of the gas from the pneumatic cylinder at a variable rate.

There is another need for a pneumatically powered instrument with electrical recording capabilities. One reason for employing electrical recording capabilities is for the clinician to be able to verify via an endoscope that the desired location for the cut has been achieved, including a sufficient amount of tissue has been captured between opposing jaws. Otherwise, opposing jaws may be drawn too close together, especially pinching at their distal ends, and thus not effectively forming closed staples in the severed tissue. At the other extreme, an excessive amount of clamped tissue may cause binding and an incomplete firing. When endoscopic surgical instruments fail, they are often returned to the manufacturer, or other entity, for analysis of the failure. If the failure resulted in a critical class of defect in the instrument, it is necessary for the manufacturer to determine the cause of the failure and determine whether a design change is required. In that case, the manufacturer may spend many hundreds of man-hours analyzing a failed instrument and attempting to reconstruct the conditions under which it failed based only on the damage to the instrument. It can be expensive and very challenging to analyze instrument failures in this way. Also, many of these analyses simply conclude that the failure was due to improper use of the instrument. Thus, there is a need for a pneumatically powered instrument that employs a number of sensors and electrical recording elements to selectively discharge the activation of the pneumatic cylinder and/or to selectively pressurize the pneumatic system and record any condition of the instrument based on readings from the sensors.

There is a further need for a pneumatically powered instrument with electrical feedback capabilities. Once the instrument closes upon tissue before firing, electrical feedback enables the clinician to verify via an endoscope that the desired location for the cut has been achieved, including a sufficient amount of tissue has been captured between opposing jaws.

Otherwise, opposing jaws may be drawn too close together, especially pinching at their distal ends, and thus not effectively forming closed staples in the severed tissue. At the other extreme, an excessive amount of clamped tissue may cause binding and an incomplete firing.

Endoscopic staplers/cutters continue to increase in complexity and function with each generation. One of the main reasons for this is the quest for lower force-to-fire (FTF) to a level that all or a great majority of surgeons can handle. Surgeons typically prefer to experience proportionate force distribution to that being experienced by the end-effector in the forming the staple to assure them that the cutting/stapling cycle is complete, with the upper limit within the capabilities of most surgeons (usually around 15-30 lbs). They also typically want to maintain control of deploying the staple and being able to stop at anytime if the forces felt in the handle of the device feel too great or for some other clinical reason. These user-feedback effects are not suitably realizable in present pneumatically powered instruments. As a result, there is a general lack of acceptance by physicians of pneumatically powered instruments where the cutting/stapling operation is actuated by merely pressing a button.

With current surgical instruments, the status of the instrument is generally not provided to a user (clinician) of the surgical instrument during a procedure. For example, with current mechanical endocutters, the presence of the staple cartridge, the position of the knife, the time elapsed since clamping, and the magnitude of the firing force are generally not provided to the user. Without visual and/or audible feedback, each user must rely on his or her own "feel" to determine the status of the surgical instrument, thereby creating inefficiencies, inconsistencies, and potential damage to the surgical instrument.

SUMMARY

One embodiment provides a status module for use with a pneumatically powered surgical instrument comprising a plurality of sensors. The status module comprises a housing structured and arranged to releasably connect to the pneumatically powered surgical instrument. At least one contact, wherein an individual contact is structured and arranged to be in electrical communication with a different sensor when the housing is connected to the pneumatically powered surgical instrument. The least one sensor is fluidically coupled to the pneumatically powered surgical instrument. A circuit is in electrical communication with the least one contact and at least one indicator. The least one indicator is in electrical communication with the circuit.

DRAWINGS

Various embodiments of a surgical apparatus, system, and method are described herein by way of example in conjunction with the following figures, wherein like numerals may be used to describe like parts and wherein:

FIG. 12 is a side view of another knife bar and firing drive member arrangement of the surgical cutting and fastening instrument with the knife bar being retracted into a cylinder assembly shown in cross-section;

FIG. 13 is another side view of the knife bar and cylinder arrangements depicted in FIG. 12 with the knife bar in the extended position;

FIG. 14 is a top view of an end effector and spine assembly arrangement housing the cylinder and knife bar arrangements depicted in FIGS. 12 and 13;

FIG. 15 is a cross-sectional side elevational view of the end effector and spine assembly arrangement depicted in FIG. 14 with the anvil portion attached thereto and in the open position;

FIG. 17 is a top view of another knife bar and spine assembly arrangement that supports another firing drive member in the form of a bellows assembly of another embodiment of the surgical cutting and fastening instrument;

FIG. 18 is a cross-sectional side elevational view of the end effector and spine assembly arrangements of the embodiment depicted in FIG. 17;

FIG. 19 is a partial cross-sectional assembly view of a bellows assembly of the embodiments depicted in FIGS. 17 and 18;

FIG. 20 is an enlarged view of a portion of the bellows assembly of FIG. 19;

FIG. 27 illustrates one embodiment of an anvil closure sensor.

FIG. 28 illustrates one embodiment of a knife position sensor that is suitable for use with the pneumatically actuated piston bar portion protruding from the knife assembly.

FIG. 32 shows one embodiment of a memory map from the memory device.

DETAILED DESCRIPTION

Figure 1:
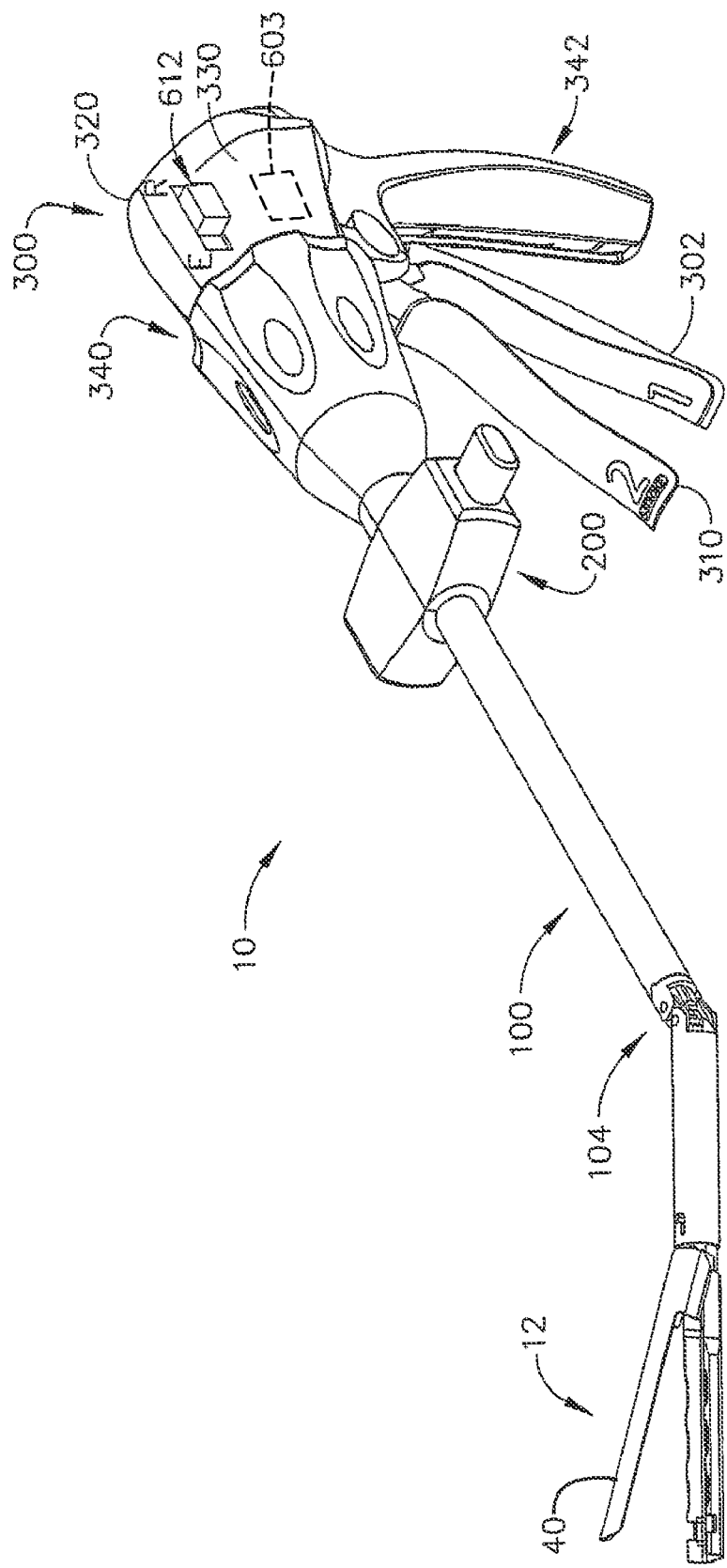
FIG. 1 is a perspective view of an embodiment of a surgical cutting and fastening instrument.

In one embodiment, a pneumatically powered instrument comprises an integrated pneumatic actuation system and electrical control, recording, and/or feedback elements. In one embodiment, a pneumatic actuation system is combined with an electrical control system to pneumatically actuate the instrument and electrically control the flow rate in the pneumatic system. An actuator may be employed to electrically control the pressurization of the pneumatic system. The control system receives pressurized gas from a source and produces an electrical output to actuate an element of the instrument employing at least one electrical component or element. The control system may be employed to control elements of a surgical cutting and fastening device. The cutting and fastening elements are pneumatically operable by a controller. Thus, the actuation of a pneumatic cylinder may be controlled with a pressurized gas and a controller. The controller controls the rate at which the pressurized gas is released within the pneumatic system. The controller may be employed to control one or more flow control elements such as solenoids, piezoelectric actuators, or electric motors. These flow control elements may be employed to open and close valves and other closure mechanisms to control the rate of discharge of the pressurized gas into the actuation cylinder. Additional flow control elements may be employed to release the pressurized gas at a variable rate. The embodiments are not limited in this context.

In another embodiment, a pneumatically powered instrument comprises electrical recording capabilities. The instrument may comprise an information recording system including, for example, a battery, circuit element, and memory device integrated with the pneumatically powered instrument. The information recording system may be employed to record information associated with the instrument. The instrument may comprise a switch, trigger, actuator, or other elements or techniques to selectively discharge a pressurized pneumatic gas to actuate the instrument. In one embodiment, the instrument may further comprise one or more sensors to enhance the information gathered by the recording system. Various sensors may be employed to provide information to the information recording system. The sensors include sensors to measure and/or record the number of actuations and reprocessings, the force to actuate or close an end effector of the instrument, the clamping force of the end effector, the pressure exerted on tissue, whether a cartridge is loaded in the instrument, the status of the cartridge, the lockout status of the instrument, the pressure in the pneumatic actuation cylinder, whether the surgical instrument is ready-to-fire, and so forth. The embodiments are not limited in this context.

In another embodiment, a pneumatically powered instrument comprises electrical feedback capabilities. The pneumatically powered instrument may be integrated with a feedback module. The feedback module may be self contained and adapted to connect to a plurality of contacts disposed throughout the instrument, an electrical circuit element, and a plurality of indicators. The feedback system, indicators, sensors, and controls may be electrically powered. The instrument may comprise pneumatically powered or power-assisted surgical cutting and fastening device. The embodiments are not limited in this context.

Turning to the Drawings wherein like numerals denote like components throughout the several views, FIG. 1 depicts a surgical stapling and cutting instrument 10 that is capable of practicing several unique benefits. The embodiment illustrated in FIG. 1 includes a handle assembly 300, an elongate shaft assembly 100, and an end effector 12 that is connected to the elongate shaft assembly 100. Various embodiments of the surgical apparatus may include an end effector that is pivotally attached to the elongate shaft assembly 100 and pivotally driven by bending cables or bands such as those disclosed in U.S. patent application Ser. No. 11/329,020, filed Jan. 10, 2006, entitled "SURGICAL INSTRUMENT HAVING AN ARTICULATING END EFFECTOR", the disclosure of which is herein incorporated by reference. However, as the present Detailed Description proceeds, those of ordinary skill in the art will appreciate that the various embodiments of the surgical apparatus described herein may be successfully practiced in connection with end effector arrangements that employ different pivoting mechanisms and controls and, as will be explained in further detail below, may even be successfully employed with non-articulating end effector arrangements.

As can be seen in FIG. 1, the handle assembly 300 of the instrument 10 may include a closure trigger 302 and a firing trigger 310. It will be appreciated that instruments having end effectors directed to different surgical tasks may have different numbers or types of triggers or other suitable controls for operating an end effector. The end effector 12 is shown separated from the handle assembly 300 by the preferably elongate shaft assembly 100. A clinician may articulate the end effector 12 relative to the shaft assembly 100 by utilizing an articulation control 200.

In various embodiments, multiple sensors may be coupled to elements in the hand assembly 300, the elongate shaft assembly 100, and/or the end effector 12 to measure and control various functions of the instrument 10, record the status of various components of the instrument, and provide the clinician or user with feedback indications. The instrument 10 comprises a plurality of sensors), wherein the plurality of sensors includes, for example, a closure trigger sensor, an anvil closure sensor, an anvil closure load sensor, a knife position sensor, a cartridge present sensor, a cartridge condition sensor, a firing trigger sensor, and a valve actuation sensor, or any combination thereof. Other sensors may comprise an articulation angle sensor, an anvil position sensor, a firing force sensor, a lockout condition sensor, a pneumatic pressure sensor, a flow rate sensor, or any combination thereof. Each sensor may be in electrical communication with a different contact positioned proximate the exterior of the surgical instrument 10. Sensors may be coupled to the closure trigger 302 and the firing trigger 310 to detect their operation. Sensors may be employed to measure the anvil 40 closure and the closure load on the anvil 40. Other sensors may be employed to measure the position of the knife assembly 30 (FIG. 2), the presence of the staple cartridge 50 (FIG. 2) and/or the status of the staple cartridge 50 (e.g., spent or un-spent). Other sensors may be employed throughout the instrument 10 to determine the number of actuations of instrument 10, the pressure in the pneumatic system, pressure of the pneumatic cylinder or actuation cylinder, variable rate sensors to activate valve actuators and the like. The embodiment, however, are not limited in this context.

The sensor output signals $S_1$ to $S_n$, where n is any positive integer, are provided to an electronic control module 603 located in the handle assembly, for example. The electronic control module 603 comprises a controller, a memory device, a battery, a measurement circuit, and/or an actuator to control a closure mechanism portion of an electrically controlled variable rate pneumatic valve as described hereinbelow. The embodiment, however, are not limited in this context.

It should be appreciated that spatial terms such as vertical, horizontal, right, left etc., are given herein with reference to the figures assuming that the longitudinal axis of the surgical instrument 10 is co-axial to the central axis of the elongate shaft assembly 100, with the triggers 302, 310 extending downwardly at an acute angle from the bottom of the handle assembly 300. In actual practice, however, the surgical instrument 10 may be oriented at various angles and, as such, these spatial terms are used relative to the surgical instrument 10 itself. Further, "proximal" is used to denote a perspective of a clinician who is behind the handle assembly 300 who places the end effector 12 distal, or away from him or herself.

As used herein, the term, "pressurized gas" refers to any gas suitable for use in pneumatically powered systems employed in a sterile environment. Non-limiting examples of such mediums include compressed air, carbon dioxide ($CO_2$), Nitrogen, Oxygen, Argon, Helium, Sodium Hydride, Propane, Isobutane, Butane Chlorofluorocarbons, Dimethyl ether. Methyl ethyl ether, Nitrous Oxide, Hyrdofluoroalkanes (HFA)—either, for example, HFA 134a (1,1,1,2,-tetrafluoroethane) or HFA 227 (1,1,1,2,3,3,3-heptafluoropropane).

As used herein, the term "fluidically coupled" means that the elements are coupled together with an appropriate line or other means to permit the passage of pressurized gas therebetween. As used herein, the term "line" as used in "supply line" or "return line" refers to an appropriate passage formed from rigid or flexible conduit, pipe and/or tubing for transporting pressurized gas from one component to another.

As used herein the terms "pneumatic signal" or "pneumatic drive signal" refer to the flow of gas from a source of pressurized gas to one or more components that are fluidically coupled to the source of pressurized gas or the flow of gas between components that are fluidically coupled together.

As used herein, the phrase, "substantially transverse to the longitudinal axis" where the "longitudinal axis" is the axis of the shaft, refers to a direction that is nearly perpendicular to the longitudinal axis. It will be appreciated, however, that directions that deviate some from perpendicular to the longitudinal axis are also substantially transverse to the longitudinal axis.

Figure 2:
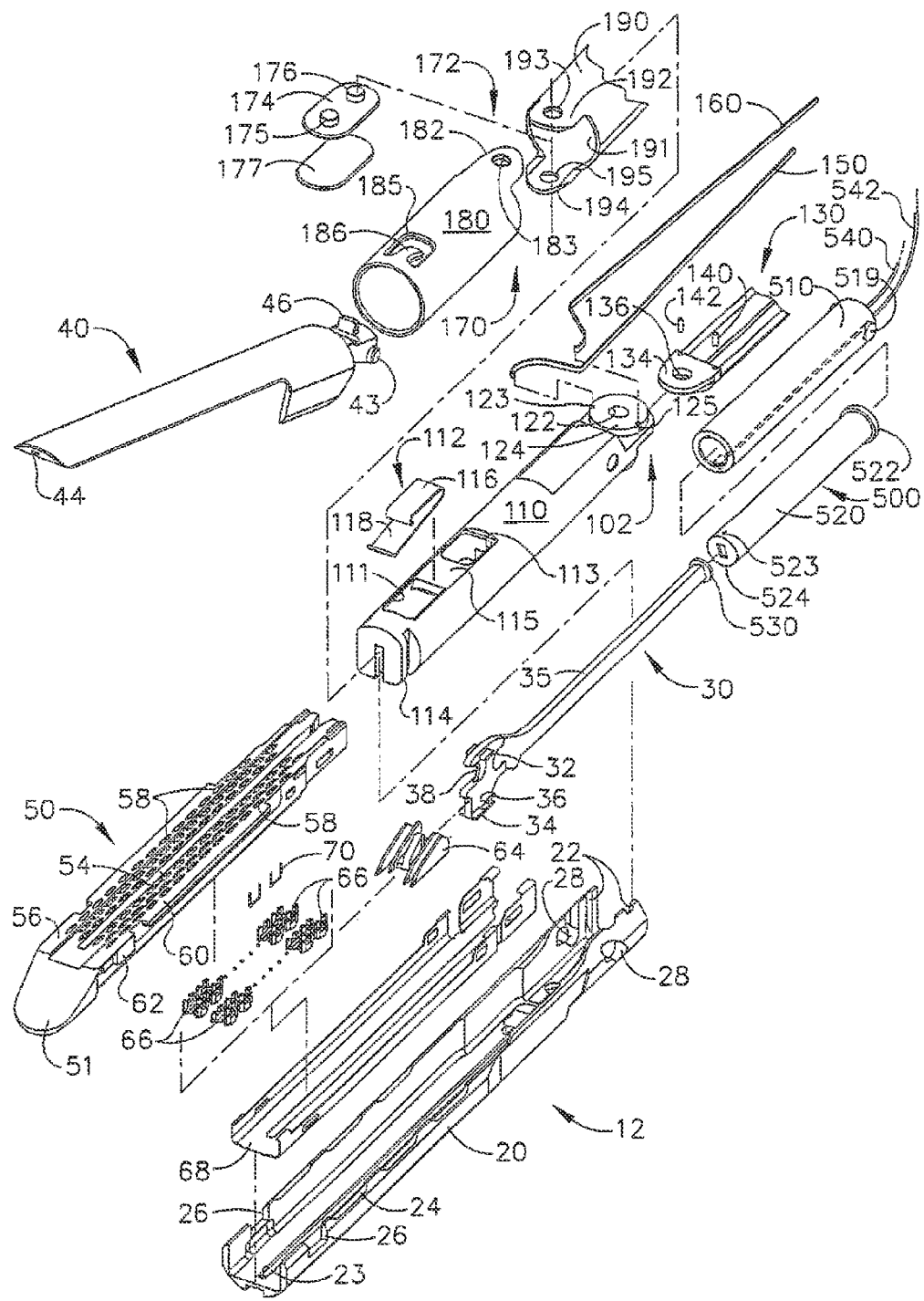
FIG. 2 is an exploded assembly view of an embodiment of an end effector arrangement that may be employed in connection with various embodiments of the surgical cutting and fastening instrument.

FIG. 2 illustrates an exploded assembly view of one type of pneumatically actuated and electrically controlled tool assembly or end effector that may be employed in various embodiments of the surgical instrument 10. The pneumatically operated actuated and electrically controlled assembly 12 shown in FIGS. 1-4 is configured to act as an endocutter. As the present Detailed Description proceeds, however, it will be appreciated that various unique and novel drive arrangements of embodiments of the present invention could also be conceivably employed to drive other end effectors configured to perform other surgical tasks and thus requiring the removal, modification, or addition of components from what is shown in the Figures. Also, it will be appreciated that the end effectors 12 shown in FIGS. 1-4 may be customized for specific surgical applications.

One type of end effector that may be employed with various embodiments of the surgical instrument 10 is depicted in FIG. 2. As can be seen in that Figure, the end effector 12 employs an E-beam firing mechanism ("knife assembly") 30 that, in addition to cutting tissue and firing staples located in a staple cylinder seated therein, advantageously controls the spacing of an anvil 40 portion of the end effector 12 relative to the staple cylinder. Various aspects of E-beam firing mechanisms are described in U.S. Pat. No. 6,978,921, entitled Surgical Stapling Instrument Incorporating An E-Beam Firing Mechanism to Shelton, IV. et al., the relevant portions of which are herein incorporated by reference. As the present Detailed Description proceeds, however, those of ordinary skill in the art will appreciate that other knife and firing mechanism configurations may be advantageously employed without departing from the overall scope of the embodiments.

As used herein, the term "firing mechanism" refers to the portion or portions of the pneumatically actuated and electrically controlled tool and/or end effector that move from an unactuated position wherein the firing mechanism may be essentially at rest to an actuated or end position wherein that portion or portions have been moved or repositioned to a final position wherein such movement thereof resulted in the tool completing one or more actions in response to the application of at least one firing motion thereto. The firing mechanism may comprise, for example: (i) components that are completely supported by the pneumatically actuated and electrically controlled tool and interface with components in the surgical apparatus; (ii) a combination of components that are located in the pneumatically powered tool and in the surgical apparatus; or (ii) components that are supported by the surgical apparatus and are movable into and out of the pneumatically actuated and electrically controlled tool. As used herein, the term "firing stroke" refers to the actual movement of the firing mechanism from the unactuated position to the actuated position. The term "retraction stroke" refers to the return movement of the firing mechanism from the actuated position to the unactuated position.

As can be seen in FIG. 2, the end effector 12 includes a distal member that, in various non-limiting embodiments, comprise an elongate channel 20 that has a pivotally translatable anvil 40 attached thereto. The elongate channel 20 is configured to receive and support a staple cartridge 50 that is responsive to the knife assembly 30 to drive staples 70 into forming contact with the anvil 40. It will be appreciated that, although a readily replaceable staple cartridge is advantageously described herein, a staple cartridge consistent with aspects of the present invention may be permanently affixed or integral to the elongate channel 20.

In various embodiments, the firing mechanism or knife assembly 30 includes vertically spaced pins that control the spacing of the end effector 12 during firing. In particular, upper pins 32 are staged to enter an anvil pocket 42 near the pivot between the anvil 40 and elongate channel 20. See FIG. 4. When fired with the anvil 40 closed, the upper pins 32 advance distally within a longitudinal anvil slot 44 extending distally through anvil 40. Any minor upward deflection in the anvil 40 is overcome by a downward force imparted by the upper pins 32.

Knife assembly 30 also includes a knife bar cap 34 that upwardly engages a channel slot 23 formed in the elongate channel 20, thereby cooperating with the upper pins 32 to draw the anvil 40 and the elongate channel 20 slightly closer together in the event of excess tissue clamped therebetween. In various embodiments, the knife assembly 30 may advantageously include middle pins 36 that pass through a firing drive slot (not shown) formed in a lower surface of the cartridge 50 and an upward surface of the elongate channel 20, thereby driving the staples 70 therein as described below. The middle pins 36, by sliding against the elongate channel 20, advantageously resist any tendency for the end effector 12 to be pinched shut at its distal end. However, the unique and novel aspects of various embodiments of the present invention may be attained through use of other knife assembly arrangements.

A distally presented cutting edge 38 between the upper and middle pins 32, 36 on the knife assembly 30 traverses through a proximally presented, vertical slot 54 in the cartridge 50 to sever clamped tissue. The affirmative positioning of the knife assembly 30 with regard to the elongate channel 20 and anvil 40 assure that an effective cut is performed. In various embodiments, the lower surface of the anvil 40 may be provided with a plurality of staple forming pockets therein (not shown) that are arrayed to correspond to a plurality of staple apertures 58 in an upper surface 56 of the staple cartridge 50 when the staple cartridge 50 is received within the elongate channel. In various embodiments, the staple cartridge 50 may be snap fit into the elongate channel 20. Specifically, extension features 60, 62 of the staple cartridge 50 frictionally and releasably engage recesses 24, 26, respectively of the elongate channel 20.

As can also be seen in FIG. 2, the staple cartridge 50 comprises a cartridge body 51, a wedge sled 64, staple drivers 66, staples 70, and a cartridge tray 68. When assembled, the cartridge tray 68 holds the wedge sled 64, staple drivers 66, and staples 70 inside the cartridge body 51. The elongate channel 20 is coupled to the handle assembly 300 by the elongate shaft assembly 100 which includes a distal spine or frame section 110 and a proximal spine or frame section 130. The elongate channel 20 has proximally placed attachment cavities 22 that each receives a corresponding channel anchoring member 114 formed on the distal end of the distal spine section 110. The elongate channel 20 also has anvil cam slots 28 that pivotally receive a corresponding anvil pivot 43 on the anvil 40. A closure sleeve assembly 170 is received over the spine assembly 102 and includes distal closure tube segment 180 and a proximal closure tube segment 190. As will be discussed below, axial movement of the closure sleeve assembly 170 relative to the spine assembly 102 causes the anvil 40 to pivot relative to the elongate channel 20.

As can be seen in FIG. 2, a locking spring 112 is mounted in the distal spine segment 110 as a lockout for the knife assembly 30. Distal and proximal square apertures 111, 113 are formed on top of the distal spine segment 110 to define a clip bar 115 therebetween that receives a top arm 116 of the locking spring 112 whose lower, distally extended arm 118 asserts a downward force on a distal end of a cylinder assembly 501 supporting the piston bar portion 35 protruding from the knife assembly 30 as will be discussed in further detail below. It will be appreciated that various embodiments may include other types of lockouts or no lockouts at all.

In the embodiment depicted in FIGS. 1-6, the end effector 12 may be articulated relative to the proximal closure tube segment 190 (and handle assembly 300) by a collection of cables or bands that are bent to pull the end effector 12 about a pivot 104. Those of ordinary skill in the art will understand that such arrangement represents just one of many articulation arrangements that may be employed in connection with these types of devices. In this embodiment, the proximal end of the distal spine segment 110 has a boss 122 thereon. The distal end of the proximal spine segment 130 is provided with a tang 134 that has an aperture 136 therethrough. The proximal spine segment 130 is positioned relative to the distal spine segment 110 such that the aperture 136 is coaxially aligned with an aperture 124 in boss 122 to enable a pivot pin 138 to extend therethrough. See FIG. 4. Such arrangement, when assembled, permits the end effector 12 to pivot relative to the proximal spine segment 130 about pivot axis A-A.

Figure 3:
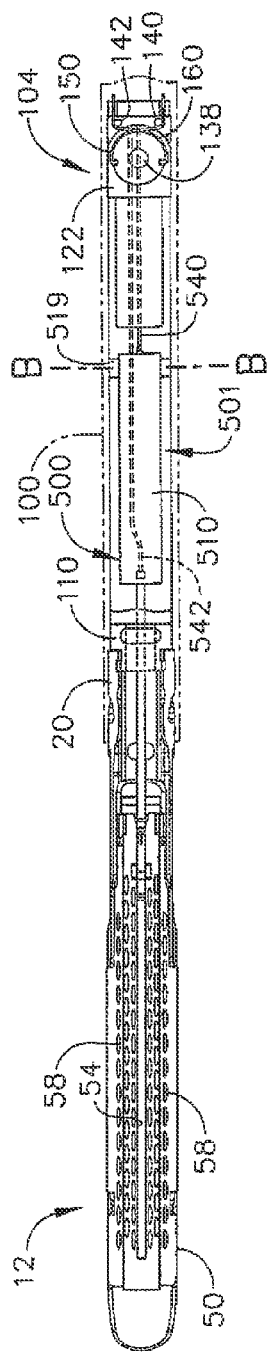
FIG. 3 is a top view of the end effector of FIGS. 1 and 2 with the anvil portion removed therefrom and the closure tube assembly illustrated in phantom lines.

As indicated above, this embodiment employs bands to articulate the end effector 12. In particular, the bands 150, 160 may extend distally toward the articulation pivot 104 as shown in FIGS. 2 and 3. Band 150 may extend through the proximal closure tube segment 190 along its left side where it is routed around band member 160 and across to the right side of the proximal closure tube segment 190. There, the band 150 may be mechanically coupled to boss 122, for example, at connection point 123. Likewise, band 160 may extend through the proximal closure tube segment 190 along its right side where it is routed around band member 150 and across to the left side of the proximal closure tube segment 190. There, band 160 may be mechanically coupled to the boss 122 at connection point 125.

Figure 4:
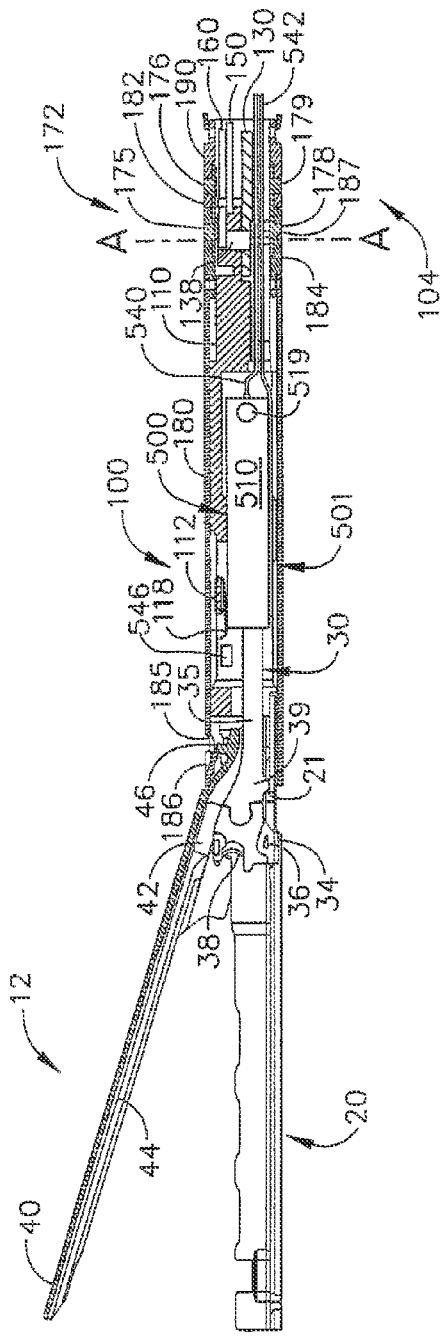
FIG. 4 is a cross-sectional side elevational view of the end effector arrangement of FIG. 3 with the anvil portion attached thereto and shown in an open position.

FIG. 3 is a top view of the end effector and spine assembly 102 with the closure tube assembly 100 depicted in phantom lines. FIG. 4 is a partial cross-sectional side view of the same portion of the instrument 10. As can be seen in FIG. 4, bands 150 and 160 are shown offset from one another to prevent interference in movement according to one non-limiting embodiment. For example, band 150 is shown at a lower position than band 160. In another non-limiting embodiment, the vertical positioning of bands 150 and 160 may be reversed. As can also be seen in FIGS. 2 and 3, the band member 150 extends around a pin 140 in the tang portion 134 of the proximal frame segment 130. Likewise, band 160 extends around pin 142 in the tang portion 134 of the proximal frame segment 130.

Figure 5:
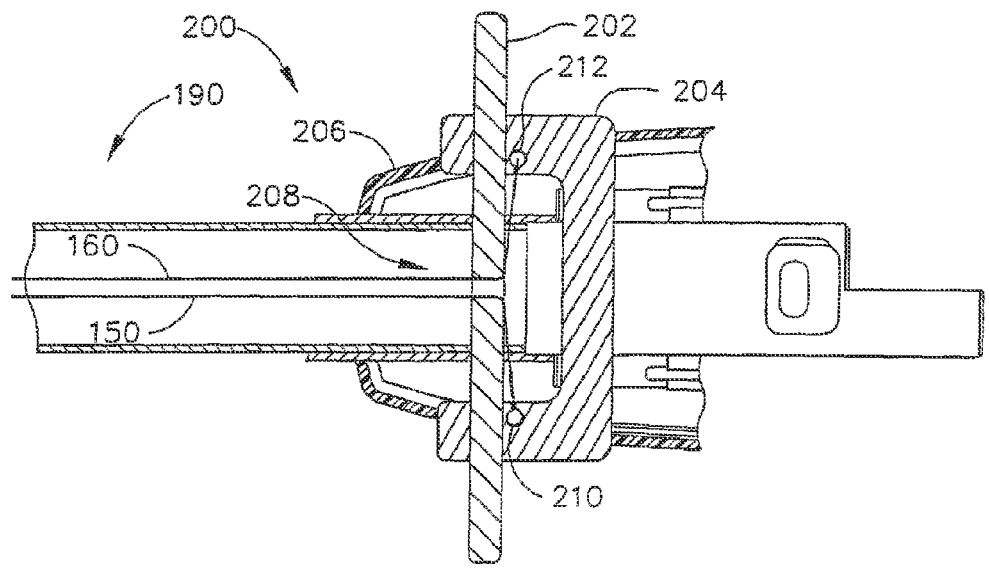
FIG. 5 is a cross-sectional top view of a portion of an articulation control that may be employed with various embodiments of the surgical cutting and fastening instrument.
Figure 8A:
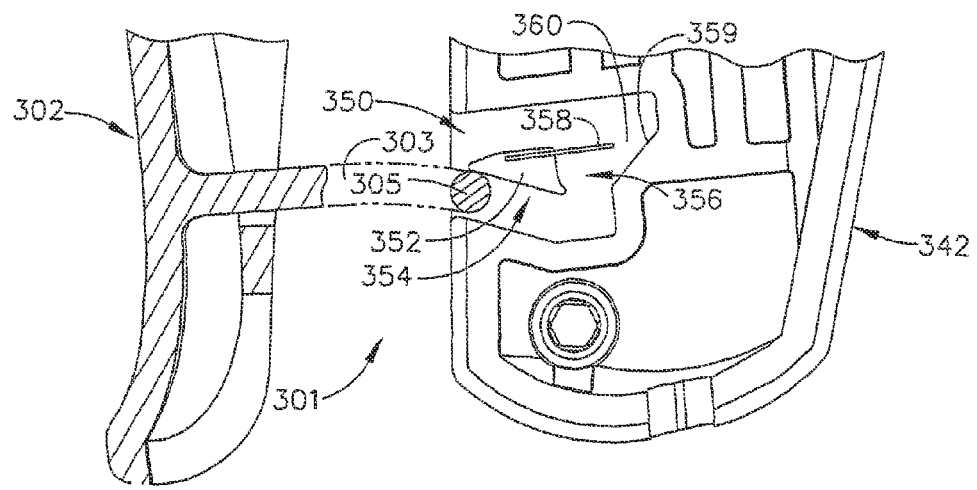
FIG. 8A is a partial cross-sectional view of a portion of a closure trigger locking system that may be employed in connection with various embodiments of the surgical cutting and fastening instrument.

Band portions 150 and 160 may extend from the boss 122 and along the proximal closure tube segment 190 to the articulation control 200, shown in FIG. 5. The articulation control 200 may include an articulation slide 202, a frame 204 and an enclosure 206. Band portions 150, 160 may pass through the articulation slide 202 by way of slot 208 or other aperture, although it will be appreciated that the band portions 150, 160 may be coupled to the slide 202 by any suitable means. The articulation slide 202 may be one piece, as shown in FIG. 5, or may in one non-limiting embodiment, include two pieces with an interface between the two pieces defining the slot 208. In one non-limiting embodiment, the articulation slide 202 may include multiple slots, for example, with each slot corresponding to one of band portions 150, 160. Enclosure 206 may cover the various components of the control 200 to prevent debris from entering.

In various embodiments, band portions 150, 160 may be anchored to the frame 204 at connection points 210, 212 proximally located from the slot 208. The non-limiting embodiment of FIG. 5 shows that the band portions 150, 160 are pre-bent from connection points 210, 212 to the slot 208 located near the longitudinal axis of the proximal closure tube segment 190. It will be appreciated that band portions 150, 160 may be anchored anywhere in the instrument 10 located proximally from the slot 208, including the handle assembly 300.

Figure 6:
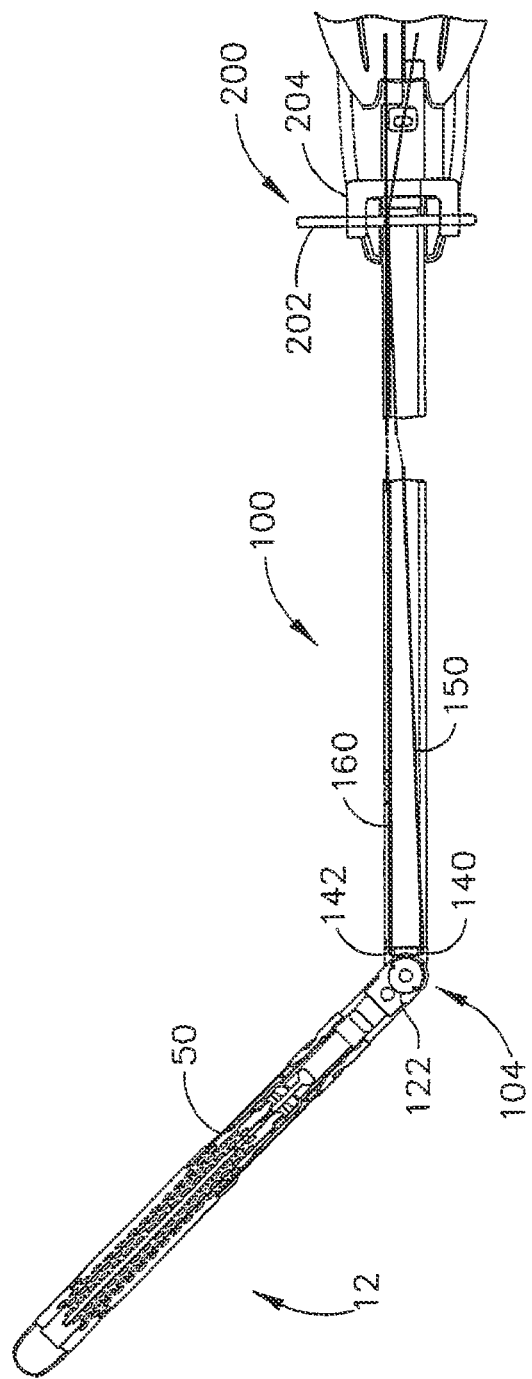
FIG. 6 is a top cross-sectional view illustrating the articulation of the end effector depicted in FIG. 1.

In use, the embodiment of FIG. 2 may have an unarticulated position as shown in FIG. 3. The articulation control 200 and bands 150, 160 are shown in a centered position roughly at the longitudinal axis of the shaft assembly 100. Accordingly, the end effector 12 is in a neutral or unarticulated position. In FIG. 6, the articulation control 200 is shown with the articulation slide 202 pushed through the articulation frame to the right side of the shaft assembly 100. Accordingly, bands 150, 160 are bent toward the right side of the shaft assembly 100. It can be seen that the bending of band 150 to the right exerts a laterally directed force on the boss 122 that is offset from the boss's 122 pivot point. This offset force causes the boss 122 to rotate about articulation pivot 104, in turn causing the end effector 12 to pivot to the right as shown. It will be appreciated that pushing the articulation slide 202 to the left side of the shaft assembly 100 may exert a laterally directed force on bands 150, 160, bending both bands 150, 160 toward the left side of the shaft assembly 100. The bending of band 160 then exerts a laterally directed force on boss 122, which as above, is offset from the boss's 122 pivot point. This, in turn, causes the boss 122 to rotate about the articulation pivot causing the end effector 12 to pivot to the left.

In various embodiments, the shaft assembly 100 is comprised of a closure tube assembly 170 that is received on the spine assembly 102. See FIG. 2. The closure tube assembly 170 comprises a distal closure tube segment 180 and a proximal closure tube segment 190. The distal closure tube segment 180 and the proximal closure tube segment 190 may be fabricated from a polymer or other suitable material. The proximal closure tube segment 190 is hollow and has an axial passage 191 extending therethrough that is sized to receive a portion of the spine assembly 102 therein.

In the embodiment depicted in FIGS. 2 and 4, a double pivot closure joint 172 is employed. It will be appreciated that the invention is not limited to a double pivot closure joint design and may include any suitable closure tube or sleeve, or no closure tube or sleeve at all. With particular reference to FIG. 4, the distal closure tube segment 180 has upper and lower proximally projecting tangs 182, 184. The distal closure tube segment 180 further includes a horseshoe aperture 185 and tab 186 for engaging the anvil open/closing tab 46 on the anvil 40 to cause the anvil 40 to pivot between open and closed positions as will be discussed in further detail below.

The proximal closure tube segment 190 is similarly provided with a distally extending upper tang 192 and a distally extending lower tang 194. An upper double pivot link 174 includes upwardly projecting distal and proximal pivot pins 175, 176 that engage respectively an upper distal pin hole 183 in the upper proximally projecting tang 182 and an upper proximal pin hole 193 in the upper distally projecting tang 192. The joint arrangement further includes a lower double pivot link 177 that has downwardly projecting distal and proximal pivot pins 178, 179 (not shown in FIG. 2, but see FIG. 4) that engage respectively a lower distal pin hole 187 in the lower proximally projecting tang 184 and a lower proximal pin hole 195 in the lower distally projecting tang 194.

In use, the closure tube assembly 170 is translated distally to close the anvil 40, for example, in response to the actuation of the closure trigger 302. The anvil 40 is closed by distally translating the closure tube assembly 170 on the spine assembly 102, causing the back of the horseshoe aperture 185 to strike the open/closing tab 46 on the anvil 40 and cause it to pivot to the closed position. To open the anvil 40, the closure tube assembly 170 is axially moved in the proximal direction on the spine assembly 102 causing the tab 186 to contact and push against the open/closing tab 46 to pivot the anvil 40 to the opened position. In one embodiment, a sensor may be located in the closure tube assembly 170 to measure the force asserted on the horseshoe aperture 185 to strike the open/closing tab 46 on the anvil 40 to cause it to pivot to the closed position and to maintain it in the closed position.

Figure 7:
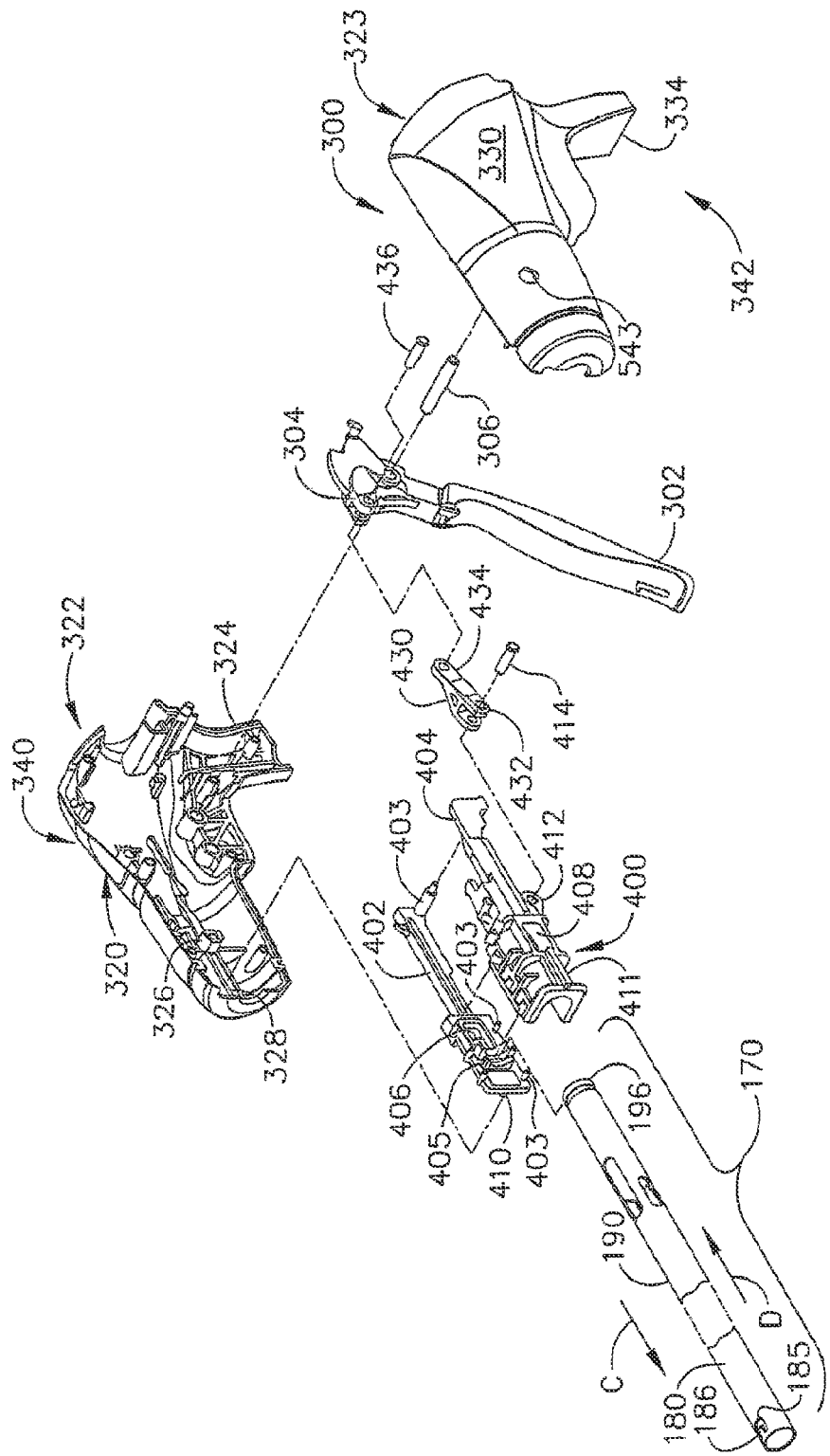
FIG. 7 is an exploded assembly view illustrating an embodiment of a closure tube assembly and shuttle arrangement supported within the handle assembly with other components housed within the housing assembly being omitted for clarity.

FIG. 7 illustrates an exploded assembly view of a non-limiting handle assembly 300 of various embodiments of the surgical apparatus. In the embodiment depicted in FIG. 7, the handle assembly has a "pistol grip" configuration and is formed from a right hand case member 320 and a left handed case member 330 that are molded or otherwise fabricated from a polymer or other suitable material and are designed to mate together. Such case members 320 and 330 may be attached together by snap features, pegs and sockets molded or otherwise formed therein by adhesive, screws, bolts and/or clips. The upper portion 322 of the right hand case member 320 mates with a corresponding upper portion 323 of the left hand case member 330 to form a primary housing portion designated as 340. Similarly, the lower grip portion 324 of the right hand case member 320 mates with the lower grip portion 334 of the left hand case member to form a grip portion generally designated as 342. In the embodiment depicted in FIG. 7, the entire grip portion 342 is integral with the primary housing portion 340. Such arrangement may be particularly well-suited for applications wherein a source of pressurized gas is permanently installed within the grip portion 342. Such arrangement is also suited for use with sources of pressurized gas that are external to the handle assembly 300 and plugged into the control components housed therein through a port or ports in the housing assembly. In other embodiments, as will be described in further detail below, the grip portion 342 is detachable from the primary housing portion 340. As will be appreciated as the present Detailed Description proceeds, such arrangement provides a myriad of benefits and advantages. Those of ordinary skill in the art will readily appreciate, however, that the handle assembly 300 may be provided in a variety of different shapes and sizes.

For the purposes of clarity, FIG. 7 only illustrates the components employed to control the axial movement of the closure tube assembly 170 which ultimately controls the opening and closing of the anvil 40. As can be seen in FIG. 7, a closure shuttle 400 that is coupled to the closure trigger 302 by a linkage assembly 430 is supported within the primary housing portion 340. Closure shuttle 400 may also be fabricated in two pieces 402, 404 that are molded or otherwise fabricated from a polymer or other suitable material and are designed to mate together. For example, in the embodiment illustrated in FIG. 7, the right hand portion 402 may be provided with fastener posts 403 that are designed to be received within corresponding sockets (not shown) in the left hand portion 404. The right and left hand portions 402, 404 may be otherwise retained together by snap members and/or adhesive and/or bolts, screws and/or clips. As can be seen in FIG. 7, a retention groove 196 is provided in the proximal end of the proximal closure tube segment 190. The right hand portion 402 of the closure shuttle 400 has a right retention flange segment 405 that is adapted to cooperate with a left retention flange segment (not shown) on the left hand portion 404 of the closure shuttle 400 to form a retention flange assembly that extends into the retention groove 196 in the proximal closure tube segment 190.

As also can be seen in FIG. 7, a right spine assembly retention peg 326 protrudes inward from the right hand case member 320. Such peg 326 protrudes into an elongated slot or window 406 in the right hand portion 402 of the closure shuttle 400. A similar closure shuttle retention peg (not shown) protrudes inward from the left hand case member 330 to be received in another window or slot 408 provided in the left hand side portion 404 of the closure shuttle 400. The retention pegs serve to non-movably affix the proximal end 133 of the proximal spine segment 130 (not shown in FIG. 7) to the handle assembly 300 while permitting the closure shuttle 400 to move axially relative thereto. The retention pegs may be mechanically attached to the proximal end of the proximal spine segment 130 by, for example, bolts, screws, adhesive, and/or snap features. In addition, the closure shuttle 400 is provided with laterally extending guide rails 410, 411. Rail 410 is configured to be slidably received within rail guide 328 the right hand case member 320 and rail 411 is configured to be slidably received within a rail guide (not shown) in left hand case member 330.

Axial movement of the closure shuttle 400 and closure tube assembly 170 in the distal direction (arrow "C") is created by moving the closure trigger 302 toward the grip portion 342 of the handle assembly 300 and axial movement of the closure shuttle 400 in the proximal direction (arrow "D") is created by moving the closure trigger 302 away from the grip portion 342. In various embodiments, the closure shuttle 400 is provided with a connector tab 412 that facilitates the attachment of the closure linkage assembly 430 thereto. See FIGS. 8 and 9. The closure linkage assembly 430 includes a yoke portion 432 that is pivotally pinned to the connector tab 412 by a pin 414. The closure linkage assembly 430 further has a closure arm 434 that is pivotally pinned to a yoke assembly 304 formed on the closure trigger 302 by a closure pin 436 as illustrated in FIG. 7. The closure trigger 302 is pivotally mounted within the handle assembly 300 by a pivot pin 306 that extends between the right hand case member 320 and the left hand case member 330.

When the clinician desires to close the anvil 40 to clamp tissue within the end effector 12, the clinician draws the closure trigger 302 toward the grip portion 342. As the clinician draws the closure trigger 302 toward the grip portion 342, the closure linkage assembly 430 moves the closure shuttle 400 in the distal "C" direction until the closure linkage assembly 430 moves into the locked position illustrated in FIG. 8. When in that position, the linkage assembly 430 will tend to retain the closure shuttle 400 in that locked position. As the closure shuttle 400 is moved to the locked position, the closure tube assembly 170 is moved distally on the spine assembly 102 causing the closure/opening tab 46 on the anvil 40 to be contacted by the proximal end of the horseshoe aperture 185 in the distal closure tube segment 180 to thereby pivot the anvil 40 to the closed (clamped) position.

In various embodiments, to further retain the closure shuttle 400 in the closed position, the closure trigger 302 may be provided with a releasable locking mechanism 301 that is adapted to engage the grip portion 342 and releasably retain the closure trigger 302 in the locked position. Other locking devices also may be used to releasably retain the closure shuttle 400 in the locked position. In the embodiment depicted in FIGS. 8, 8A, 8B, and 9, the closure trigger 302 includes a flexible longitudinal arm 303 that includes a lateral pin 305 extending therefrom. The arm 303 and pin 305 may be made from molded plastic, for example. The pistol grip portion 342 of the handle assembly 300 includes an opening 350 with a laterally extending wedge 352 disposed therein. When the closure trigger 302 is retracted, the pin 305 engages the wedge 352, and the pin 305 is forced downward (i.e., the arm 303 is rotated CW) by the lower surface 354 of the wedge 352. When the pin 305 fully passes the lower surface 354, the CW force on the arm 303 is removed, and the pin 305 is rotated CCW such that the pin 305 comes to rest in a notch 356 behind the wedge 352 thereby locking the closure trigger 302. The pin 305 is further held in place in the locked position by a flexible stop 358 extending from the wedge 352.

To unlock the closure trigger 302, the operator may further squeeze the closure trigger 302, causing the pin 305 to engage a sloped back wall 359 of the opening 350, forcing the pin 305 upward past the flexible stop 358. The pin 305 is then free to travel out an upper channel in the opening 360 such that the closure trigger 302 is no longer locked to the pistol grip portion 342. Further details of such arrangement may be found in U.S. patent application Ser. No. 11/344,020, filed Jan. 31, 2006 and entitled Surgical Instrument Having A Removable Battery to Shelton, IV et al., the relevant portions of which are herein incorporated by reference. Other releasable locking arrangements could also be employed.

Figure 10:
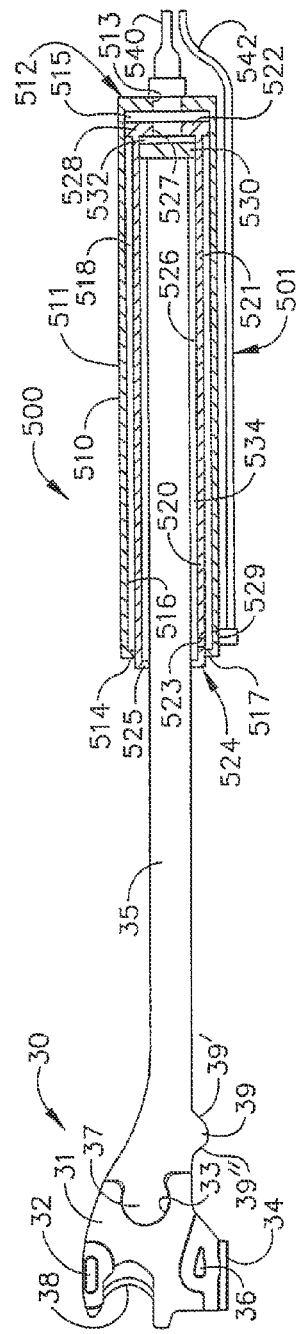
FIG. 10 is a side view of a knife bar arrangement and a firing drive member that comprises a two stage cylinder assembly of various embodiments of the surgical cutting and fastening instrument with the cylinder assembly shown in cross-section.
Figure 11:
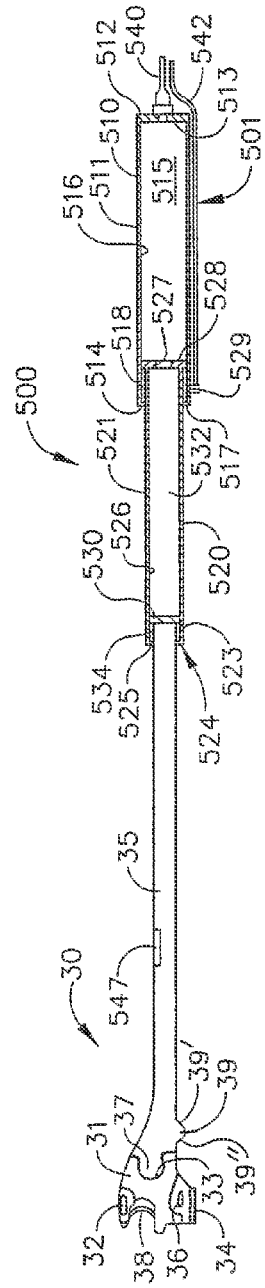
FIG. 11 is another side view of the knife bar and two stage cylinder arrangements depicted in FIG. 10 with the knife bar in the extended position.

In various embodiments of the surgical apparatus, the knife assembly 30 may have a substantially rigid piston bar portion 35 protruding therefrom or otherwise attached thereto that is part of a drive member 500 that is operably supported by the distal spine segment 110 and configured to apply at least two actuation motions (e.g., firing motion and retraction motion) to the knife assembly 30. In the embodiments depicted in FIGS. 3, 4, 10, and 11, the drive member 500 comprises a two stage pneumatically-actuated cylinder assembly 501. The knife assembly 30 may comprise a unitary component or it may be provided in multiple pieces to facilitate easier assembly of the instrument 10. For example, as shown in FIGS. 10 and 11, the knife bar assembly 30 comprises a distal portion 31 that contains the upper pins 32, the cap 34, the middle pins 36 and the knife 38. Distal portion 31 may be provided with an aperture 33 therein sized to receive a protrusion 37 provided on the distal end of the piston bar portion 35. The protrusion 37 may be frictionally received within the aperture 33 and/or retained therein by adhesive and/or welding.

The cylinder assembly 501 comprises a first cylinder housing 510 that has a first closed proximal end 512 and a first open distal end 514 that opens into a first axial passage 516 within the first cylinder housing 510. The cylinder assembly 501 also comprises a second cylinder housing 520 that has a second proximal end 522 and a second open distal end 524 that opens into a second axial passage 526. The second closed proximal end 522 has a first piston head 528 formed thereon that is sized relative to the first axial passage 516 to create a substantially airtight sliding seal with the first wall 511 of the first cylinder housing 510 to define a first cylinder area 515 between the distal side of the first proximal end 512 and the proximal side of the first piston head 528. The first distal end 514 of the first cylinder housing 510 further has an inwardly extending first flange 517 formed thereon for establishing a substantially airtight sliding seal with the outer wall surface of the second cylinder housing 520 to define a second cylinder area 518 between the proximal side of the first flange 517 and the distal side of the first piston head 528.

A first passage 527 is provided through the first piston head 528. As can also be seen in FIGS. 10 and 11, the proximal end of the piston bar 35 extends through the second open distal end 524 of the second cylinder housing 520 and into second axial passage 526. A second piston head 530 is formed on or otherwise attached to the proximal end of the piston bar 35. The second piston head 530 is sized relative to the second axial passage 526 to create a substantially airtight sliding seal with a second wall 521 of the second cylinder housing 520 to define a third cylinder area 532. The second distal end 524 of the second cylinder housing 520 further has an inwardly extending second flange 525 formed thereon for establishing a substantially airtight sliding seal with the piston bar 35 to define a fourth cylinder area 534 between the proximal side of the second flange 525 and the distal side of the second piston head 530.

As can be seen in FIGS. 3 and 4, the cylinder assembly 501 is mounted within the distal spine segment 110. In various embodiments, a pair of trunions 519 are provided on the proximal end of the first cylinder housing 510. The trunions 519 are received within trunion bores 119 in the distal spine segment 110 to enable the cylinder assembly 501 to pivot within the distal spine segment 110 about a pivot axis B-B. See FIG. 3. A first supply line or supply conduit 540 extends from a directional control valve 610 in the handle assembly 300 (FIGS. 8 and 9) through the proximal closure tube segment 190 to be coupled to the first proximal end 512 of the first cylinder housing 510 to supply pressurized gas through a first supply port 513 or opening in the first proximal end 512 of the first cylinder housing 510. See FIGS. 10 and 11. In one embodiment, a pressure sensor may be fluidically coupled to the first supply line 540 to measure or sense pressure (P) in the first supply line 540. The pressure sensor provides an electrical feedback signal to the electronic control module 603 that is proportional to the pressure in the first supply line 540. In addition, a second supply line 542 extends from the directional control valve 610 through the proximal closure tube segment 190 and is connected to the first cylinder housing 510 adjacent the distal end 514 thereof to supply pressurized gas into the second cylinder area 518 through a second port 529. In one embodiment, a pressure sensor may be fluidically coupled to the second supply line 542 to measure or sense pressure (P) in the second supply line 542. The pressure sensor provides an electrical feedback signal to the electronic control module 603 that is proportional to the pressure in the second supply line 542. Other pressure sensors may be fluidically coupled throughout the pneumatic system. For example, pressure sensors may be fluidically coupled to the respective first and second pressure supply ports 513, 529 to measure the pressure within the respective first and second cylinder areas 515, 518. In this manner, the pressure within the two stage cylinder assembly 501 may be measured and provided as a feedback signal to the electronic control module 603.

Figure 8:
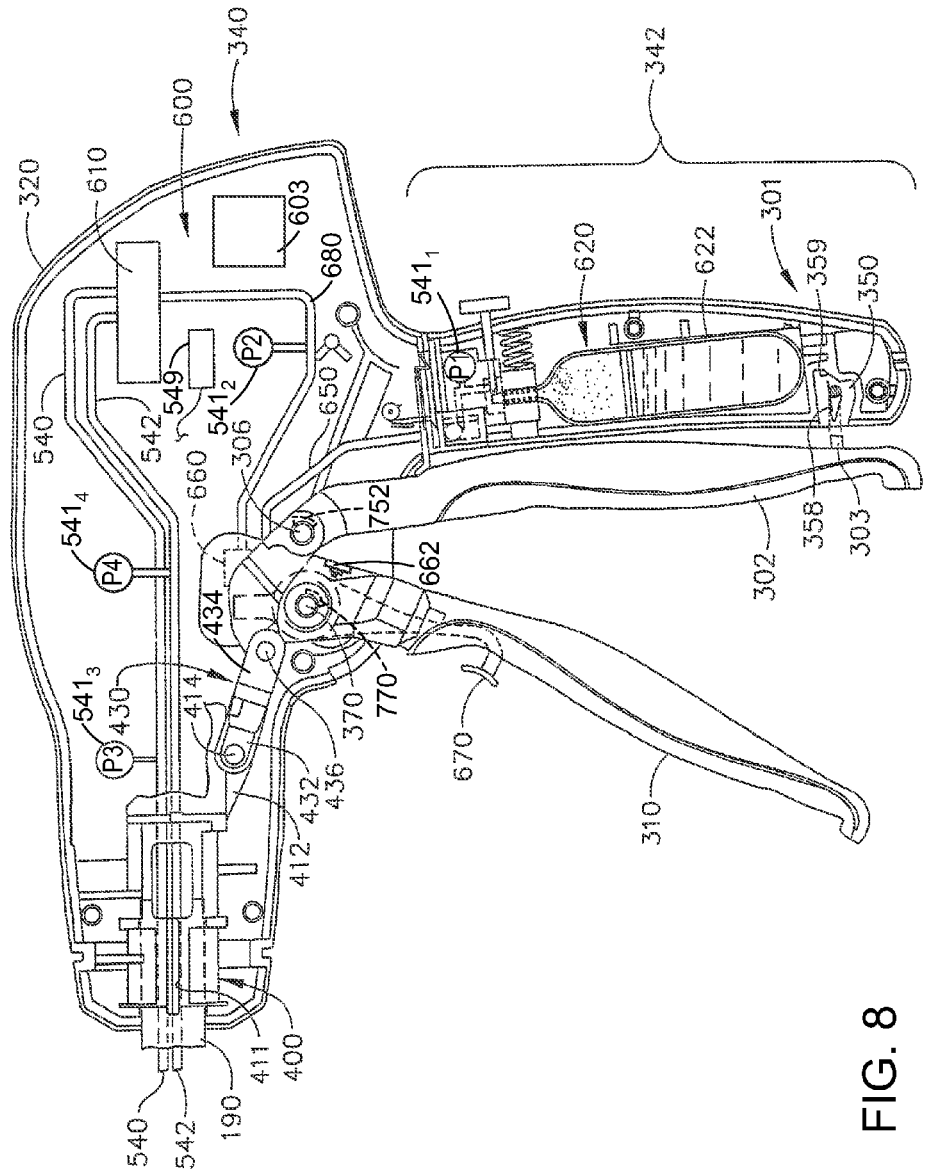
FIG. 8 is a cross-sectional view of a housing assembly arrangement of various embodiments of the surgical cutting and fastening instrument.
Figure 8B:
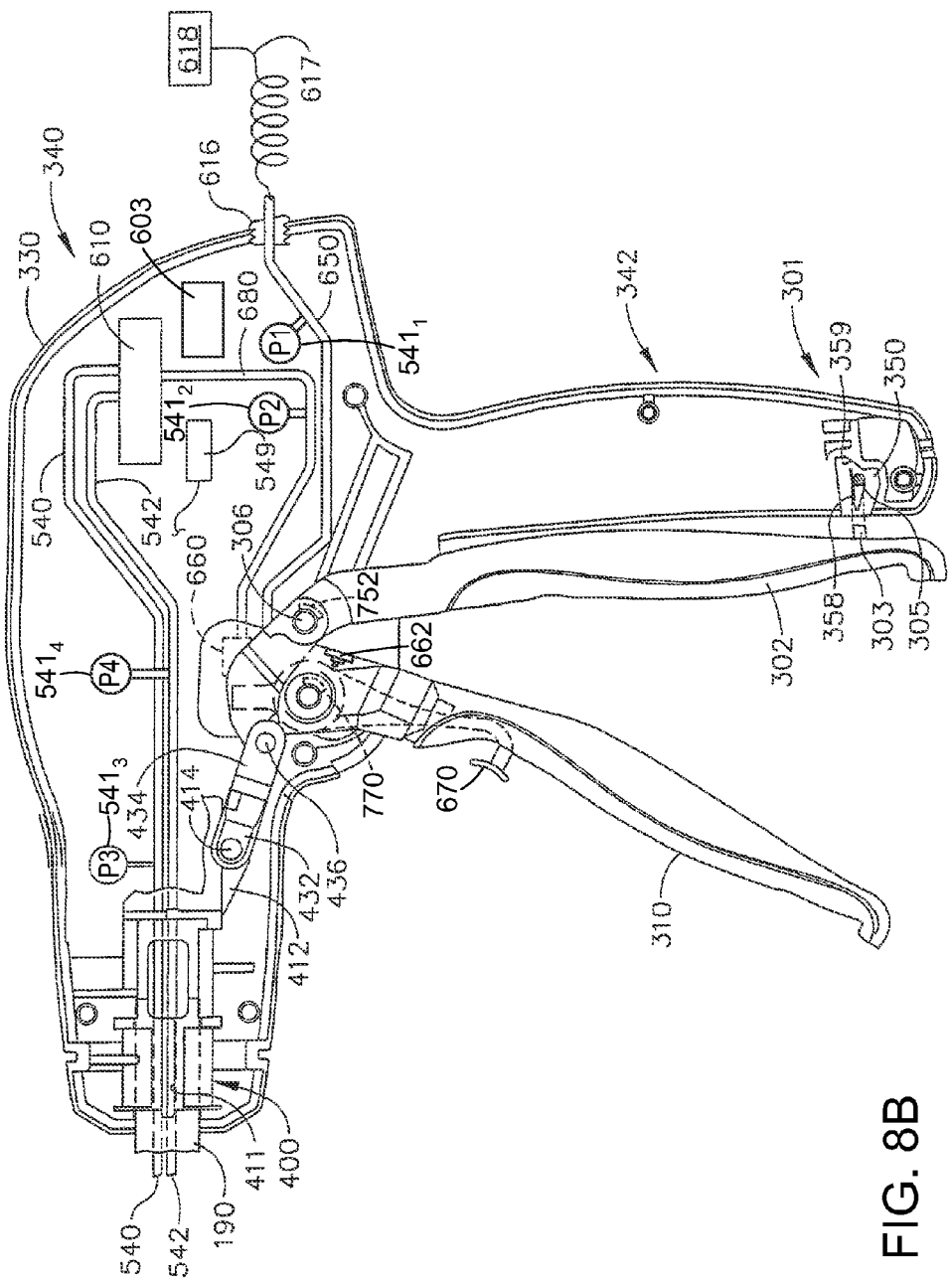
FIG. 8B is a cross-sectional view of another handle assembly embodiment of the surgical cutting and fastening instrument wherein the source of pressurized gas is external to the handle assembly.
Figure 9:
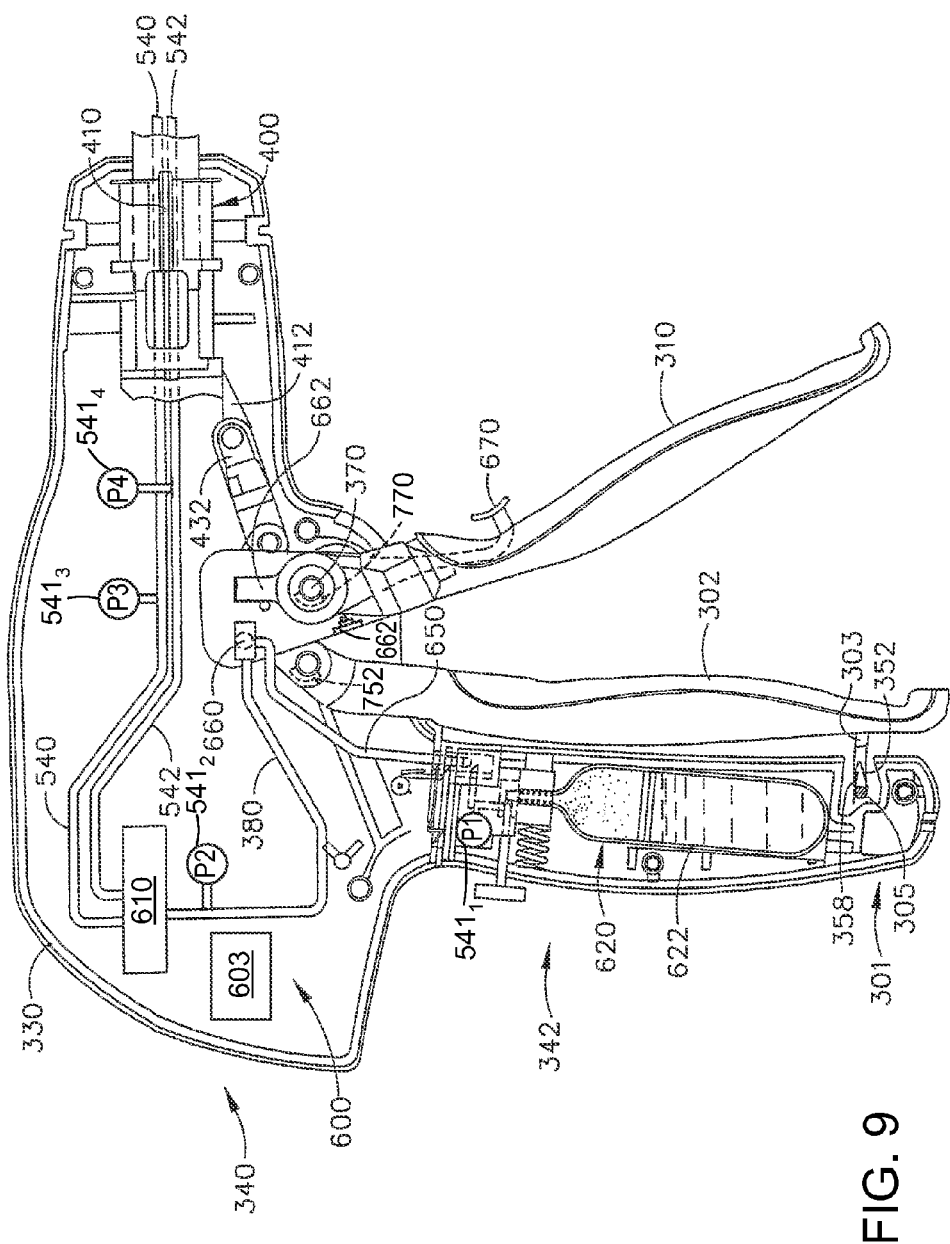
FIG. 9 is another cross-sectional view of the handle assembly of FIG. 8.

With reference to FIGS. 8-11 and 26, the extension and retraction of the firing mechanism or knife assembly 30 will now be explained. As can be seen in FIGS. 8 and 9, the supply lines 540 and 542 are coupled to an electrically controlled directional valve 610 which is part of an actuator system 600 housed within the handle housing 350. The actuator system 600 comprises an actuation trigger 670, a directional valve 610, and an electrically controlled variable flow rate pneumatic valve 660. These elements are coupled to the electronic control module 603. The electronic control module 603 receives feedback signals from various sensors distributed throughout the instrument 10. The electronic control module 603 provides control signals to various control elements distributed throughout the instrument 10 based on the feedback signals. In one embodiment, the electronic control module 603 comprises a controller 702, a memory device 703, a battery 704, a measurement circuit 732, and/or an actuator 706 to control a closure mechanism 730 portion of the electrically controlled variable flow rate pneumatic valve 660. See FIG. 26. The embodiments, however, are not limited in this context. In one embodiment, the actuator system 600 may be in communication with a status module 2408 (described below with reference to FIGS. 33-37). In various embodiments, the directional valve 610 may be electrically controlled by the electronic control module 603. IN other embodiments, the directional valve may be shifted manually between forward (extend) and reverse (retract) positions by a selector switch 612 or push buttons that are accessible through the handle housing 350. In one embodiment, the selector switch 612 or the appropriate button may be implemented in electrical form to generate a signal indicative of a desired state of the directional valve 610. The signal may be coupled to the controller 702, which generates a valve direction control signal to control the directional valve 610. In the embodiment depicted in FIGS. 8 and 9, a removable source 620 of pressurized gas is employed. As will be further discussed in detail below, such source of pressurized gas comprises a cylinder 622 that may be rechargeable with a preferred pressurized gas. Those of ordinary skill in the art will appreciate, however, that nonreplaceable/rechargeable sources (cylinders) of pressurized gas could also be effectively employed. Still in other embodiments, the handle assembly 300 may be provided with a port 616 for supplying pressurized gas from an external source 618 of pressurized gas. For example, the instrument 10 could be coupled to the facility's compressed air supply 618 through a flexible supply line 617. See FIG. 8B. In one embodiment, a pressure sensor may be fluidically coupled to an outlet port of the removable source 622 or a facility's compressed air supply 618 to measure or sense the pressure in an input supply line 650. The pressure sensor provides an electrical feedback signal to the electronic control module 603 that is proportional to the pressure in the input supply line 650.

The unique and novel aspects of the removable/rechargeable cylinder 622 will be discussed in further detail below. However, for the purpose of explaining the extension and retraction of the piston bar 35 and knife assembly 30, it can be seen that pressurized gas flows from the cylinder 622 (or external pressure source 618) through a supply line 650 into an electrically controlled variable flow rate pneumatic valve 660. The electrically controlled variable flow rate pneumatic valve 660 is controlled by the controller 702. As can most particularly be seen in FIG. 9, the variable flow rate pneumatic valve 660 is coupled to a valve actuation sensor 662 that is activated by an activation trigger 670. The valve actuation sensor 662 may be a digital or analog sensor that is coupled to the controller 702. In the illustrated embodiments, the valve actuation sensor 662 is a proportional sensor that provides an electrical signal that is proportional to the desired flow rate through the electrically controlled variable flow rate pneumatic valve 660. When the valve actuation sensor 662 detects the movement of the activation trigger 670, it sends an electrical signal to the controller 702 that is proportional to the desired flow rate of the pressurized gas flowing from the cylinder 622 into a supply line 680 to the first or second supply lines 540, 542. The controller 702 adjusts a flow control element within the variable flow rate pneumatic valve 660 to produce the desired flow rate of the pressurized gas. In one embodiment, a pressure sensor may be fluidically coupled to the supply line 680 to measure or sense the pressure in the supply line 680. The pressure sensor provides an electrical feedback signal to the electronic control module 603 that is proportional to the pressure in the supply line 680. As used herein, the term "variable flow rate actuation assembly" at least comprises the variable flow rate pneumatic valve 660, the activation trigger 670, the controller 702, the battery 704, and the actuator 706, and their respective equivalent structures.

The valve actuation sensor 662 (see FIGS. 22A, 22B) is in communication with the activation trigger 670 to detect when the activation trigger 670 has been drawn in (or "closed") toward the lower grip portion 324 of the handle by the operator to thereby pneumatically actuate the cutting/stapling operation by the end effector 12 in an electrically controlled manner. The valve actuation sensor 662 may be a proportional sensor such as, for example, a rheostat or variable resistor. When the activation trigger 670 is drawn in, the valve actuation sensor 662 detects the movement, and sends an electrical signal to the controller 702 and or the memory device 703 that is indicative of the desired pressure or flow rate through the pneumatic system. The controller 702 sends an electrical actuation signal to the actuator 706 to control the flow rate through the variable flow rate pneumatic valve 660. When the valve actuation sensor 662 is a variable resistor or the like, the actuation signal may be generally proportional to the amount of movement of the actuation trigger 670. That is, if the operator only draws or closes the actuation trigger 670 in a little bit, the actuation signal and hence the flow rate is relatively low. When the actuation trigger 670 is fully drawn in (or in the fully closed position), the actuation signal and hence the flow rate is at its maximum. In other words, the harder the user pulls on the actuation trigger 670, the greater the actuation signal causing greater flow rate through the variable flow rate pneumatic valve 660.

Figure 24:
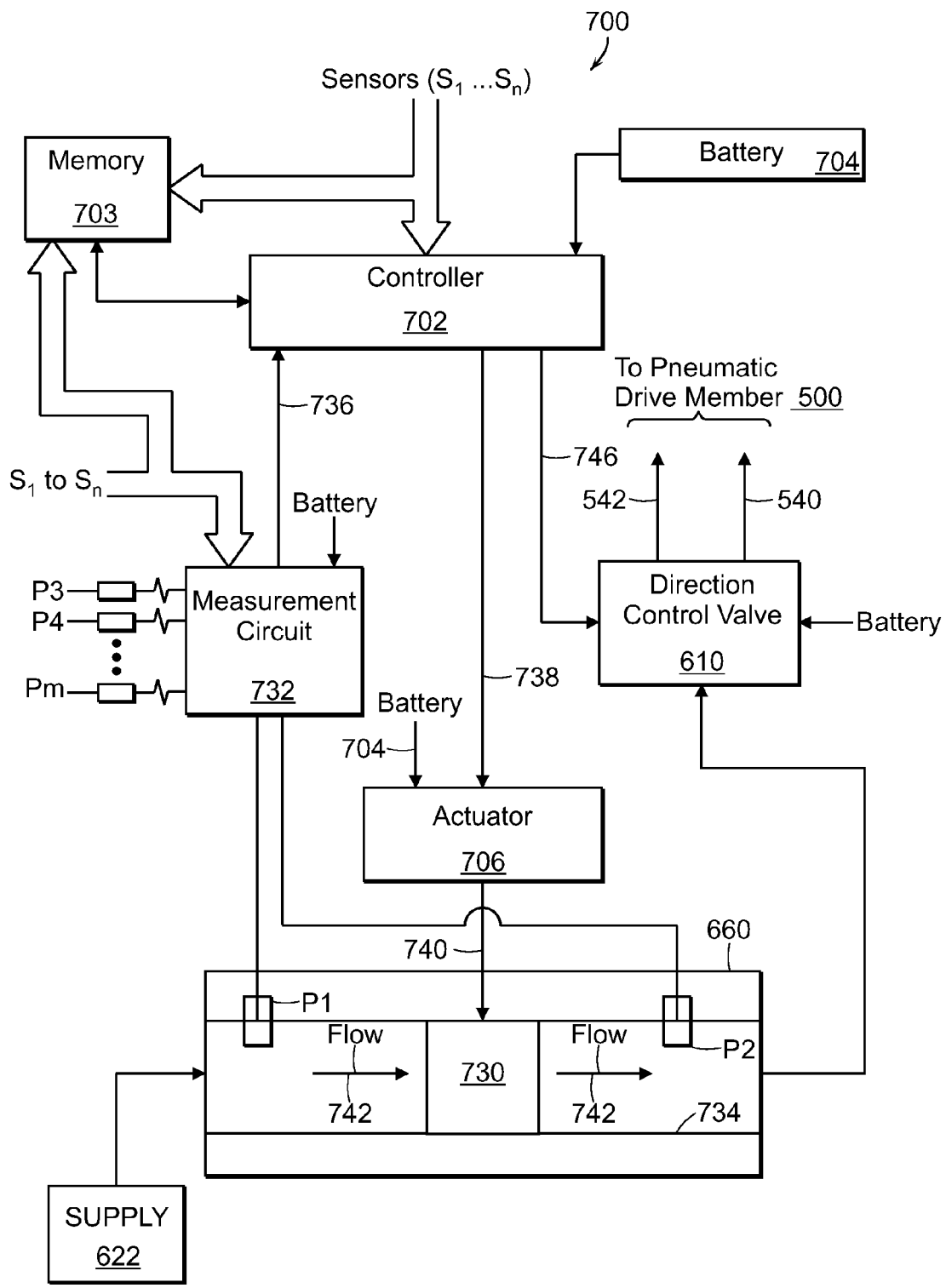
FIG. 24 illustrates one embodiment of an electrically controlled pneumatic system.

The actuator 706 may comprise any suitable type of actuation mechanism comprising electric motors, suitable gear reductions, a pneumatic actuator, solenoids, piezo-actuators, as well as any other suitable device capable of transforming a source of potential energy, such as electricity or compressed air, into physical displacement suitable for driving a closure mechanism 730 (FIG. 24).

Figure 22A:
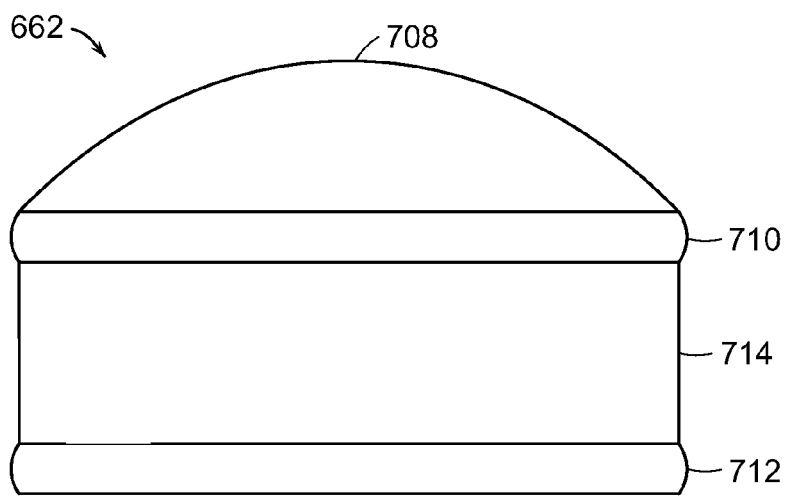
FIGS. 22A and 22B illustrate various embodiments of a proportional sensor.
Figure 22B:
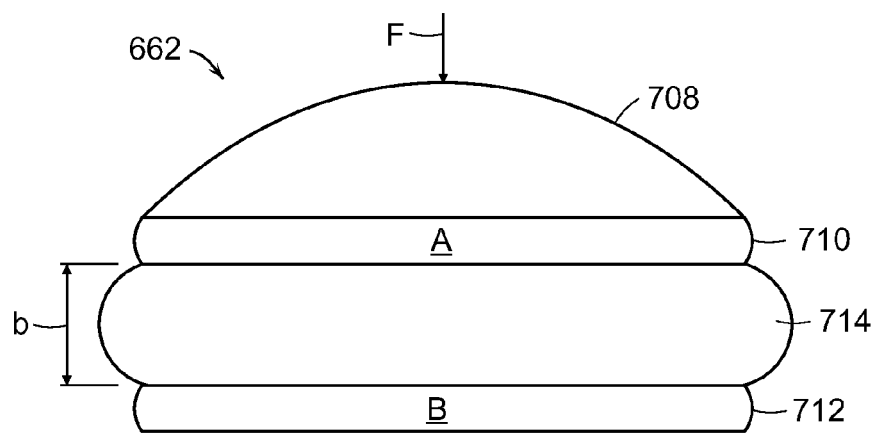

FIGS. 22A and 22B illustrate various embodiments of a proportional sensor. In the illustrated embodiment, FIGS. 22A and 22B illustrate two states of a proportional sensor that may be used as the value actuation sensor 662 according to various embodiments of the instrument. The valve actuation sensor 662 may include a face portion 708, a first electrode (A) 710, a second electrode (B) 712, and a compressible dielectric material 714 between the electrodes 710, 712, such as, for example, an electroactive polymer (EAP). The valve actuation sensor 662 may be positioned such that the face portion 708 contacts the actuation trigger 670 when retracted. Accordingly, when the actuation trigger 670 is retracted, the dielectric material 714 is compressed, as shown in FIG. 22B, such that the electrodes 710, 712 are closer together. Since the distance "b" between the electrodes 710, 712 is directly related to the impedance between the electrodes 710, 712, the greater the distance the more impedance, and the close the distance the less impedance. In that way, the amount that the dielectric 714 is compressed due to retraction of the actuation trigger 670 (denoted as force "F" in FIG. 22B) is proportional to the impedance between the electrodes 710, 712, which can be used to proportionally control the variable flow rate pneumatic valve 660.

Figure 23:
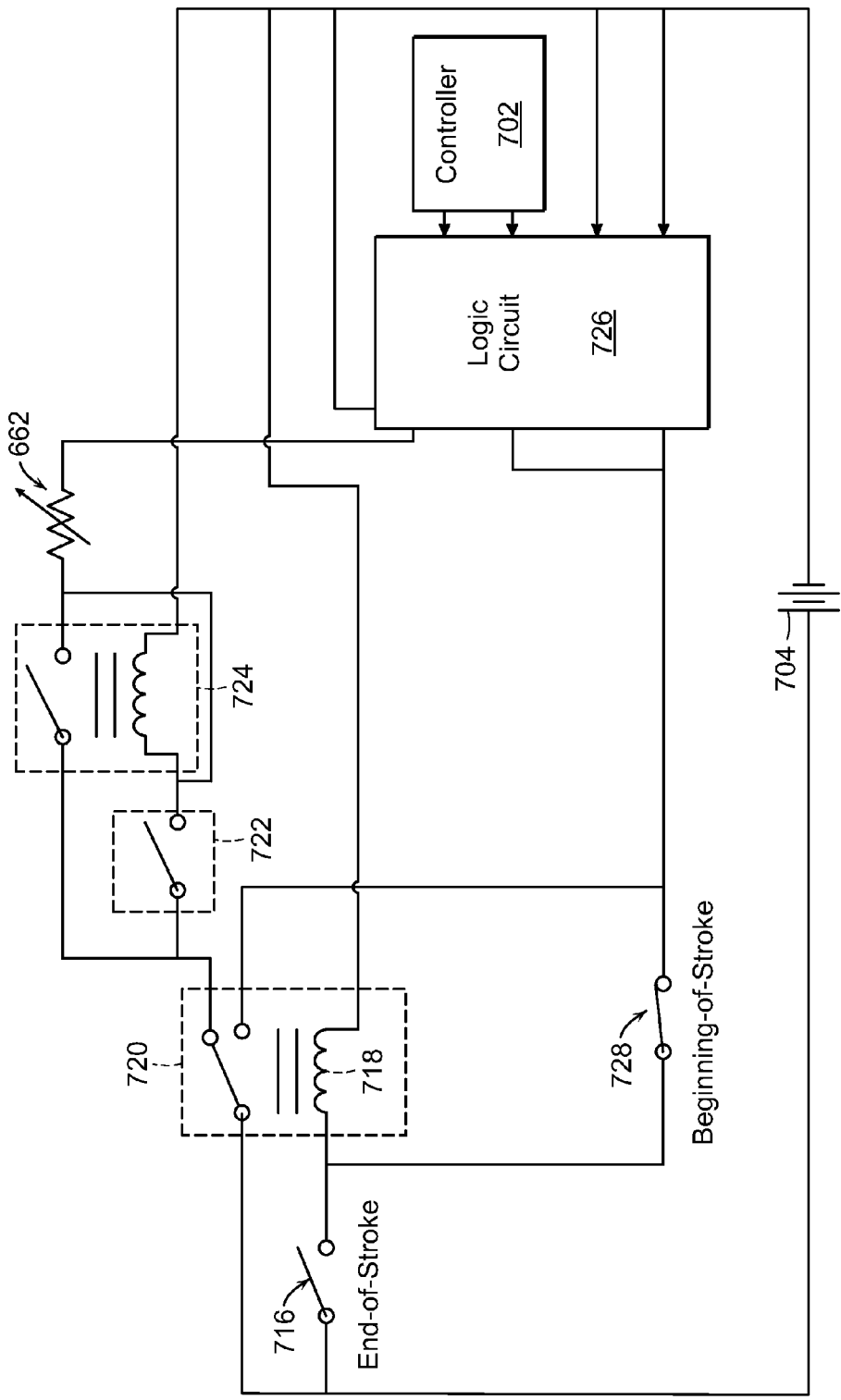
FIG. 23 is a schematic diagram of one embodiment of an electrical circuit of the instrument according to various embodiments thereof.

FIG. 23 is a schematic diagram of one embodiment of an electrical circuit of the instrument 10 according to various embodiments thereof. When an operator initially pulls in the firing trigger 310 after locking the closure trigger 302, the activation sensor 662 is activated by squeezing the activation trigger 670. This allows pressurized gas to flow through the variable flow rate pneumatic valve 660 under control of the actuator 706 and the controller 702. If the normally-open end-of-stroke sensor 716 is open (meaning the end of the end effector stroke has not been reached), pressurized gas will flow through the variable flow rate pneumatic valve 660 through the first supply conduit 540. Since the sensor switch 716 is normally open and it is not closed, the inductor 718 of the relay 720 will not be energized, so the relay 720 will be in its non-energized state. The circuit also includes a cartridge lockout sensor 722. If the end effector 12 includes a staple cartridge 50, the sensor 722 will be in the closed state, allowing current to flow. Otherwise, if the end effector 12 does not include a staple cartridge 50, the sensor 722 will be open, thereby preventing the battery 704 from supplying power to the actuator 706.

When the staple cartridge 50 is present, the sensor 722 is closed and energizes a single pole, single throw relay 724. When the relay 724 is energized current flows through the relay 724 and through the valve actuation sensor 662 (illustrated as a variable resistor). A logic circuit 726 receives the inputs from the sensor switch 716, the relay 720, the sensor 722, the single-throw relay 724, and the valve actuation sensor 662 and provides the information to the controller 702 in digital form. The controller 702 employs the information to generate a control signal 746 (FIG. 24) to maintain activation to the directional control valve 610 to allow pressurized gas to flow in the first supply line 540, causing the end effector to maintain its forward direction from the proximal end to the distal end.

When the end effector 12 reaches the end of its stroke, the sensor switch 716 will be activated, thereby energizing the relay 720. This causes the relay 720 to assume its energized state (not shown in FIG. 23), which causes current to bypass the cartridge lockout sensor 722 and the valve actuation sensor 662. The controller 702 now activates the directional control valve 610 with the control signal 796 (FIG. 24) to allow pressurized gas to flow in the second supply line 542, causing the end effector to reverse its direction from the distal end to the proximal end.

Because the beginning-of-stroke sensor 728 is normally-closed, current will flow back to the inductor 718 to keep it closed until the beginning-of-stroke 728 opens. When the knife assembly 30 is fully retracted, the beginning-of-stroke sensor 728 is activated, causing the sensor 728 to open. The controller 702 then provides a signal causing the actuator 706 to shut-off the variable flow rate pneumatic valve 660.

In other embodiments, rather than an analog proportional-type valve actuation sensor 662, a digital on-off type sensor may be employed instead. In such embodiments, the closure mechanism 730 would be either open to its full flow rate capacity or shut-off to zero flow rate substantially independent of the force applied by the operator. When fully open, the variable flow rate pneumatic valve 660 would generally provide a constant flow rate. The operator would still experience force feedback because the firing trigger 670 is geared into a gear drive train.

With reference now back to FIGS. 8-11, in various embodiments, the activation trigger 670 is supported adjacent the firing trigger 310 that is pivotally coupled to the handle assembly 300 by a pivot pin 370 that extends between the right hand case member 320 and left hand case member 330. Squeezing the activation trigger 670 inward towards the firing trigger 310 activates the valve activation sensor 662, which provides a proportional signal to the controller 702 to adjust the actuator 706 and thereby the variable flow rate pneumatic valve 660 to increase the flow rate of the pressurized gas flowing from the cylinder 622 into a supply line 680 coupled to the directional valve 610. Depending upon the position of the directional valve 610, the pressurized gas will either flow into supply line 540 or 542. For example, when the directional valve 610 is actuated by the clinician to fire the knife assembly 30, pressurized gas at the rate controlled by the controller 702 is permitted to flow through the variable flow rate pneumatic valve 660 to the supply line 540 into the first cylinder area 515 through the first opening 527 in the first piston head 528 and into the third cylinder area 532 upon actuation of activation trigger 670. In one embodiment, a pressure sensor may be fluidically coupled to the first piston head 528 to sense and measure the pressure at the first piston head 528. As the pressurized gas enters the third cylinder area 532, the second piston head 530 forces the piston bar 35 distally. In one embodiment, a pressure sensor also may be fluidically coupled to the second piston head 530 to sense and measure the pressure at the second piston head 530. Gas located in the fourth cylinder area vents therefrom through exhaust opening 523 in the second cylinder housing 520. Similarly, the gas contained in the second cylinder area 518 is permitted to vent therefrom through second opening 529 into the second supply line 542. The second supply line 542 carries the vented gas to the directional valve 610 wherein it is ultimately vented therefrom. Continued application of pressurized gas to the first cylinder area 515 and the third cylinder area 532 causes the knife assembly 30 to be fully extended through the end effector 12. As the knife assembly 30 passes through the end effector 12, it severs the tissue clamped therein and fires the staples 70 in the staple cartridge 50 (drives the staples into forming contact with the lower surface of the anvil 40). Once the knife assembly 30 has been advanced to its distal-most position in the end effector 12, the clinician discontinues the application of pressurized gas by releasing the activation trigger 670.

To retract the firing mechanism or knife assembly 30, the clinician manually moves the selector switch 612 or appropriate button for adjusting the directional valve 610 to the retract position and begins to squeeze the activation trigger 670 which causes the pressurized gas to flow into the second supply line 542. Gas flowing through the second supply line 542 enters the second cylinder area 518 which causes the second cylinder housing 520 to retract proximally into the first cylinder housing 510. Gas in the first cylinder area 515 is permitted to vent through the first supply opening 513 into the first supply line 540. Gas passing through the first supply line 540 enters the directional valve 610 wherein it is vented therefrom. Once the pressurized gas entering the second cylinder area 518 has caused the second cylinder housing 520 to retract into the first cylinder housing 510 as shown in FIG. 10, gas passing through the second opening 529 is now able to pass through the exhaust opening 523 in the first cylinder housing 510 and into the fourth cylinder area 534. As pressurized gas enters the fourth cylinder area 534, the second piston head 530 draws the piston bar 35 proximally into the second cylinder housing 520. Gas in the third cylinder area 532 passes through the first opening 527 into the first cylinder area 515 from which it is vented in the manner described above.

The variable flow rate value in the form of the variable flow rate pneumatic valve 660 of various embodiments of the instrument may employ various electrically controlled elements or components (not shown) to bias the variable flow rate pneumatic valve 660 to an unactuated position. When in the unactuated position, the variable flow rate pneumatic valve 660 may be configured to prevent any flow of gas from the sources of gas 620 or 618 through an orifice (not shown) within the variable flow rate pneumatic valve 660. Thus, when the actuator trigger 670 is in the unactuated position, the device is essentially off.

FIG. 24 illustrates one embodiment of an electrically controlled pneumatic system 700. The pneumatic system 700 comprises an internal or external source of pressurized gas. In the illustrated embodiment, the pneumatic system 700 comprises a cylinder 622 as a source of pressurized gas that may be rechargeable with a preferred pressurized gas. The nonreplaceable/rechargeable sources (cylinders) of pressurized gas could also be effectively employed. Still in other embodiments, the handle assembly 300 may be provided with a port 616 for supplying pressurized gas from tan external source 618 of pressurized gas. The electronic control module 603 is in electrical communication with sensors and flow control elements to control the flow rate through the variable flow rate pneumatic valve 660 (and the directional control valve 610). For example, the electronic control module 603 provides flow control signal based on feedback signals $S_1$ to $S_n$ received from a plurality of sensors and a plurality of pressure measurement signals $P_1$ to $P_m$ received from a plurality of pressure sensors, where n and m are any positive integers. In one embodiment, the pneumatic system is in fluid communication with the first and second supply lines 540, 542 and the measurement circuit 732. The measurement circuit 732 receives pressure signals $P_1$ to $P_m$ from the variable flow rate pneumatic valve 660 and the first and second supply lines 540, 542 and provides a feedback signal 736 to the controller 702 that is proportional to the flow rate in the pneumatic system. The measurement circuit 732 provides the feedback signal 736 in digital or any suitable form.

In one embodiment, the measurement circuit 732 receives pressure inputs $P_1, P_2, P_4, P_5 \ldots P_m$ from the various pressure sensors fluidically coupled throughout the pneumatic system. For example, a pressure sensor $541_1$ may be fluidically coupled to the input supply line 650 at the inlet portion of the valve 660 upstream of the closure mechanism 730 to measure the inlet pressure $P_1$, which in one embodiment is the same as the supply 622 pressure. Pressure sensor $541_2$ may be fluidically coupled to the outlet of the valve 660 to measure the pressure $P_2$ downstream of the closure mechanism 730 in the supply line 680. The electrical output signals from these pressure sensors $54_1$, and $541_2$ also may be employed to determine the differential pressure across the closure mechanism 730, which is $\Delta P=(P_2-P_1)$. In other embodiments, the pressure sensors $541_1$ and $541_2$ may be configured as a single differential pressure sensor. It is well known to calculate flow rate through an orifice based on the differential pressure $\Delta P$ across the orifice. Pressure sensor $541_3$ may be fluidically coupled to the first outlet of the directional control valve 610 to measure the pressure $P_3$ in the first supply line 540. Pressure sensor $541_4$ may be fluidically coupled to the second outlet of the directional control valve 610 to measure the pressure $P_4$ in the second supply line 542. Other pressure sensors $541_m$ may be fluidically coupled throughout the pneumatic system to measure the corresponding pressure $P_m$ in the pneumatic system. In one embodiment, the controller 702 and/or the measurement circuit 732 also receive feedback signals $S_1$ to $S_n$ from a plurality of sensors disposed throughout the instrument 10. The sensors may comprise limit switches, solid state switches, relays, and/or flow sensors.

In various embodiments, the controller 702 receives a feedback signal 736 from the measurement circuit 732. The feedback signal 736 is proportional to the flow rate through the variable flow rate pneumatic valve 660 and may be based on the measured pressures $P_1$ to $P_m$ from the respective pressure sensors $541_1$ to $541_m$. The controller 702 generates a control signal 738 that is provided to the actuator 706 to control the closure mechanism 730, which sets the flow rate through the variable flow rate pneumatic valve 660. The controller 702 may comprise a microprocessor to execute a suitable control algorithm to relate the actual flow rate feedback signal 736 provided by the measurement circuit 732 to the energizing control signal 738 provided to the actuator 706 to control the closure mechanism 730 to achieve the desired flow rate through the flow-through portion of the variable flow rate pneumatic valve 660. The control algorithm may be any suitable proportional, derivative, integral control algorithm, or any combination thereof.

The actuator 706 sends a control signal 740 to actuate a closure mechanism 730 located in the flow path 742 of the flow-through portion 734 of the variable flow rate pneumatic valve 660. The variable flow rate pneumatic valve 660 may comprise various types of electrically actuated closure mechanisms 730 located in the flow path 742 of the flow-through portion 734 to control the gas discharge rate therethrough. The closure mechanism 730, pressure sensors $P_1$-$P_m$ and the measurement circuit 732, the controller 702, and the actuator 706 form a closed loop control system to control the gas discharge rate through the pneumatic system. The closure mechanism 730 includes electrically controlled elements or components such as one or more solenoids, piezo-actuators, or electric motors, or any combination thereof. These electrically controlled elements or components are operably controlled by the controller 702 and the actuator 706 to selectively control the closure mechanism 730. The flow rate or discharge of the gas through the variable flow rate pneumatic valve 660 into the pneumatic drive member 500 comprising the actuation cylinder assembly 501 may be determined by the state of the closure mechanism 730 and the pressure throughout the pneumatic system. The controller 702 also generates a control signal 746 to the direction control valve 610 to select either the first supply conduit 540 or the second supply conduit 542 as the gas discharge path. This may be done to control the direction of the actuation cylinder assembly 501 at the beginning-of-stroke or at the end-of-stroke. In one embodiment, the controller 702 may control the actuation of a solenoid or piezo-actuator to control the gas discharge rate of the pressurized gas through the variable flow rate gas discharge valve 660.

In various embodiments, the closure mechanism 730 may comprise a solenoid or a piezo-actuator. Accordingly, the controller 702 may be configured to provide a control signal 738 in the form of a series of electrical pulses to the actuator 706 that is suitable to actuate the solenoid or piezo-actuator in a pulsed manner. The actuator 706 may comprise a pulse drive circuit to suitably drive the solenoid or piezo-actuator with a series of electrical pulses. To increase or decrease the flow rate, the controller 702 respectively increases or decreases the frequency of the pulses. The actuator 740 applies the pulses to the solenoid or piezo-actuator.

In other embodiments, the closure mechanism 730 may comprise an element with a controlled variable internal orifice located in the flow-through portion 734 of the variable pneumatic valve 660. One such closure mechanism may be an iris-type diaphragm control valve actuated by a motor. An iris-type diaphragm flow valve includes a number of fingers or blades that extend into the flow-through portion 734 and form a circular shutter having a variable orifice that is controlled by the rotation of a motor coupled to the iris-type diaphragm flow valve. The degree to which the fingers extend into the flow path 742 controls the radius of the orifice hence the amount of fluid that may flow therethrough and hence the flow rate through the variable flow rate pneumatic valve 660. The actuator 706 for the iris-type valve may be a motor adapted and configured to drive the iris-type valve. Thus, the motor controls the diameter of the variable opening or orifice to control the discharge rate of the pressurized gas in the flow-through portion 734 of the variable flow rate pneumatic valve 660. The diameter of the orifice of the valve may be set by the controller 702 for a desired flow rate. The actual flow rate may be determined by the measurement circuit 732 based on the measured pressures $P_1$ to $P_m$ from the respective pressure sensors $541_1$ to $541_4$ and/or signals $S_1$ to $S_n$ from other sensors (such as for example, various flow sensors disposed throughout the pneumatic system). In one embodiment, the flow rate through the flow-through portion 734 may be determined based on the diameter of the orifice of the valve and the differential pressure $\Delta P$ ($P_2$ to $P_1$) cross the orifice. Based on the feedback signal 736, the controller 702 provides a control signal 738 to the actuator 730 that is suitable to control the valve motor. The actuator 730 sets the desired gas discharge flow rate by providing a suitable control signal to the iris-type valve mechanism to set the internal orifice diameter to produce the desired flow rate.

It will be appreciated by those skilled in the art that information may be transferred throughout the electrically controlled pneumatic system in accordance with a suitable communication protocol. Examples of such protocols include the HART® and the all-digital FOUNDATION® Fieldbus protocol. Any suitable protocols may be employed. In addition, any suitable electronic circuitry may be employed to couple and to communicate over the communication loop.

In the embodiments described above, the variable flow rate pneumatic valve 660 may be electrically coupled to the activation trigger 670 and the valve activation sensor 662. The activation trigger 670 and activation sensor 662 are coupled to the controller 702. The valve activation sensor 662 is coupled to the activation trigger 670 to detect when the activation trigger 670 has been drawn in (or "closed") toward the pistol grip portion 342 of the handle assembly 300 by the operator to thereby actuate the cutting/stapling operation by the end effector 12. The valve activation sensor 662 may be a proportional sensor such as, for example, a rheostat or variable resistor. When the activation trigger 670 is drawn in, the valve activation sensor 662 detects the movement, and sends an electrical signal indicative of the desired discharge rate of the pressurized gas to be supplied by the variable rate pneumatic valve 600 to the pneumatic actuation cylinder assembly 501. When the valve actuation sensor 662 is a variable resistor or the like, the output of the actuator 706 generally may be proportional to the amount of movement of the actuation trigger 670. That is, if the operator only draws or closes the actuation trigger 670 in a little bit, the output of the actuator 706 is relatively low (e.g., low flow rate). When the actuation trigger 670 is fully drawn in (or in the fully closed position), the output of the actuator 706 is at its maximum (e.g., highest flow rate). In other words, the harder the user pulls on the actuation trigger 670, the more output signal is applied to the actuator 706, causing greater gas discharge flow rates through the flow-through portion 734 of the variable flow rate pneumatic valve 660. Thus, as the clinician squeezes the activation trigger 670 inward toward the firing trigger 310, the valve activation sensor 662 provides a proportional signal to the controller 702, which sends a control signal 738 to the actuator 706 to actuate the closure mechanism 730. In response, the closure mechanism 730 of the variable flow rate pneumatic valve 660 increases to permit the flow rate of the gas to increase therethrough. Thus, quickly squeezing the activation trigger 670 may cause the firing rate of the device to increase and slowing the rate that the activation trigger 670 is squeezed slows the firing rate. Thus, the amount of gas flow permitted through the variable flow rate pneumatic valve 660 can be substantially proportionate to the amount of manual force applied to the activation trigger 670.

In other embodiments, the variable flow rate pneumatic valve 660 may be electronically controlled such that upon actuation of the activation trigger, the variable flow rate pneumatic valve 660 digitally spurts gas therefrom. The variable flow rate pneumatic valve 660 discharges a small amount of gas in a pulse manner and the harder that the activation trigger 670 is squeezed, the closer the pulses will be. Such arrangement serves to selectively regulate the volume of gas employed to actuate the device.

Also, in still other embodiments, the actuation mechanism may comprises a different type of mechanism that is not pivotally supported relative to the handle assembly as is the activation trigger 670. For example, the activation trigger may comprise a spring actuated slide switch, etc. Accordingly, the protection afforded to those embodiments of the present invention should not be solely limited to embodiments employing a pivoting actuated trigger.

Figure 26:
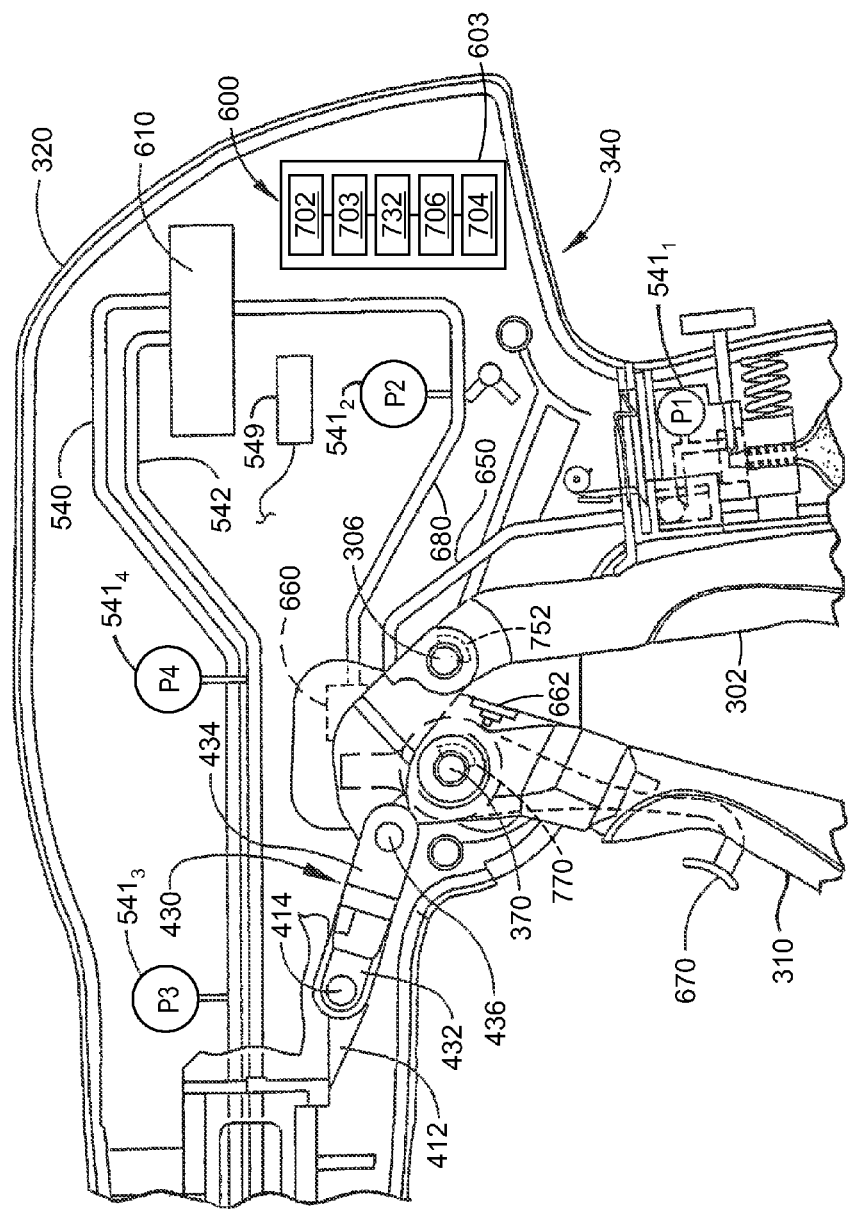
FIG. 26 illustrates one embodiment of a closure trigger sensor.

Also in various embodiments, each of the pressure sensors $541_1$ to $541_m$ may be coupled to a visual display to display the respective measured pressures $P_1$ to $P_m$ in any of the supply lines 650, 680, 540, 542 in the pneumatic system as shown in FIGS. 8 and 26. The display provides a visual indication of the pressure readings $P_1$ to $P_m$ by each of the respective pressure sensors $541_1$ to $541_m$ to a clinician. One or more windows may be provided through a corresponding portion of the handle assembly 300 to enable the clinician to view the pressure displayed by the pressure sensor $541_1$ or other arrangements may be employed to enable the clinician to view the pressure displayed by the pressure sensor $541_1$ during use. In various embodiments, the pressure display may be coupled to additional circuits to provide an electronic signal indication of the pressure readings $P_1$ to $P_m$ by any of the supply lines 650, 680, 540, 542 to the controller 702. In these non-limiting embodiments, the pressure sensors $541_1$-$541_m$ provide feedback signals $P_1$-$P_m$ to the controller 702 and the pressure display provides feedback to the clinician of the forces encountered during the firing stroke. Those of ordinary skill in the art will understand that, in certain non-limiting embodiments, the force necessary to actuate the firing mechanism is directly proportionate to the pressure in the cylinder assembly 501. If those forces are small, then the cylinder assembly 501 does not require large pressures to be actuated. On the other hand, if the forces needed to actuate the cylinder assembly 501 are high, more gas will have to be released into the cylinder assembly 501 increasing the pressure therein to fully actuate the firing mechanism. The pressure display serves to provide the clinician with a proportionate reading to the forces being experienced by the end effector.

Figure 8C:
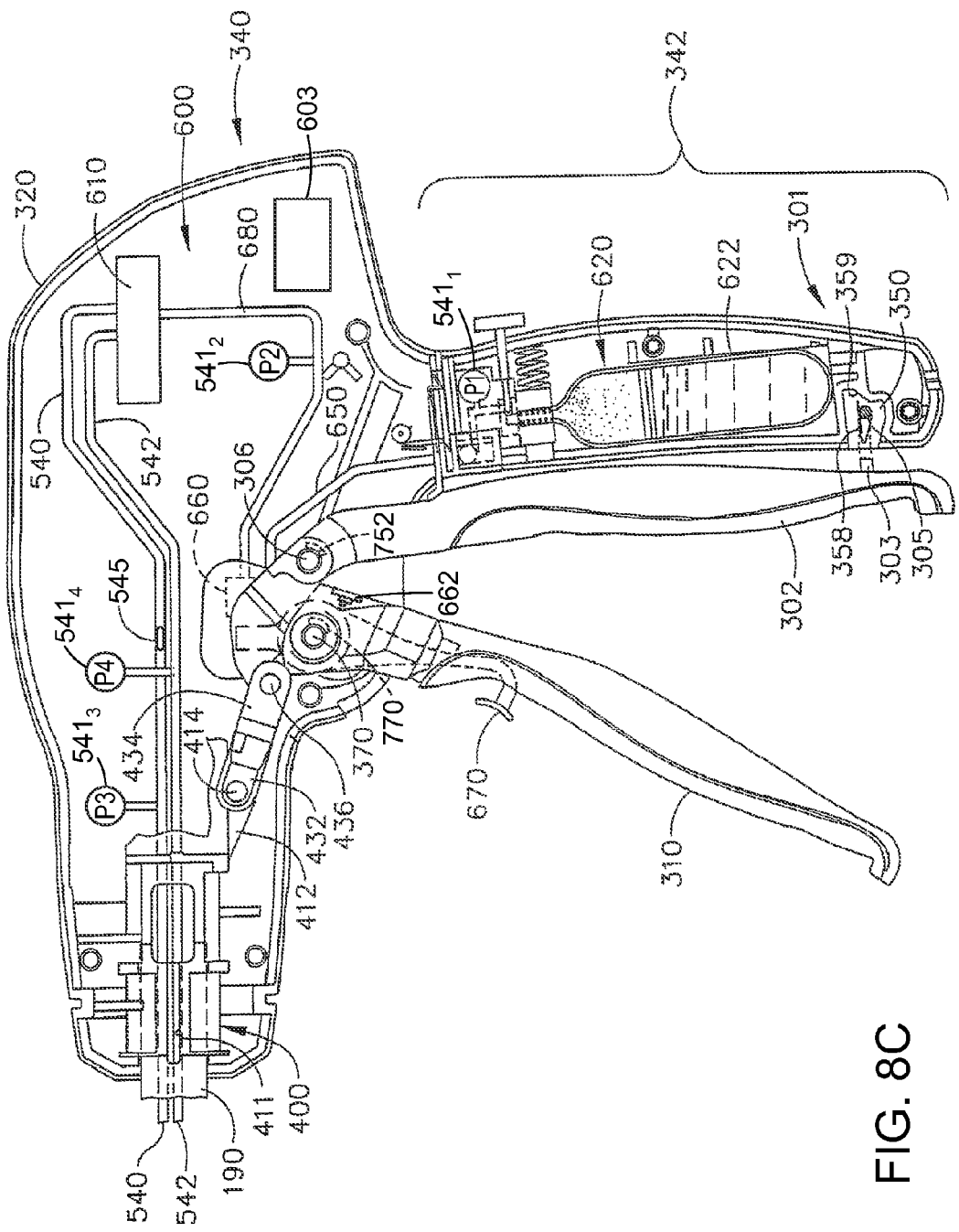
FIG. 8C is a cross-sectional view of another handle assembly embodiment of the surgical cutting and fastening instrument.

In other various embodiments, an audible outlet 545 may be provided in the supply line 540 as shown in FIG. 8C. Such audible outlet permits a small amount of gas to be released from the supply line 540. The ensuing whistle pitch caused from the discharge of that gas would increase as the pressure forces increased. The clinician can then relate the pitch of the whistle to the forces experienced by the firing mechanism. Thus, such arrangement provides the clinician with an audible feedback mechanism for monitoring the firing forces being experienced by the drive system 500 and ultimately the firing mechanism.

Various non-limiting embodiments also may be provided with means for automatically notifying the clinician when the firing mechanism has reached the end of the firing stroke. For example, as shown in FIG. 4, a limit switch 546 may be provided within the distal spine segment 110 for detecting an activation member 547 embedded into or otherwise attached to the firing rod 35 as shown in FIG. 11. The activation member 547 is so located such that when the firing bar 35 and firing mechanism reaches the end of the firing stroke, the activation member 547 is detected by the limit switch 546 which may be electrically coupled to the controller 702 and the directional control valve 610 for transmitting an appropriate signal $S_n$ thereto. Upon receipt of such signal $S_n$, the directional control valve 610 may be configured to automatically shift to the retract position and to permit the firing mechanism to be retracted. In addition, the limit switch 546 may be coupled to an indication member generally designated as 549 in FIG. 8. In various embodiments, the indication member may provide the clinician with an audible signal, a visual signal or a combination of audible and visual signals indicating that the firing mechanism has reached the end of the firing stroke. For example, the indication member may comprise a sound generating device, an LED, a vibration generating device, and/or a combination of such devices. The limit switch 546 and related control components may be powered by the battery 704 supported in the housing assembly 300 or it may be provided with electrical power from an external source of electrical power. Thus, various non-limiting embodiments of the present invention may be provided with a means for providing the clinician with a visual and/or audible signal indicating that the firing mechanism has reached the end of the firing stroke and/or a means for automatically pneumatically retracting the firing mechanism to the unactuated position.

As shown in FIGS. 4, 10, and 11, a locking protrusion 39 may be formed on the bottom of the piston bar 35. When the knife assembly 30 is in the fully retracted position as shown in FIG. 4, the arm 118 of the locking spring 112 applies a biasing force to the distal end of the cylinder assembly 501. Because the cylinder assembly 501 is pivotally mounted within the distal spine segment 110 by trunions 519, the distal end of the cylinder assembly 501 pivots downwardly within the distal spine segment 110 and further causes the locking protrusion 39 on the piston bar 35 to drop into a locking opening 21 in the elongate channel 20. Such arrangement serves to lock the knife assembly 30 in the retracted position by virtue of the frictional engagement of the locking protrusion 39 with the portions of the elongate channel 20 defining the locking opening therein. As can be seen in FIGS. 10 and 11, the locking protrusion 39 has a proximal ramp surface 39' and a distal ramp surface 39" to enable the locking protrusion to easily enter and exit the locking opening in the elongate channel 20. Those of ordinary skill in the art will readily appreciate that other knife bar locking arrangements may be successfully employed without departing from the spirit and scope of the present invention.

FIGS. 12-16A illustrate another embodiment of the instrument wherein the drive member 500 comprises a cylinder assembly 800 that is similar in construction as cylinder assembly 501 described above, except for the differences noted below. For example, in this embodiment, springs 850, 852 are employed to retract the piston bar 35. As can be seen in FIGS. 12 and 13, the cylinder assembly 800 includes a first housing 810 that has a first closed end 812 and a first supply port 813 therethrough. A first supply line 840 is attached to the first closed end 812 to supply pressurized gas through the first supply port 813. In this embodiment, the first cylinder housing 810 lacks the second opening 529 that was described in connection with various embodiments described above. A second cylinder housing 820 is slidably received in the first cylinder housing 810 and has a second closed proximal end 822 that has a first piston head 828 formed thereon. A first cylinder area 815 is defined between the first closed end 812 and the first piston head 828. A first retraction spring 850 is provided between the first piston head 828 and a first flange 817 formed on the distal end of the first cylinder housing 810. The first retraction spring 850 serves to bias the second cylinder housing 820 into the retracted position in the first cylinder 810 as shown in FIG. 12. The piston bar 35 has a stepped end 35' that is sized to enter the second distal end 824 of the second cylinder housing 820. A second flange 825 is formed on the second distal end 824 to achieve a substantially siding seal with the stepped portion 35' of the piston bar 35. A second piston head 830 is provided on the proximal end of the stepped piston bar section 35' to define a third cylinder area 832 between the second piston head 830 and the first piston head 828. A first opening 827 is provide through the first piston head 828 to enable air to pass between the first cylinder area 815 and the third cylinder area 832. A second retraction spring 852 is provided between the second flange 825 and the second piston head 830 as shown in FIG. 12 to bias the second piston head 830 and stepped piston bar 35' to the fully retracted position within the second cylinder housing 820 as shown in FIG. 12.

Figure 16:
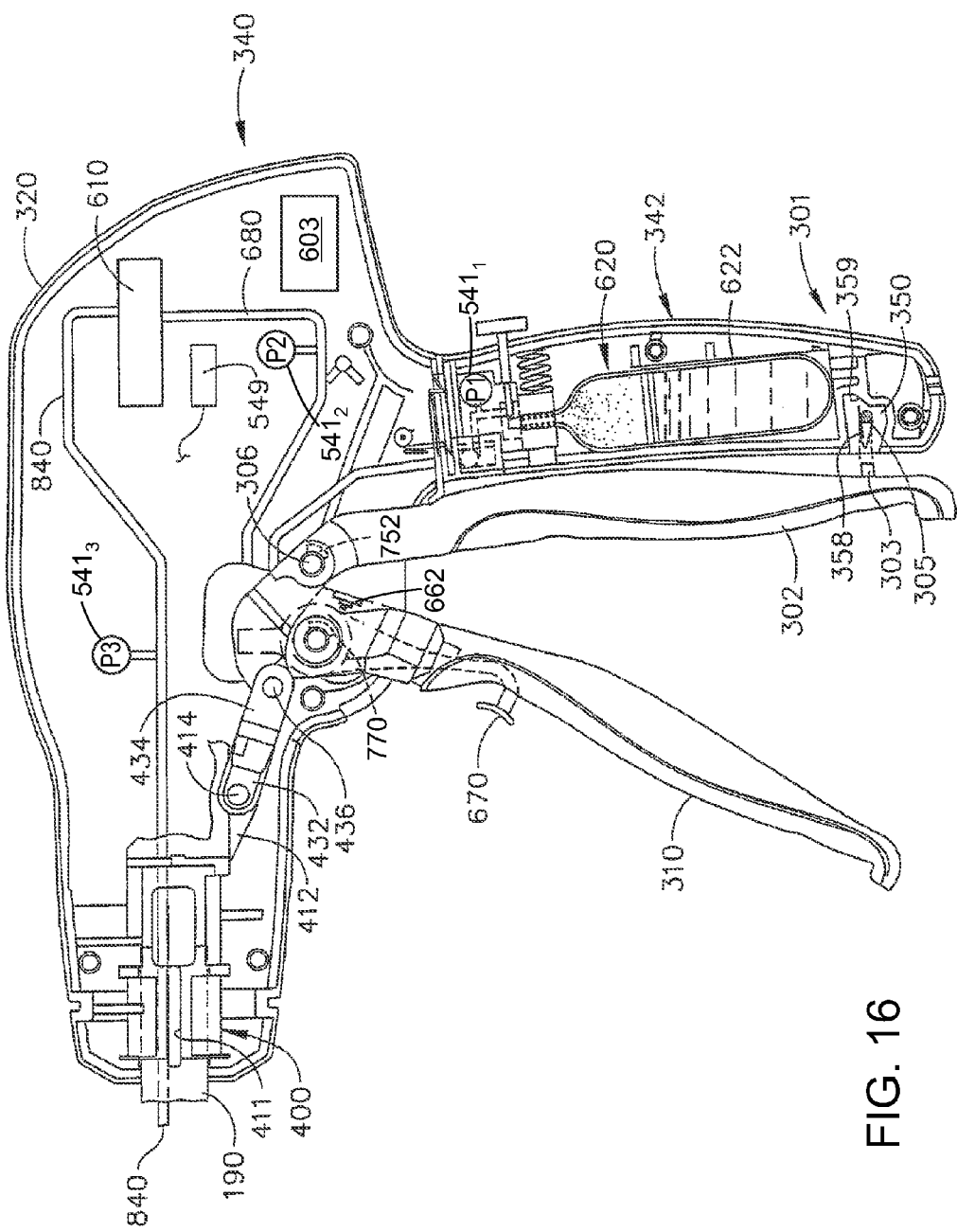
FIG. 16 is a cross-sectional view of a handle assembly that may be used in connection with the embodiment depicted in FIGS. 12-15.

This embodiment of the present invention may be operated as follows. As can be seen in FIG. 16, the handle assembly 300 is provided with a replaceable source 620 of pressurized gas as was discussed above. However, those of ordinary skill in the art will appreciate that nonreplaceable sources (cylinders) of pressurized gas could also be effectively employed. Still in other embodiments, the handle assembly 300 may be provided with a port 616 for facilitating attachment of the directional control valve 610 and related components to an external source of pressurized gas 618. See FIG. 16A. For example, the instrument 10 could be coupled to the facility's compressed air line through a flexible supply line 617.

To operate the instrument, the clinician moves the direction control valve selector switch 612 (FIG. 1) or push buttons to the forward (extend) position and begins to squeeze the activation trigger 670 which permits the pressurized gas to flow from the cylinder 622 (or external source 618) through the supply line 680 through the directional control valve 610 and into the supply line 840. The pressurized gas flows from the first supply line 840 through the first supply port 813 into the first cylinder area 815, through the first opening 827 and into the third cylinder area 832. Gas entering the third cylinder area 832 causes the second piston head 830 and the stepped portion 35' of the piston bar 35 to move distally. After the second piston head 830 has moved to a fully extended position (FIG. 13), gas continuing to enter the first cylinder area 815 biases the second housing 820 to its fully extended position. Once the knife assembly 30 has been advanced to its distal-most position in the end effector 12, the clinician discontinues the application of pressurized gas by releasing the activation trigger 670.

To retract the firing mechanism or knife assembly 30, the clinician 30 moves the directional valve selector switch 612 to the reverse (retract) position wherein the first supply line 840 is connected to a vent in the directional valve 610. Gas in the third cylinder area 832 and the first cylinder area 815 is permitted to exit through the first supply port 813 into the supply line 840 and is ultimately vented through the directional valve 610. As the gas exits the third cylinder area 832, the second retract spring 852 retracts the stepped portion 35' of the piston bar 35 into the second cylinder housing 820. Likewise, as the gas exits the first cylinder area 815, the first retraction spring 850 biases the second cylinder housing 520 into the first cylinder housing 810.

Figure 16A:
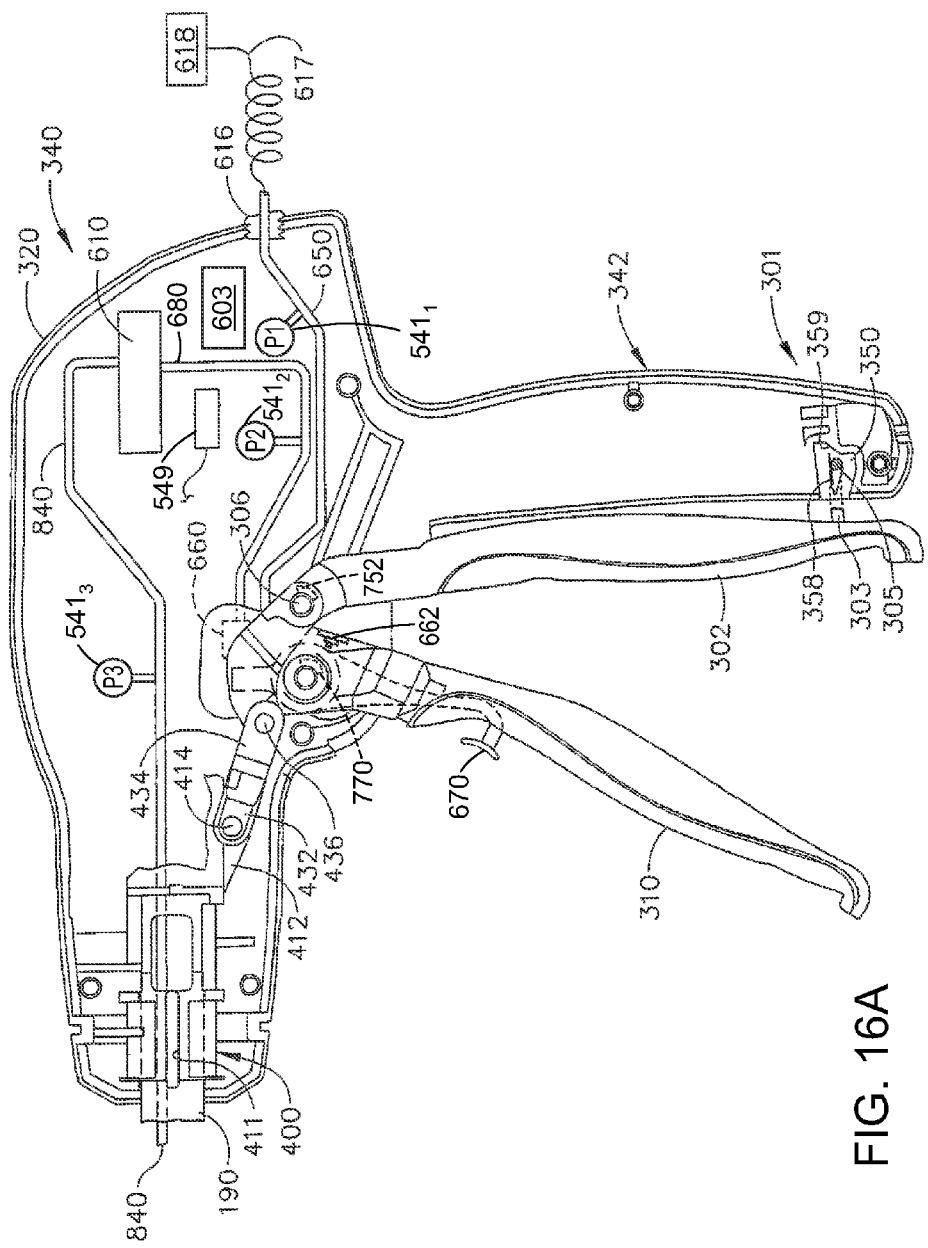
FIG. 16A is a cross-sectional view of another handle assembly that may be used in connection with the embodiment depicted in FIGS. 12-15 wherein the source of pressurized gas is external to the handle assembly.
Figure 16B:
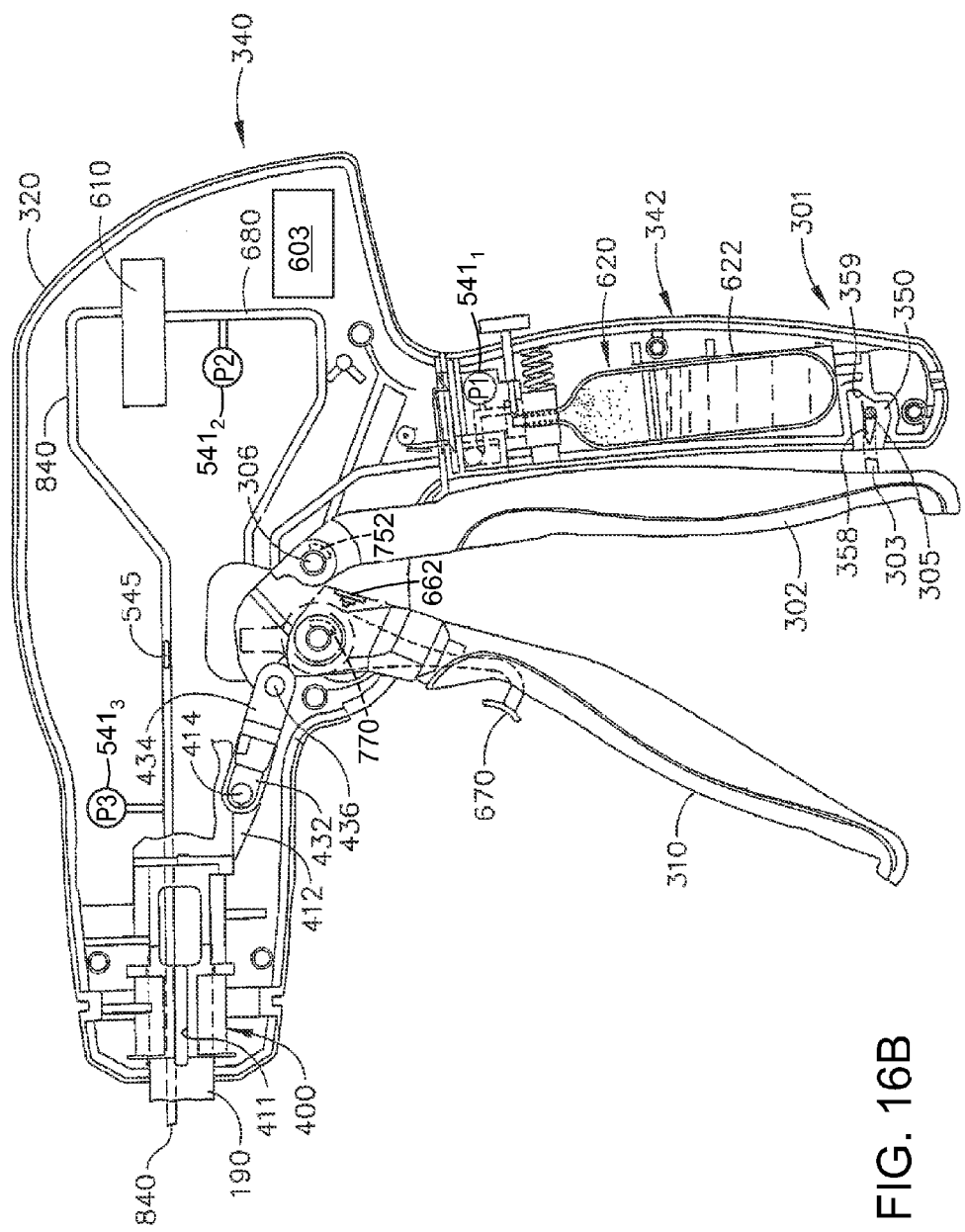
FIG. 16B is a cross-sectional view of another handle assembly embodiment of the surgical cutting and fastening instrument.

Also in this embodiment, the pressure sensor 5413 may be coupled to display electronically to the indication member 549. The pressure sensor 5413 is fluidically coupled to supply line 840 as shown in FIGS. 16 and 16A which can function in the manner described above and serves to provide the clinician with a proportionate reading to the forces being experienced by the end effector 12. In other various embodiments, an audible outlet 545 may be provided in the supply line 840 as shown in FIG. 16B which can function in the manner described above to provide the clinician with an audible feedback mechanism for monitoring the firing forces being experienced by the drive system 500 and ultimately the firing mechanism. In other alternative embodiments, a limit switch 546 (FIG. 15) may be provided within the distal spine segment 110 for detecting an activation member 547 (FIGS. 12 and 13) embedded into the firing rod 35 for automatically controlling the directional switch 610 and/or providing visual and or audible signals indicating that the firing mechanism has reached the end of the firing stroke.

FIGS. 17-21A illustrate yet another embodiment of the instrument wherein the drive member 500 comprises a bellows assembly 900. The bellows assembly 900 may have a distal end 902 that is attached to distal portion 31 of the knife bar assembly 30. The distal end 902 has a protrusion 904 formed thereon that sized to be received in an aperture 33 in portion 31. The protrusion 904 may be frictionally received within the aperture 33 and/or retained therein by adhesive and/or welding. The distal portion 31 may be constructed and configured as was described in detail above.

The bellows assembly 900 further includes an expandable/retractable bellows portion 910 that is sized to extend and retract within a bellows passage 117 in the distal spine segment as shown in FIG. 18. The bellows portion 910 may be formed with wire containment rings 912 as shown in FIG. 20 and may be attached to a base portion 914 that is non-movably attached to the distal spine segment 110 or comprises an integral portion of the distal spine segment 110. The base 914 may be attached to the distal spine segment 110 by adhesive and/or screws. A supply port 916 is provided through the bellows base 914 and a supply line 940 is attached to the supply port 916. The supply line 940 is also coupled to the directional control valve 610 in the handle assembly 300. See FIGS. 21, 21A. The directional control valve 610 also communicates with a vacuum port 620 mounted in the handle assembly 300 through a vacuum line 922. The vacuum port 620 is attachable to a source of vacuum 630 by, for example, a flexible line 632. The source of vacuum may be a permanent vacuum supply line in the facility. A flexible vacuum line 632 may be attached from the port 620 to the vacuum source 630 to enable the clinician to freely manipulate the instrument.

This instrument may be provided with the closure tube assembly 170 and closure trigger 302 arrangements described above. Thus, tissue may be clamped in the end effector 12 in the manner described above. After the tissue has been clamped in the end effector 12, the clinician may fire the instrument as follows. The clinician moves the selector switch 612 (FIG. 1) or buttons for the directional control valve 610 to the forward (extend) position and begins to squeeze the activation trigger 670. As the activation trigger 670 is squeezed, the rate valve 660 permits the pressurized gas to flow from the pressure source 620 (FIG. 21) or 618 (FIG. 21A) to the directional control valve 610. The directional control valve 610 permits the pressurized gas to flow through the supply line 940 into the bellows 910 causing it to extend distally. As the bellows 910 extends distally, it drives the knife assembly 30 through the end effector 12 severing the tissue clamped therein and driving the staples 70 in the staple cartridge 50 into forming contact with the bottom surface of the anvil 40. After the knife assembly 30 has been driven to its distal-most position in the end effector 12, the clinician releases the activation trigger 670. To retract the knife assembly 30, the clinician moves the selector switch 612 for the directional control valve 610 to the retract position to thereby permit the source of vacuum 630 to be coupled to the supply line 940. The application of the vacuum to the supply line 940 causes the bellows 910 to retract to its retracted position illustrated in FIG. 18. After the bellows 910 has been fully retracted, the clinician may move the selector switch 612 or buttons to a position wherein the directional control valve stops the application of vacuum to the supply line 940. However, the remaining vacuum within the supply line 940 may serve to retain the bellows 910 in the retracted position.

Figure 21:
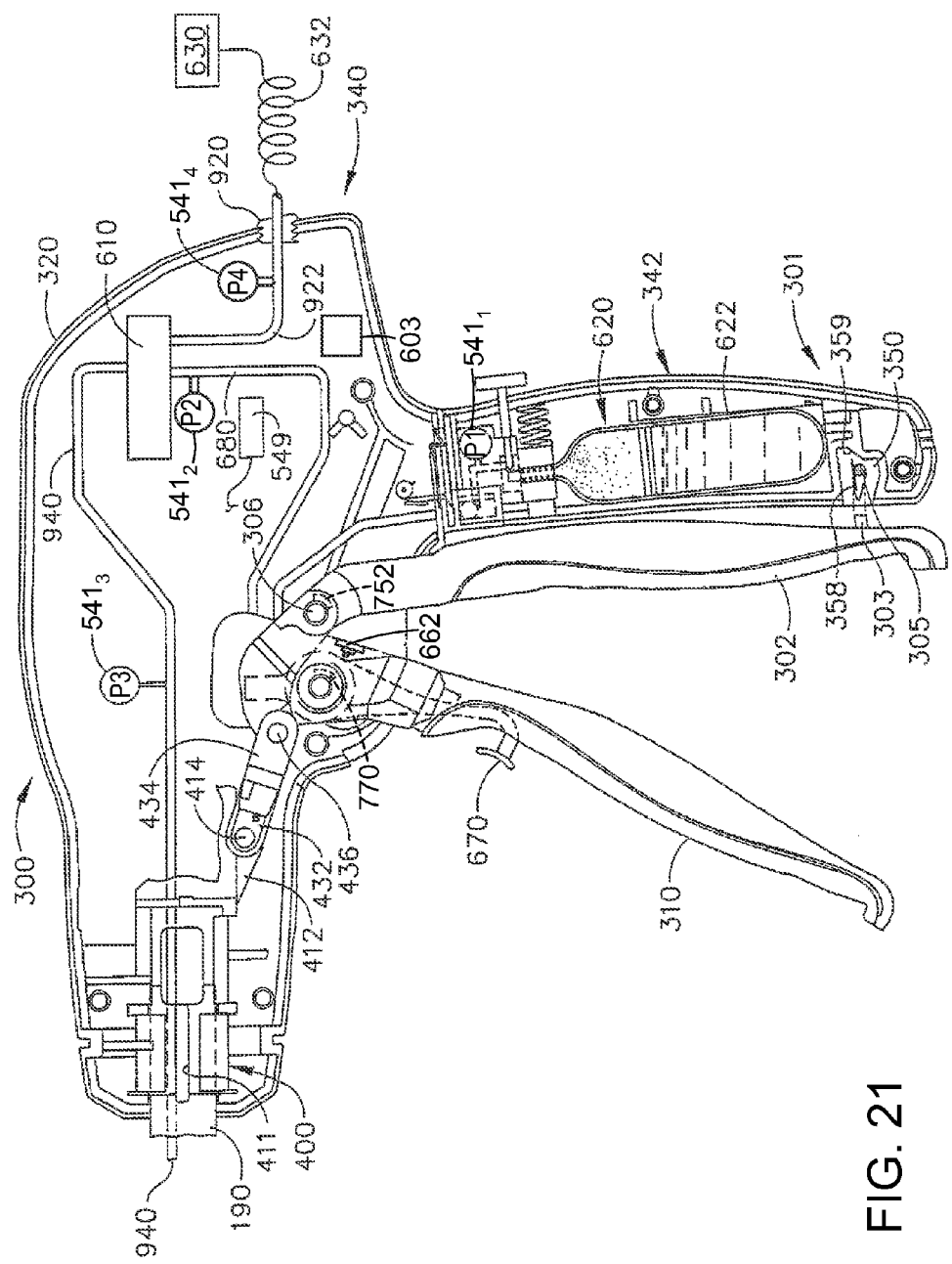
FIG. 21 is a cross-sectional view of a handle assembly embodiment that may be used in connection with the embodiments depicted in FIGS. 17-20.

In the embodiment depicted in FIG. 21, a removable source 620 of pressurized gas is employed. As will be further discussed in detail below, such source of pressurized gas comprises a cylinder 622 that may be rechargeable. Those of ordinary skill in the art will appreciate, however, that nonreplaceable/rechargeable sources (cylinders) of pressurized gas or pressurized fluid could also be effectively employed. Still in other embodiments, the handle assembly 300 may be provided with a port 616 for supplying pressurized gas to an external source of pressurized gas. For example, the instrument 10 could be coupled to the facility's compressed air line through a flexible supply line 617. See FIG. 21A.

Figure 21A:
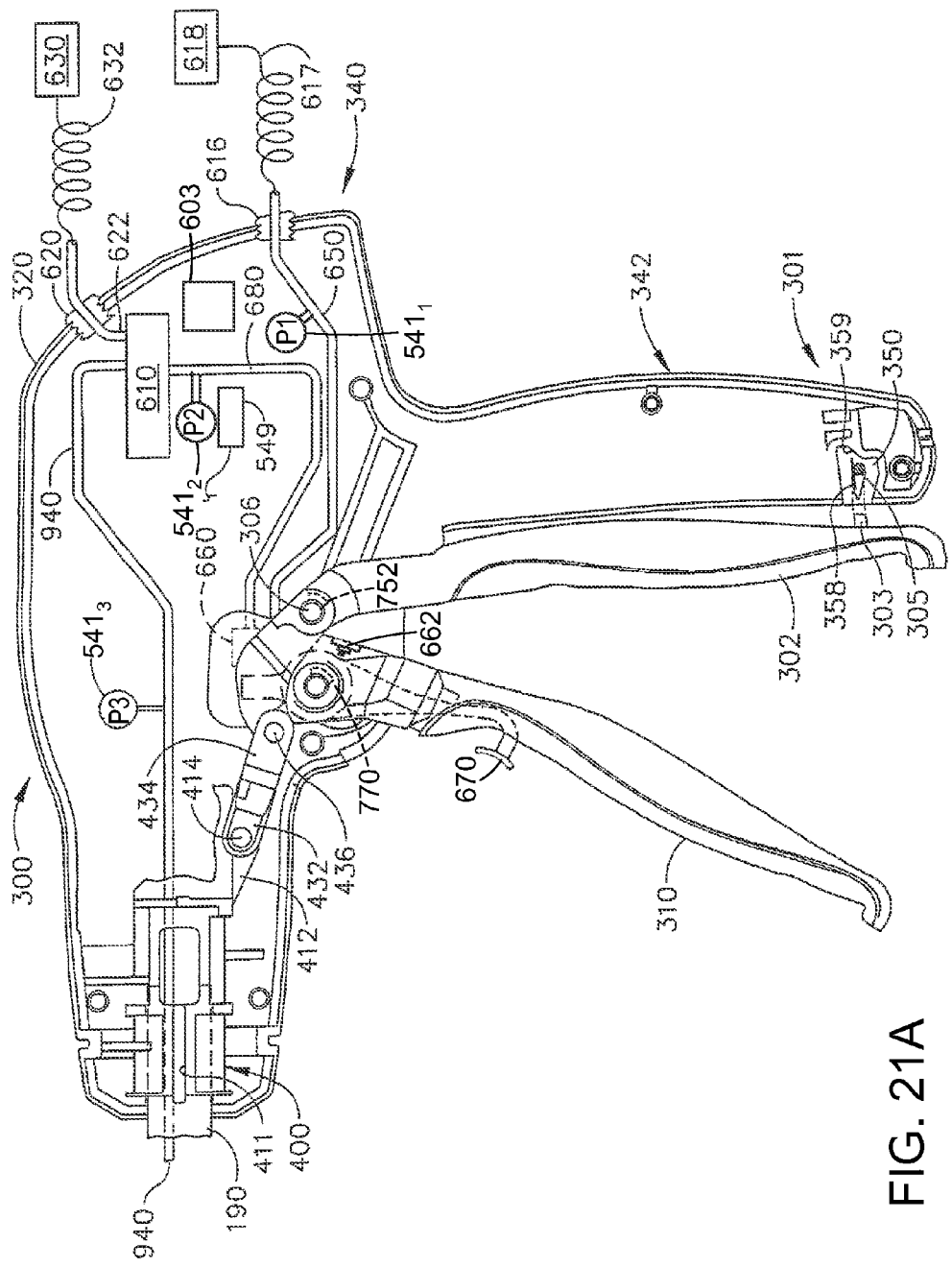
FIG. 21A is a cross-sectional view of another handle assembly embodiment that may be used in connection with the embodiments of FIGS. 17-20 wherein the source of pressurized gas is external to the handle assembly.
Figure 21B:
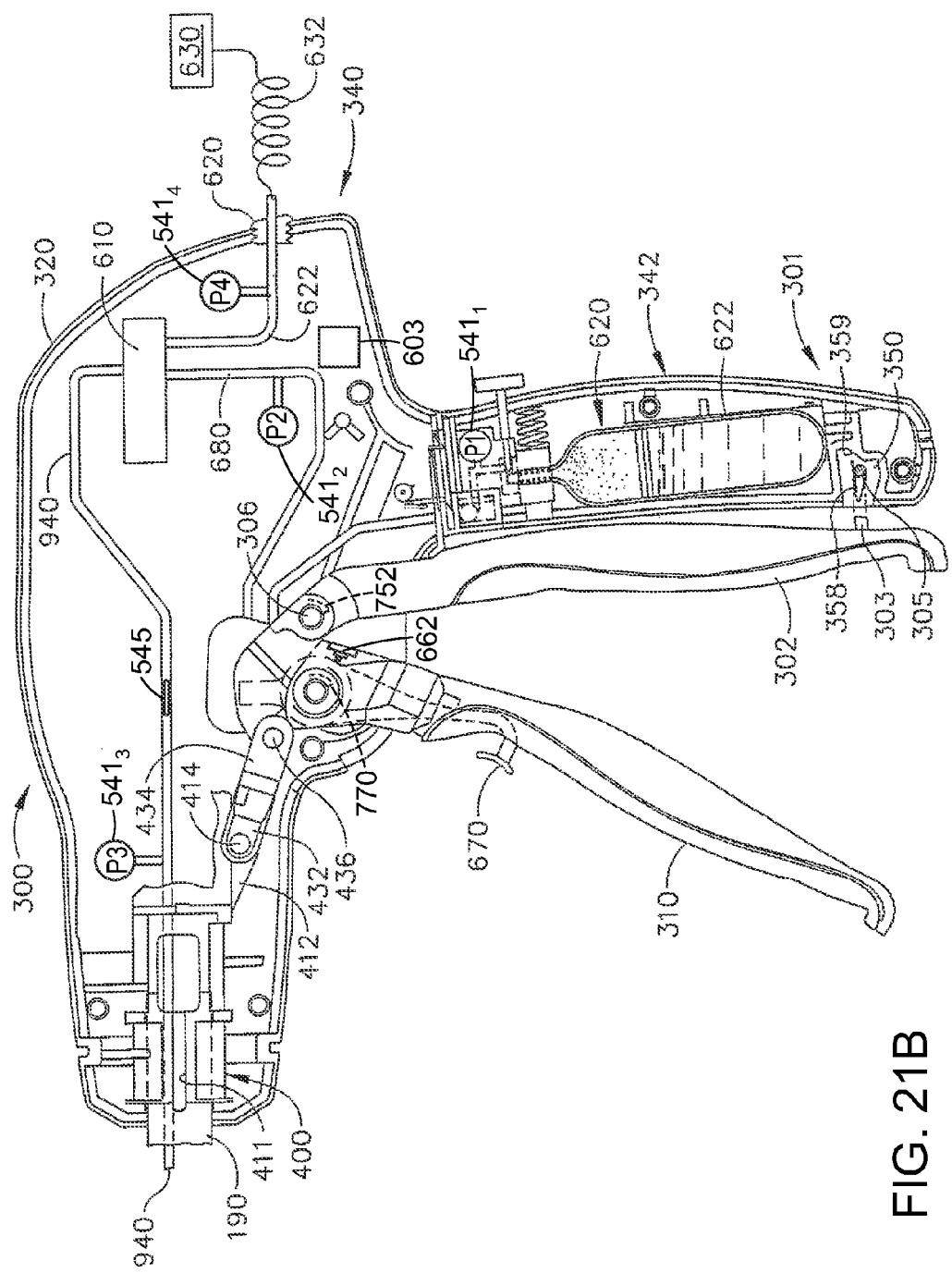
FIG. 21B is a cross-sectional view of another handle assembly embodiment of the surgical cutting and fastening instrument.

Also in this embodiment, a pressure sensor 5413 may be fluidically coupled to supply line 940 as shown in FIGS. 21 and 21A which can function in the manner described above and serves to provide the clinician with a proportionate reading to the forces being experienced by the end effector. In other various embodiments, an audible outlet 545 may be provided in the supply line 940 as shown in FIG. 21B which can function in the manner described above to provide the clinician with an audible feedback mechanism for monitoring the firing forces being experienced by the drive system 500 and ultimately the firing mechanism. In other alternative embodiments, a limit switch 546 (FIG. 18) may be provided within the distal spine segment 110 for detecting an activation member 912' (FIG. 20) on the bellows assembly 900 for automatically controlling the directional switch 610 and/or providing visual and or audible signals indicating that the firing mechanism or knife assembly 30 has reached the end of the firing stroke.

Figure 25:
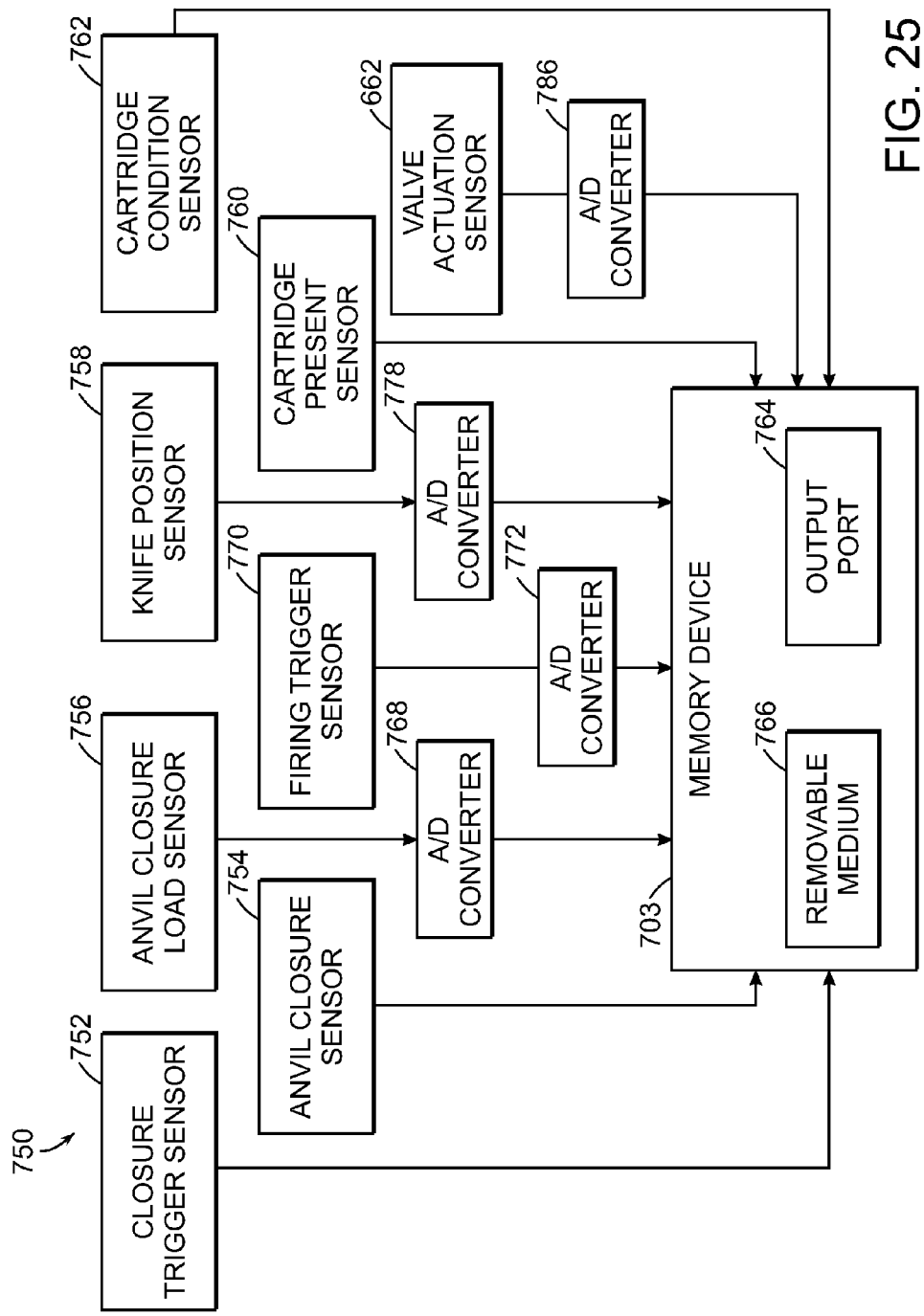
FIG. 25 illustrates various embodiments of a surgical instrument with the capability to record instrument conditions at one or more times during use.

FIG. 25 illustrates various embodiments of a surgical instrument with the capability to record instrument conditions at one or more times during use. FIG. 25 shows a block diagram of a system 750 for recording conditions of the instrument 10. It will be appreciated that the system 750 may be implemented in embodiments of the instrument 10 having pneumatically controlled or pneumatically-assisted firing, for example, as described with reference to embodiments above. The embodiments, however, are not limited in this context.

The system 750 may include various sensors 752, 754, 756, 758, 760, 762, 770 for sensing multiple instrument conditions. The sensors may be positioned, for example, on or within the instrument 10. In various embodiments, the sensors may be dedicated sensors that provide output signals $S_1$ to $S_n$ only for the system 750, or may be dual-use sensors that perform other functions within the instrument 10. For example, sensors 662, 720, 724, and logic module 726 described above may be configured to also provide output signals to the system 750.

Directly or indirectly, each sensor provides a signal $S_1$ to $S_n$ to the memory device 703 (FIG. 26) and/or to the controller 702. The memory device 703 records the signals $S_1$ to $S_n$ as described in more detail below. The memory device 703 may be any kind of device capable of storing or recording the sensor signals $S_1$ to $S_n$. For example, the memory device 703 may include a microprocessor (e.g., controller 702), an Electrically Erasable Programmable Read Only Memory (EEPROM), or any other suitable storage device. The memory device 703 may record the signals provided by the sensors in any suitable manner. For example, in one embodiment, the memory device 703 may record a signal from a particular sensor when that signal changes states. In another embodiment, the memory device 703 may record a state of the system 750, e.g., the signals $S_1$ to $S_n$ from all of the sensors included in the system 750, when the signal $S_1$ to $S_n$ from any sensor changes states. This may provide a snap-shot of the state of the instrument 10. In various embodiments, the memory device 703 and/or sensors may be implemented to include 1-WIRE bus products available from DALLAS SEMICONDUCTOR such as, for example, a 1-WIRE EEPROM.

In various embodiments, the memory device 703 is externally accessible, allowing an outside device, such as a computer, to access the instrument conditions recorded by the memory device 703. For example, the memory device 703 may include a data port 764. The data port 764 may provide the stored instrument conditions according to any wired or wireless communication protocol in, for example, serial or parallel format. The memory device 703 may also include a removable medium 766 in addition to or instead of the output port 764. The removable medium 766 may be any kind of suitable data storage device that can be removed from the instrument 10. For example, the removable medium 766 may include any suitable kind of flash memory, such as a Personal Computer Memory Card International Association (PCM-CIA) card, a COMPACTFLASH card, a MULTIMEDIA card and/or a FLASHMEDIA card. The removable medium 766 may also include any suitable kind of disk-based storage including, for example, a portable hard drive, a compact disk (CD) and/or a digital video disk (DVD).

FIG. 26 illustrates one embodiment of an instrument. The embodiment shown in FIG. 26 shows multiple sensors and a more detailed view of the electronic control module 603. As shown, the electronic control module 603 comprises the controller 720, the memory device 703, the measurement circuit 732, the actuator 706, and the battery 704. The closure trigger sensor 752 senses a condition of the closure trigger 302. As shown in FIG. 26, the closure trigger sensor 752 is positioned between the closure trigger 302 and closure pivot pin 306. It will be appreciated that pulling the closure trigger 302 toward the pistol grip 342 causes the closure trigger 302 to exert a force on the closure pivot pin 306. The sensor 752 may be sensitive to this force, and generate a signal in response thereto, for example, as described above with respect to the valve actuation sensor 662 and FIGS. 22A and 22B. In various embodiments, the closure trigger sensor 752 may be a digital sensor that indicates only whether the closure trigger 302 is actuated or not actuated. In other various embodiments, the closure trigger sensor 752 may be an analog sensor that indicates the force exerted on the closure trigger 302 and/or the position of the closure trigger 302. If the closure trigger sensor 752 is an analog sensor, an analog-to-digital converter may be logically positioned between the sensor 752 and the memory device 703. Also, it will be appreciated that the closure trigger sensor 752 may take any suitable form and be placed at any suitable location that allows sensing of the condition of the closure trigger 302.

FIG. 27 illustrates one embodiment of an anvil closure sensor 754. The anvil closure sensor 754 may sense whether the anvil 40 is closed. The sensor 754 is positioned next to or within the anvil cam slots 28 of the elongate channel 20 as shown. As the anvil 40 is closed, the anvil pivots 43 slides through the anvil cam slots 28 and into contact with the sensor 754, causing the sensor 754 to generate a signal indicating that the anvil 40 is closed. The sensor 754 may be any suitable kind of digital or analog sensor including a proximity sensor. It will be appreciated that when the anvil closure sensor 754 is an analog sensor, an analog-to-digital converter may be included logically between the sensor 754 and the memory device 703 and/or the controller 702.

Anvil closure load sensor 756 is shown placed on an inside bottom surface of the elongate channel 20. In use, the sensor 756 may be in contact with a bottom side of the staple cartridge 50 (not shown in FIG. 27). As the anvil 40 is closed, it exerts a force on the staple cartridge 50 which is transferred to the sensor 756. In response, the sensor 756 generates a signal $S_n$. The signal $S_n$ may be an analog signal proportional to the force exerted on the sensor 756 by the staple cartridge 50 and due to the closing of the anvil 40. Referring the FIG. 25, the analog signal may be provided to an analog-to-digital converter 768 to convert the analog signal to a digital signal before providing it to the memory device 703 and/or the controller 702. It will be appreciated that embodiments where the sensor 756 is a digital or binary sensor may not include analog-to-digital converter 768.

The firing trigger sensor 770 senses the position and/or state of the firing trigger 310. In addition, the firing trigger sensor 770 may take any of the forms described above, and may be analog or digital. FIG. 26 shows an embodiment of the firing trigger sensor 770. In FIG. 26, the firing trigger sensor 770 is mounted between firing trigger 310 and firing trigger pivot pin 370. When firing trigger 310 is pulled, it will exert a force on the firing trigger pivot pin 370 that is sensed by the sensor 770. Referring to FIG. 25, in embodiments where the output of the firing trigger sensor 770 is analog, analog-to-digital converter 772 is included logically between the firing trigger sensor 770 and the memory device 703 and/or the controller 702.

FIG. 28 illustrates one embodiment of a knife position sensor 758 that is suitable for use with the pneumatically actuated piston bar portion 35 protruding from the knife assembly 30. The knife position sensor 758 senses the position of the knife assembly 30 or cutting edge 38 within the elongate channel 20. The sensor 758 includes a magnet 774 coupled to the piston bar portion 35 of the instrument 10. A coil 776 is positioned around the piston bar portion 35. As the knife assembly 30 and cutting edge 38 are reciprocated through the elongate channel 20, the piston bar portion 35 and magnet 774 may move back and forth through the coil 776. This motion relative to the coil induces a voltage in the coil proportional to the position of the piston bar portion 35 within the coil and the cutting edge 38 within the elongate channel 20. This voltage may be provided to the memory device 703 and/or the controller 702, for example, via analog-to-digital converter 778.

In various embodiments, the knife position sensor 758 may instead be implemented as a series of digital sensors (not shown) placed at various positions on or within the elongate shaft assembly 100. The digital sensors may sense a feature of the piston bar portion 35 such as, for example, magnet 774, as the feature reciprocates through the elongate shaft assembly 100. The position of the piston bar portion 35 within the elongate shaft assembly 100, and by extension, the position of the knife assembly 30 may be approximated as the position of the last digital sensor tripped.

Figure 29:
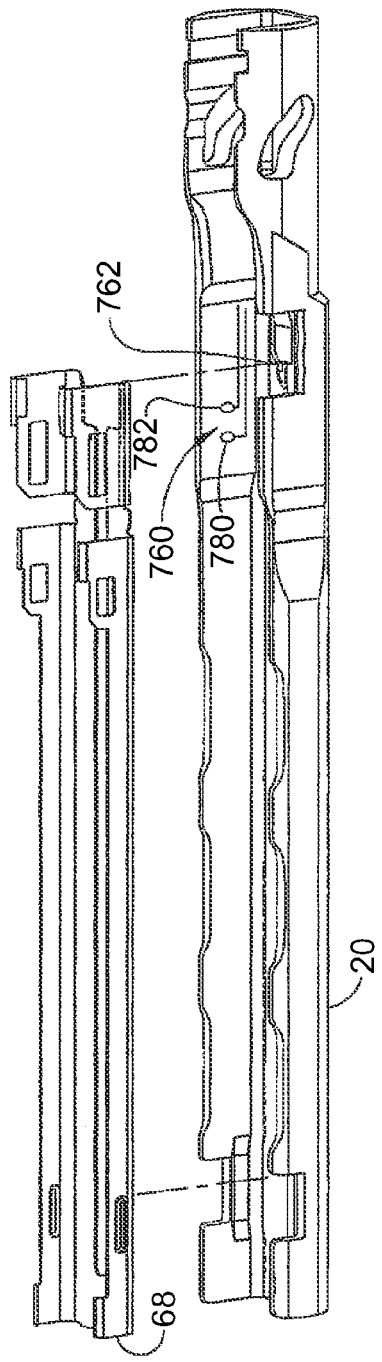
FIGS. 29 and 30 illustrate one embodiment of a cartridge present sensor.
Figure 30:
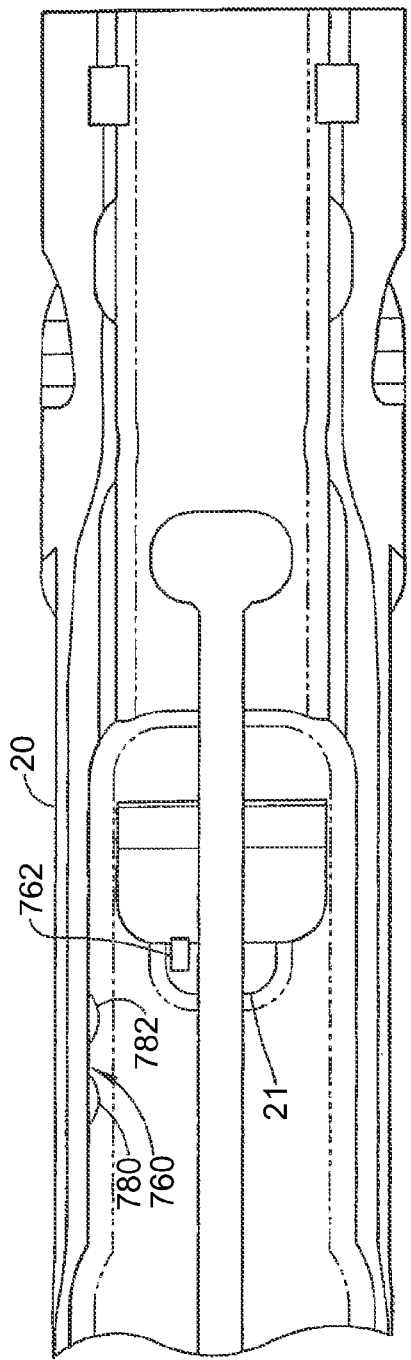

FIGS. 29 and 30 illustrate one embodiment of a cartridge present sensor 760. The cartridge present sensor 760 may sense the presence of the staple cartridge 40 within the elongate channel 20. In some embodiments of the instrument 10, the cartridge present sensor 760 may double as the cartridge lock-out sensor. A cartridge lockout sensor changes states based on whether the end effector 12 includes a staple cartridge 40. For example, if the end effector 12 includes a staple cartridge 40, the lock-out sensor will be in a closed state, allowing current to flow, otherwise, if the end effector 12 does not include a staple cartridge 40, the lock-out sensor will be in an open state to prevent the activation of the instrument 10. In the embodiment shown, the cartridge present sensor 760 includes two contacts 780 and 782. When no cartridge 40 is present, the contacts 780, 782 form an open circuit. When a cartridge 40 is present, the cartridge tray 68 of the staple cartridge 40 contacts the contacts 780, 782, and a closed circuit is formed. When the circuit is open, the sensor 760 may output a logic zero. When the circuit is closed, the sensor 760 may output a logic one. The output of the sensor 760 is provided to the memory device 703 and/or the controller 702 as shown in FIG. 24, for example.

The cartridge condition sensor 762 may indicate whether a cartridge 40 installed within the elongate channel 20 has been fired or spent. As the knife assembly 30 is translated through the end effector 12, it pushes the wedge sled 64, which fires the staple cartridge 40. Then the knife assembly 30 is translated back to its original position, leaving the wedge sled 64 at the distal end of the cartridge 40. Without the wedge sled 64 to guide it, the knife assembly 30 may fall into the locking opening 21 in the elongate channel 20. Sensor 762 may sense whether the knife assembly 30 is present in the locking opening 21, which indirectly indicates whether the cartridge 40 has been spent. It will be appreciated that in various embodiments, sensor 762 may directly sense the presence of the wedge sled 64 at the proximate end of the cartridge 40, thus eliminating the need for the knife assembly 30 to fall into the locking opening 21.

The valve actuation sensor 662 is coupled to the activation trigger 670. The valve actuation sensor 662 may be a digital on/off switch or may be an analog proportional sensor as described with reference to FIGS. 22A and 22B. The output of the valve actuation sensor 662 is coupled to the memory device 703 and/or to the controller 702. When the valve actuation sensor 662 detects the movement of the activation trigger 670 it sends an actuation signal $S_n$ to the controller 702 to actuate the variable flow rate pneumatic valve 660. When the valve actuation sensor 662 is a digital on/off switch, it sends an electrical signal $S_n$ to the controller 702 to actuate the variable flow rate pneumatic valve 660. When the valve actuation sensor 662 is an analog proportional sensor, the sensor 662 provides an analog signal $S_n$ that is proportional to the pressure applied on the valve actuation sensor 662 by the activation trigger 670. The proportional output signal $S_n$ is provided to an analog-to-digital converter 786 to convert the analog signal to a digital signal before providing it to the memory device 703. The controller 702 adjusts the variable flow rate pneumatic valve 660 to produce the desired flow rate of the pressurized gas as previously discussed based on the pressure applied to the valve actuation sensor 662 by the actuation trigger.

Figure 31A:
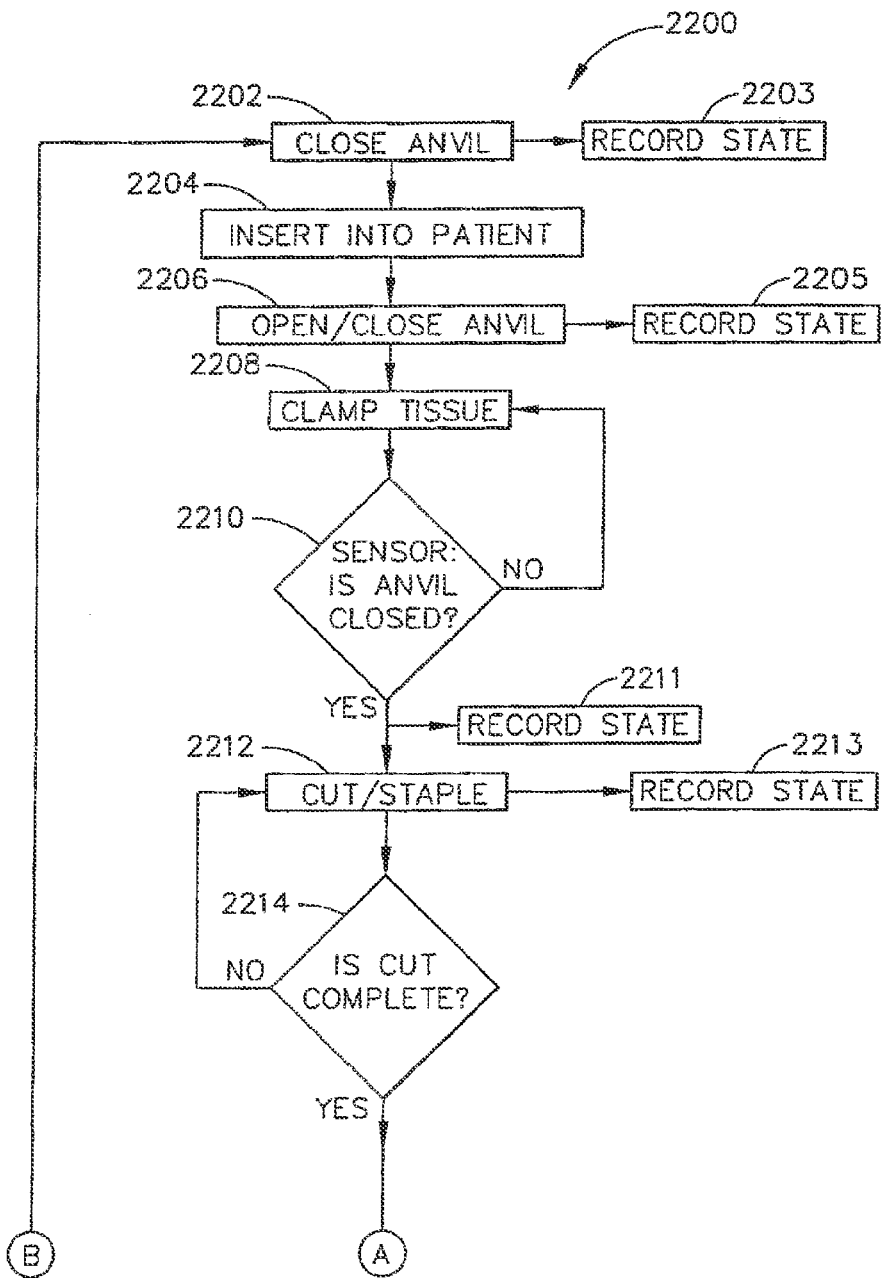
FIGS. 31A and 31B illustrate one embodiment of a process flow for operating embodiments of a surgical instrument configured as an endocutter and having the capability to record instrument conditions according to various embodiments.
Figure 31B:
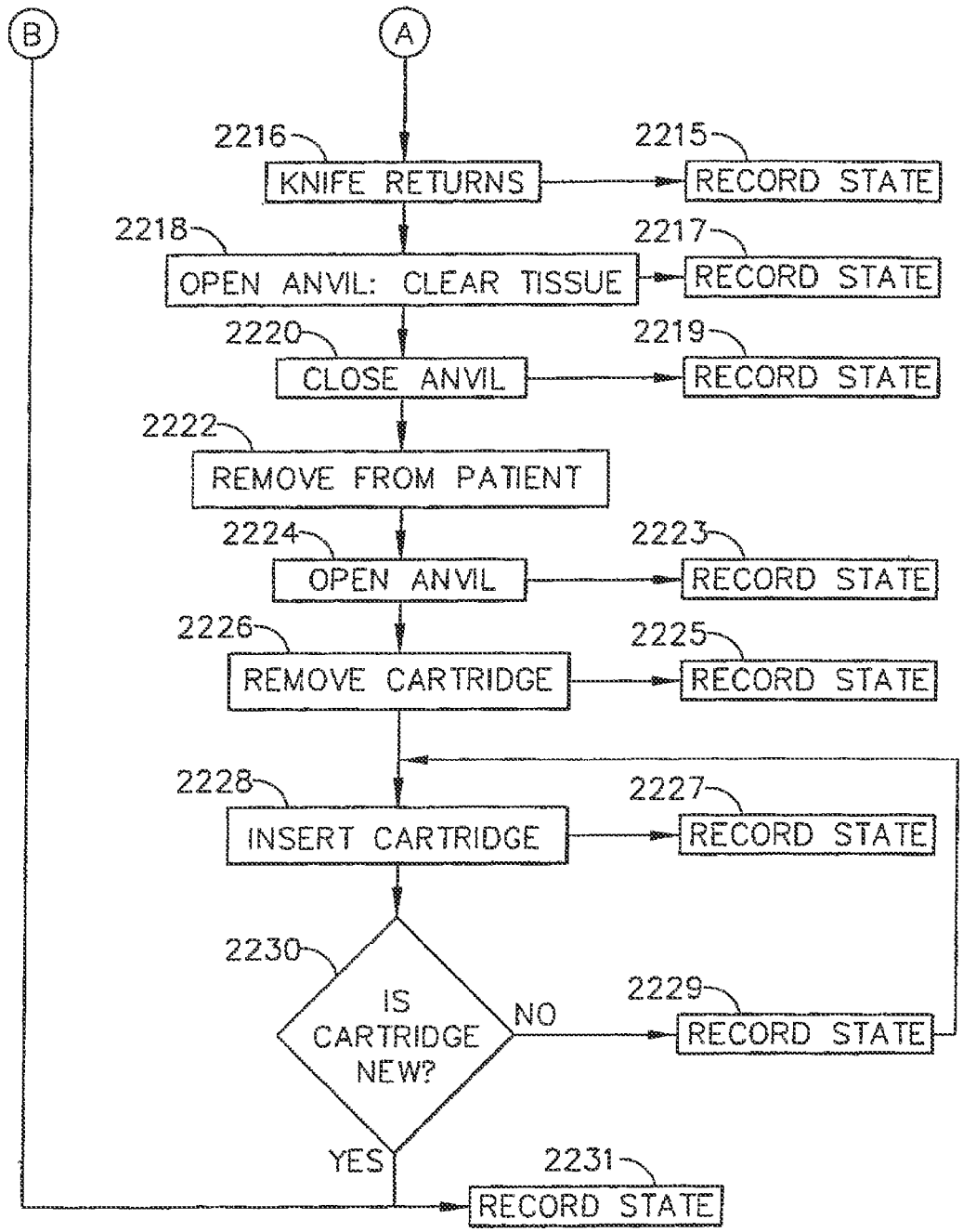

FIGS. 31A and 31B illustrate one embodiment of a process flow 2200 for operating embodiments of the surgical instrument 10 configured as an endocutter and having the capability to record instrument conditions according to various embodiments. At box 2202, the anvil 40 of the instrument 10 may be closed. This causes the closure trigger sensor 752 and or the anvil closure sensor 756 to change state. In response, the memory device 703 may record the state of all of the sensors in the system 750 at box 2203. At box 2204, the instrument 10 may be inserted into a patient. When the instrument is inserted, the anvil 40 may be opened and closed at box 2206, for example, to manipulate tissue at the surgical site. Each opening and closing of the anvil 40 causes the closure trigger sensor 752 and/or the anvil closure sensor 756 to change state. In response, the memory device 703 records the state of the system 750 at box 2205.

At box 2208, tissue is clamped for cutting and stapling. If the anvil 40 is not closed at decision block 2210, continued clamping is required. If the anvil 40 is closed, then the sensors 752, 754 and/or 756 may change state, prompting the memory device 703 to record the state of the system at box 2213. This recording may include a closure pressure received from sensor 756. At box 2212, cutting and stapling may occur. Firing trigger sensor 770 may change state as the firing trigger 310 is pulled toward the pistol grip 342. Also, as the knife assembly 30 moves through the elongate channel 20, the knife position sensor 758 will change state. In response, the memory device 703 may record the state of the system 750 at box 2013.

When the cutting and stapling operations are complete, the knife assembly 30 may return to a pre-firing position. Because the cartridge 50 has now been fired, the knife assembly 30 may fall into the locking opening 21, changing the state of cartridge condition sensor 762 and triggering the memory device 703 to record the state of the system 750 at box 2015.

The anvil 40 may then be opened to clear the tissue. This may cause one or more of the closure trigger sensor 752, anvil closure sensor 754 and anvil closure load sensor 756 to change state, resulting in a recordation of the state of the system 750 at box 2017. After the tissue is cleared, the anvil 40 may be again closed at box 2220. This causes another state change for at least sensors 752 and 754, which in turn causes the memory device 703 to record the state of the system at box 2019. Then the instrument 10 may be removed from the patient at box 2222.

If the instrument 10 is to be used again during the same procedure, the anvil 40 may be opened at box 2224, triggering another recordation of the system state at box 2223. The spent cartridge 50 may be removed from the end effector 12 at box 2226. This causes cartridge present sensor 760 to change state and cause a recordation of the system state at box 2225. Another cartridge 50 may be inserted at box 2228. This causes a state change in the cartridge present sensor 760 and a recordation of the system state at box 2227. If the other cartridge 50 is a new cartridge, indicated at decision block 2230, its insertion may also cause a state change to cartridge condition sensor 762. In that case, the system state may be recorded at box 2231.

FIG. 32 shows one embodiment of a memory map 2300 from the memory device 703. The memory map 2300 includes a series of columns 2302, 2304, 2306, 2308, 2310, 2312, 2314, 2316 and rows (not labeled). Column 2302 shows an event number for each of the rows. The other columns represent the output of one sensor of the system 750. All of the sensor readings recorded at a given time may be recorded in the same row under the same event number. Hence, each row represents an instance where one or more of the signals from the sensors of the system 750 are recorded.

Column 2304 lists the closure load recorded at each event. This may reflect the output of anvil closure load sensor 756. Column 2306 lists the firing stroke position. This may be derived from the knife position sensor 758. For example, the total travel of the knife assembly 30 may be divided into partitions. The number listed in column 2306 may represent the partition where the knife assembly 30 is currently present. The firing load is listed in column 2308. This may be derived from the firing trigger sensor 770. The knife position is listed at column 2310. The knife position may be derived from the knife position sensor 758 similar to the firing stroke. Whether the anvil 40 is open or closed may be listed at column 2312. This value may be derived from the output of the anvil closure sensor 754 and/or the anvil closure load sensor 756. Whether the wedge sled 64 is present, or whether the cartridge 50 is spent, may be indicated at column 2314. This value may be derived from the cartridge condition sensor 762. Finally, whether the cartridge 50 is present may be indicated a column 2316. This value may be derived from cartridge present sensor 760. It will be appreciated that various other values may be stored at memory device 703 including, for example, the end and beginning of firing strokes, for example, as measured by various other sensors.

Figure 33:
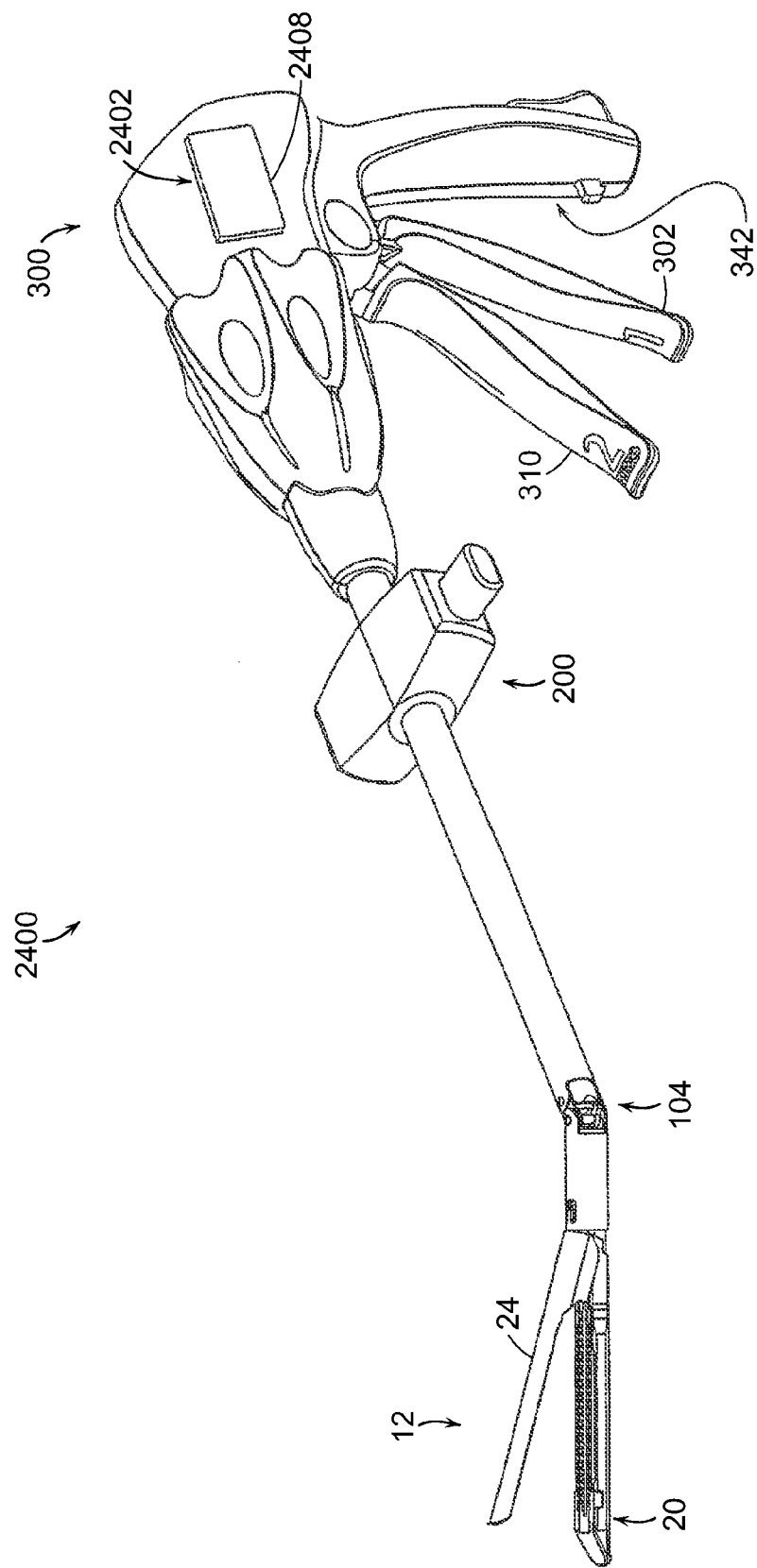
FIG. 33 illustrates various embodiments of a surgical instrument.

FIG. 33 illustrates various embodiments of a surgical instrument 2400. The surgical instrument 2400 may be similar to the surgical instrument 10 described hereinabove, but also includes a status module 2402 releasably connected thereto. Although the status module 2402 is shown in FIG. 33 as being connected to the exterior lower side piece of the handle assembly 300, it is understood that the status module 2402 may be connected to the surgical instrument 2400 at any suitable location. According to various embodiments, the handle assembly 300 of the surgical instrument 2400 defines a recess structured and arranged to receive the status module 2402.

Figure 34:
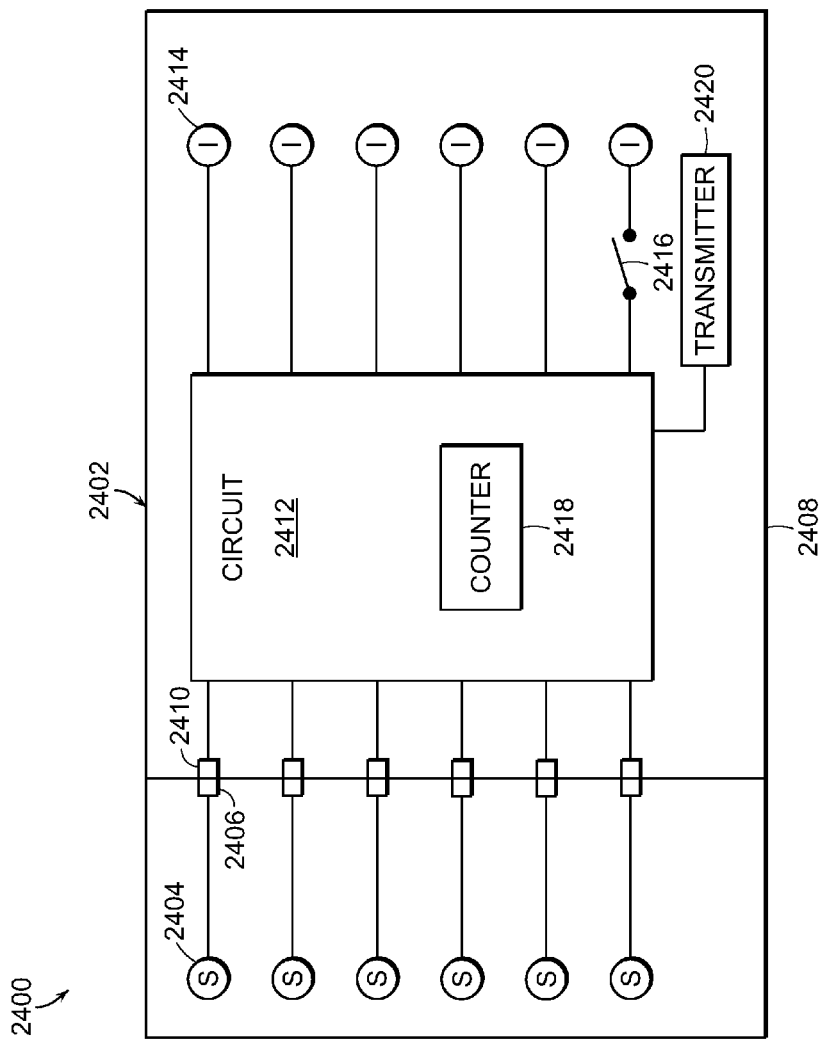
FIG. 34 illustrates a schematic of one embodiment of a surgical instrument comprising a plurality of sensors.

FIG. 34 illustrates a schematic of one embodiment of a surgical instrument 2400 comprising a plurality of sensors 2404. The plurality of sensors 2404 includes, for example, an articulation angle sensor, an anvil position sensor, a cartridge sensor, a closure trigger sensor, a closure force sensor, a firing force sensor, a knife position sensor, a lockout condition sensor, or any combination thereof. Each sensor 2404 may be in electrical communication with a different contact 2406 (shown schematically in FIG. 34) positioned proximate the exterior of the surgical instrument 2400.

The sensors 2404 may be embodied in any suitable manner. For example, the articulation angle sensor may be embodied as, for example, a potentiometer that comprises a portion of the articulation control 200 and outputs a signal that indicates the relative articulation angle of the end effector 12. The anvil position sensor may be embodied as, for example, the anvil closure sensor 754 discussed above. The cartridge sensor may be embodied as, for example, the cartridge present sensor 760 discussed above. The closure trigger sensor may be embodied as, for example, the closure trigger sensor 752 discussed above. The closure force sensor may be embodied as, for example, the anvil closure load sensor 756 discussed above. The firing force sensor may be embodied as, for example, the firing trigger sensor 770 discussed above. The knife position sensor may be embodied as, for example, the knife position sensor 758 discussed above. The lockout condition sensor may be embodied as, for example, the cartridge lockout sensor or the cartridge present sensor 760 discussed above.

According to various embodiments, the status module 2402 comprises a housing 2408 structured and arranged to releasably connect to the surgical instrument 2400. The status module 2408 comprises a plurality of contacts 2410 (shown schematically in FIG. 34), wherein each individual contact 2410 is structured and arranged to be in electrical communication with a different sensor 2404 of the surgical instrument 2400 when the housing 2408 is connected to the surgical instrument 2400. For example, when the status module 2402 is connected to the surgical instrument 2400, each contact 2410 of the status module 2402 may be aligned with a respective corresponding contact 2406 of the surgical instrument 2400, thereby placing each contact 2410 of the status module 2402 in electrical communication with a different sensor 2404.

The status module 2402 further comprises a circuit 2412 (shown schematically in FIG. 34) in communication with at least one of the contacts 2410, and a plurality of indicators 2414 (shown schematically in FIG. 34). At least one of the indicators 2414 is in electrical communication with the circuit 2412. The circuit 2412 comprises a drive circuit, and is structured and arranged to drive at least one of the indicators 2414. According to various embodiments, the circuit 2412 may further comprise, as shown schematically in FIG. 34, a switch 2416, a counter 2418, a transmitter 2420, or any combination thereof. In one embodiment, the circuit is coupled to the electronic control module 603.

The switch 2416 is in electrical communication with at least one of the indicators 2414, and may be utilized to disable the respective indicator 2414 that is in electrical communication therewith. According to various embodiments, the switch 2416 may comprise a portion of the status module 2402 other than the circuit 2412, or a portion of the surgical instrument 2400 other than the status module 2402. For such embodiments, the switch 2416 may be in electrical communication with the circuit 2412.

The counter 2418 may be utilized to determine the number of firings, the number of firings remaining and/or the post-clamping wait time. According to various embodiments, the counter 2418 may comprise a portion of the status module 2402 other than the circuit 2412. According to other embodiments, the counter 2418 may comprise a portion of the surgical instrument 2400 other than the status module 2402. For such embodiments, the counter 2418 may be in electrical communication with the circuit 2412.

The transmitter 2420 may be utilized to wirelessly transmit information sensed by the plurality of sensors 2404 to a wireless receiver (not shown) associated with a monitor (not shown) that may be viewed by a user of the surgical instrument 2400 while the user is performing a procedure. The information may be wirelessly transmitted continuously or periodically. The displayed information may include, for example, firing progress information, compression load information, knife load information, number of firings, procedure time, compression wait time and/or battery level. According to other various embodiments, the transmitter 2420 may comprise a portion of the status module 2402 other than the circuit 2412, or a portion of the surgical instrument 2400 other than the status module 2402. For such embodiments, the transmitter 2420 may be in electrical communication with the circuit 2412.

Figure 35:
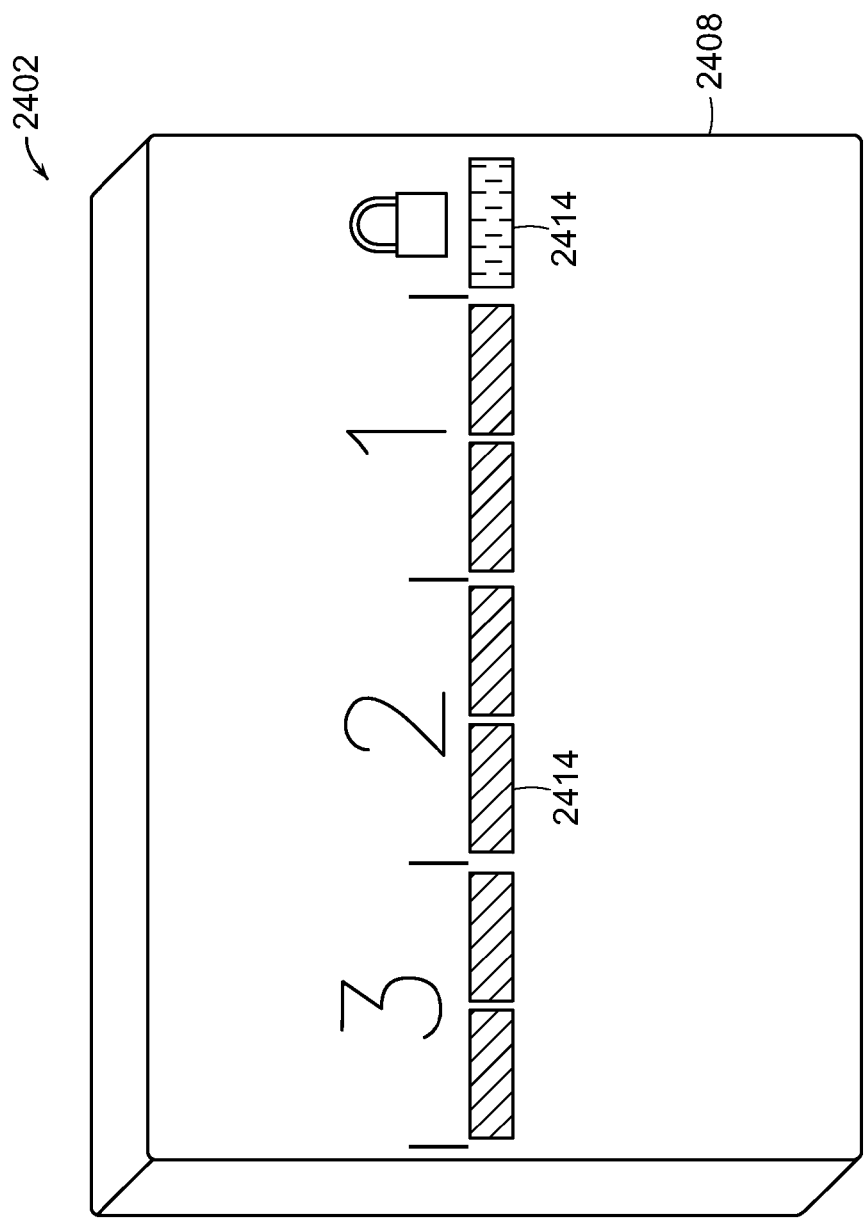
FIG. 35 illustrates one embodiment of an indicator to provide audible and visual feedback.
Figure 36:
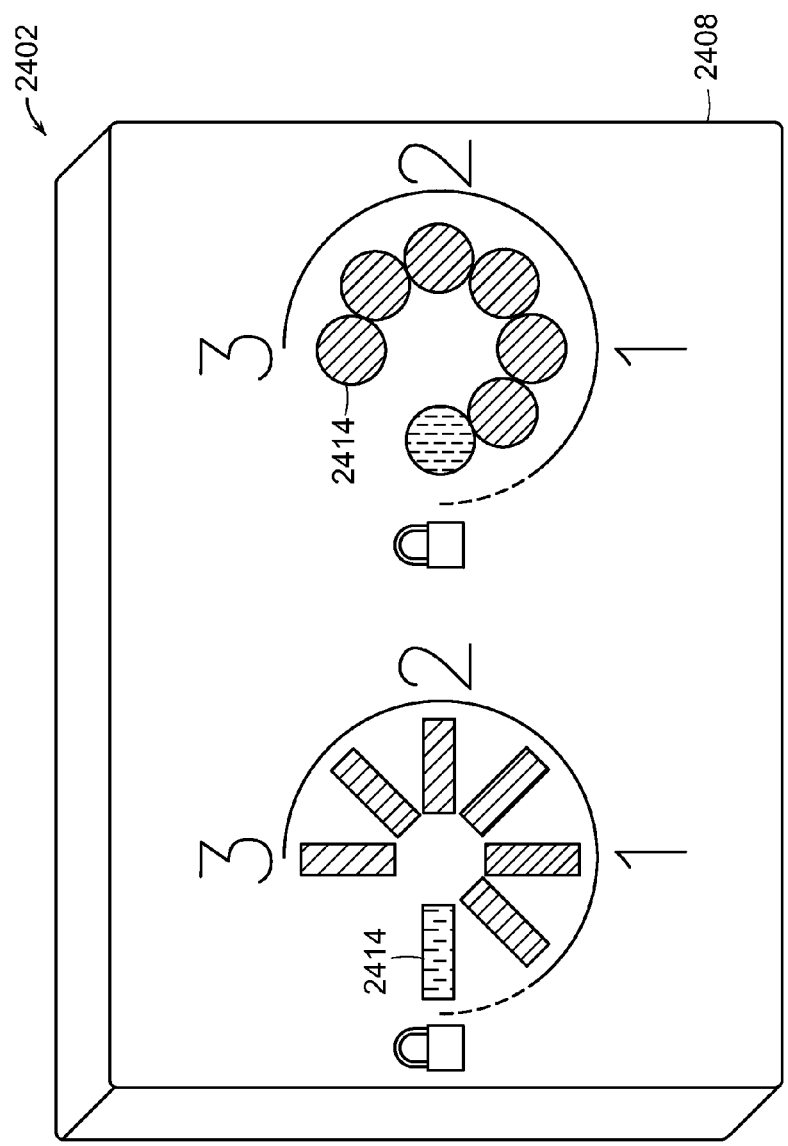
FIG. 36 illustrates one embodiment of a status module.
Figure 37:
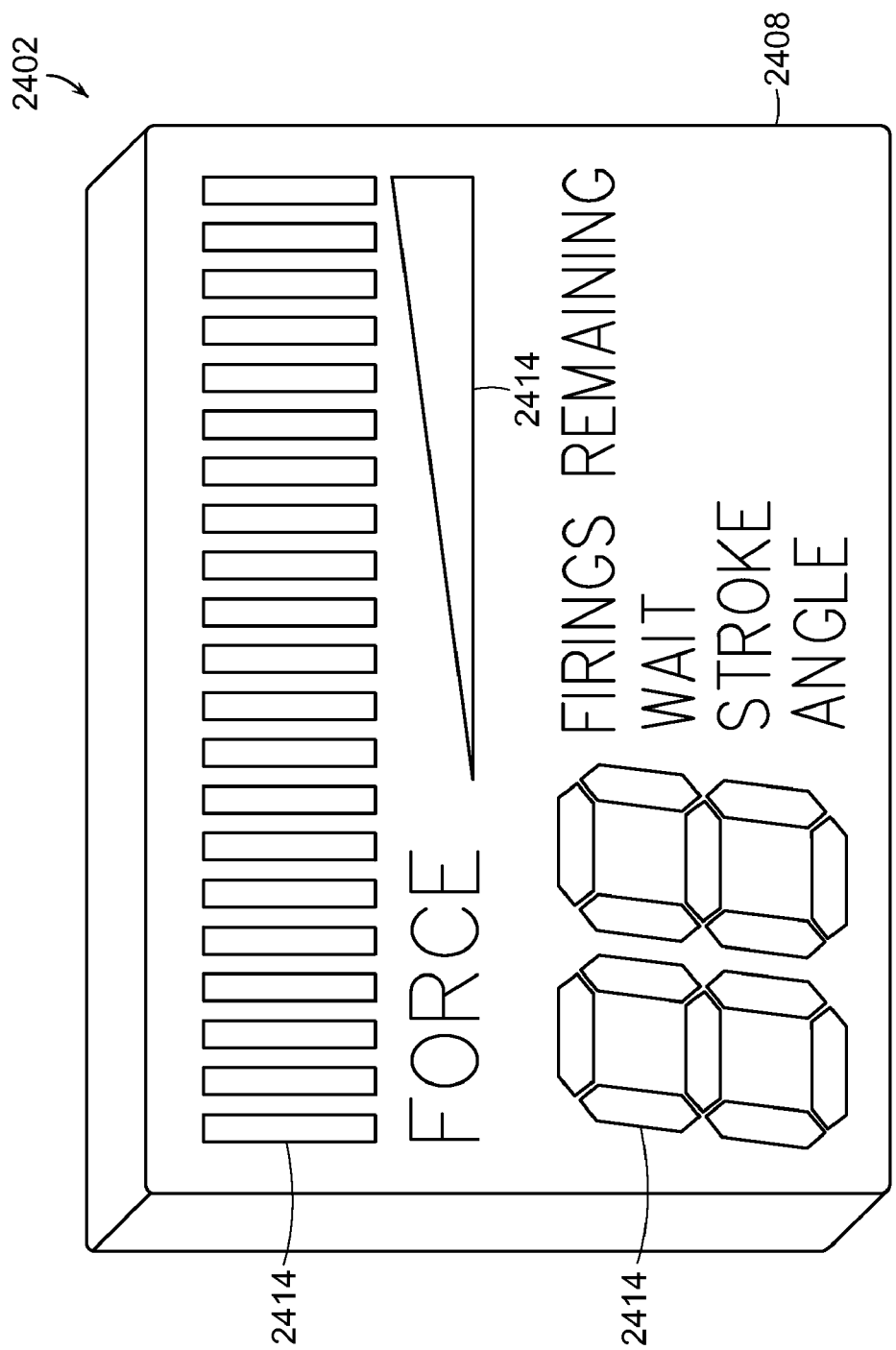
FIG. 37 illustrates one embodiment of a status module.

FIGS. 35-37 illustrate various embodiments of the status module 2402. As shown, the status module 2402 may comprise different types of indicators 2414. According to various embodiments, the indicators 2414 may comprise one or more visual indicators such as, for example, a light emitting diode, a multi-color light emitting diode and/or a display or any combination thereof. The display may comprise, for example, an alpha numeric display, a dot matrix display and/or a liquid crystal display. According to various embodiments, at least one of the indicators 2414 may comprise an audible indicator such as, for example, an audio output device. The audible output device may be embodied as, for example, a speaker, and may be in electrical communication with the switch 2416. According to various embodiments, the indicators 2414 may comprise at least one visual indicator and at least one audible indicator.

FIG. 35 illustrates one embodiment of an indicator to provide audible and visual feedback. In operation, the indicators 2414 may provide visual and audible feedback to a user of the surgical instrument 2400. For example, as shown in FIG. 35, an indicator 2414 (e.g., a light emitting diode) may be utilized to indicate whether the closure trigger 302 is in the locked position, whether a predetermined post-clamping wait period has been completed and/or whether a staple cartridge 50 is loaded. Different indicators 2414 may emit different colors of light. As used in FIGS. 35 and 36, different hatching indicates different colors. An indicator 2414 (e.g., a multi-color light emitting diode) may be utilized for multiple status indications of a particular function of the surgical instrument 2400. For example, to indicate the status of the staple cartridge 50, a multi-color light emitting diode may emit green light if a loaded staple cartridge 50 is in the elongate channel 20, yellow light if a spent staple cartridge 50 is in the elongate channel 20, or red light if a staple cartridge 50 is not in the channel 20. Similarly, to indicate the status of a cutting force being exerted by the surgical instrument 2400, a multi-color light emitting diode may emit green light if the cutting force being exerted is in a normal range, yellow light if the cutting force being exerted is in an elevated range, or red light if the cutting force being exerted is in a high load range. It is understood that the indicators 2414 may be utilized for multiple status indications of other functions of the surgical instrument 2400 such as, for example, battery level.

As shown in FIG. 35, a line of indicators 2414 (e.g., light emitting diodes) may be utilized to indicate the progression of the knife assembly 30, the percentage of the maximum closure force being exerted, the percentage of the maximum firing force being exerted, or the current articulation angle of the end effector 12. Such indications may provide a user of the surgical instrument 2400 with feedback concerning the forces involved in operating the surgical instrument 2400 and feedback as to how close the surgical instrument 2400 is operating to its maximum capacity. Although only one line of indicators 2414 is shown in FIG. 35, it is understood that the status module 2402 may comprise any number of lines of indicators 2414.

FIG. 36 illustrates one embodiment of a status module. As shown in FIG. 36, the status module 2402 may comprise indicators 2414 (e.g., light emitting diodes) arranged in two circular orientations. For such embodiments, the status module 2402 may be capable of providing more concurrent information to a user of the surgical instrument 2400 than the status module 2402 shown in FIG. 35. Although two circular arrangements of indicators are shown in FIG. 36, it is understood that the status module 2402 may comprise any number of indicators 2414 arranged in any number of orientations. For example, the status module 2402 may comprises indicators 2414 arranged in a pyramid pattern.

FIG. 37 illustrates one embodiment of a status module. As shown in FIG. 37, the indicators 2414 of the status module 2402 may comprise a line of light emitting diodes and at least one display (e.g., a liquid crystal display). For such embodiments, the status module 2402 may be capable of providing more concurrent information to a user of the surgical instrument 2400 than the status module 2402 shown in FIG. 35 or FIG. 36. For example, the light emitting diodes may show reaction force at the anvil 40 and staple cartridge 50, the battery level, or the articulation angle in the form of a bar graph. The display may show information concerning closure forces, firing forces, the number of firings remaining, post-clamping wait time, stroke progression, or articulation angle in the form of digits.

While several embodiments of the instrument 10 have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope of the disclosed embodiments of the instrument 10 as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A status module for use with a pneumatically powered surgical instrument comprising at least one sensor, the status module comprising:
    a housing structured and arranged to releasably mount on the pneumatically powered surgical instrument;
    at least one contact, wherein an individual contact is structured and arranged to be in electrical communication with a different sensor when the housing is connected to the pneumatically powered surgical instrument, and wherein the at least one sensor is fluidically coupled to the pneumatically powered surgical instrument;
    a circuit in electrical communication with the at least one contact; and
    at least one electrical indicator in electrical communication with the circuit, wherein the at least one electrical indicator is located on the housing to provide a current status of the surgical instrument to the user during a surgical procedure.

2. The status module of claim 1, wherein the circuit comprises a drive circuit.

3. The status module of claim 2, wherein the circuit further comprises a counter.

4. The status module of claim 1, wherein the at least one electrical indicator comprises a visual indicator in electrical communication with the circuit.

5. The status module of claim 4, wherein the visual indicator comprises a light emitting diode.

6. The status module of claim 4, wherein the visual indicator comprises at least one of the following:
   an alpha numeric display;
   a dot matrix display; and
   a liquid crystal display.

7. The status module of claim 1, wherein the at least one electrical indicator comprises:
   a visual indicator in electrical communication with the circuit; and
   an audible indicator in electrical communication with the circuit.

8. The status module of claim 7, wherein the audible indicator comprises an audio output device.

9. The status module of claim 7, further comprising a switch in electrical communication with the audible indicator.

10. The status module of claim 1, further comprising a transmitter in electrical communication with the circuit.

11. The status module of claim 1, further comprising an electronic control module coupled to an electrically controlled variable flow rate pneumatic valve to control the flow rate therethrough, wherein the electronic control module is in electrical communication with the circuit.

12. The status module of claim 11, wherein the electrically controlled variable flow rate pneumatic valve is coupled to a pneumatically-actuated drive member and coupled to the electronic control module.

13. A surgical instrument, comprising:
   a pneumatically-actuated drive member;
   an electronic control module coupled to the pneumatically-actuated drive member;
   a plurality of sensors; and
   a status module, wherein the status module comprises:
      a housing releasably mounted on the surgical instrument;
      at least one contact, wherein an individual contact is in electrical communication with a different sensor
      a circuit in electrical communication with the at least one contact; and
      at least one electrical indicator, wherein the at least one indicator is in electrical communication with the circuit, wherein the at least one electrical indicator is located on the housing to provide a current status of the surgical instrument to the user during a surgical procedure.

14. The surgical instrument of claim 13, wherein the at least one sensor comprises at least one of the following:
   an articulation angle sensor;
   an anvil position sensor;
   a cartridge sensor;
   a closure trigger sensor;
   a closure force sensor;
   a firing force sensor;
   a knife position sensor;
   a lockout condition sensor;
   a pressure sensor; and
   a valve actuation sensor.

15. The surgical instrument of claim 13, wherein the circuit comprises a drive circuit.

16. The surgical instrument of claim 13, wherein the at least one electrical indicator comprises a visual indicator in electrical communication with the circuit.

17. The surgical instrument of claim 16, wherein the visual indicator comprises a light emitting diode.

18. The surgical instrument of claim 16, wherein the visual indicator comprises at least one of the following:
   an alpha numeric display;
   a dot matrix display; and
   a liquid crystal display.

19. The surgical instrument of claim 13, wherein the at least one electrical indicator comprises:
   a visual indicator in electrical communication with the circuit; and
   an audible indicator in electrical communication with the circuit.

20. The surgical instrument of claim 19, wherein the audible indicator is an audio output device.

21. The surgical instrument of claim 19, further comprising a switch in electrical communication with the audible indicator.

22. The surgical instrument of claim 13, further comprising a transmitter in electrical communication with the circuit.

23. The surgical instrument of claim 13, further comprising an end effector comprising a moveable cutting instrument for cutting an object positioned in the end effector, the end effector coupled to the pneumatically-actuated drive member.

24. The surgical instrument of claim 23, further comprising an electrically controlled variable flow rate pneumatic valve to control the flow rate therethrough coupled to the pneumatically-actuated drive member and coupled to the electronic control module.

* * * * *